US009657079B2

(12) United States Patent
Spetzler et al.

(10) Patent No.: US 9,657,079 B2
(45) Date of Patent: *May 23, 2017

(54) TRUNCATED GLP-1 DERIVATIVES AND THEIR THERAPEUTIC USE

(71) Applicant: Novo Nordisk A/S, Bagsvaerd (DK)

(72) Inventors: Jane Spetzler, Broenshoej (DK); Lauge Schaeffer, Lyngby (DK); Jesper Lau, Farum (DK); Janos T. Kodra, Copenhagen OE (DK); Kjeld Madsen, Videbaek (DK); Patrick W. Garibay, Holte (DK); Jacob Kofoed, Vaerloese (DK); Steffen Reedtz-Runge, Birkeroed (DK); Ingrid Pettersson, Frederiksberg (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 14/299,638

(22) Filed: Jun. 9, 2014

(65) Prior Publication Data

US 2014/0296131 A1    Oct. 2, 2014

Related U.S. Application Data

(63) Continuation of application No. 12/676,453, filed as application No. PCT/EP2008/061833 on Sep. 5, 2008, now abandoned.

(60) Provisional application No. 60/971,932, filed on Sep. 13, 2007, provisional application No. 61/024,939, filed on Jan. 31, 2008.

(30) Foreign Application Priority Data

Sep. 5, 2007  (EP) .................................. 07115743
Jan. 28, 2008  (EP) .................................. 08101010

(51) Int. Cl.
| | | |
|---|---|---|
| A61K 38/16 | (2006.01) | |
| C07K 14/00 | (2006.01) | |
| C07K 14/605 | (2006.01) | |
| A61K 38/00 | (2006.01) | |

(52) U.S. Cl.
CPC ............ *C07K 14/605* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,968,899 A | | 10/1999 | Sekine et al. | |
| 6,268,343 B1 * | | 7/2001 | Knudsen | A61K 38/2264 514/11.7 |
| 6,458,924 B2 * | | 10/2002 | Knudsen | A61K 38/26 530/324 |
| 7,235,627 B2 * | | 6/2007 | Knudson | A61K 31/426 530/308 |
| 7,271,149 B2 * | | 9/2007 | Glaesner | C07H 21/04 514/11.7 |
| 8,097,698 B2 * | | 1/2012 | Knudsen | A61K 31/426 530/308 |
| 8,895,694 B2 * | | 11/2014 | Spetzler | A61K 38/26 530/300 |
| 2001/0011071 A1 | | 8/2001 | Knudsen et al. | |
| 2007/0203058 A1 | | 8/2007 | Lau et al. | |

FOREIGN PATENT DOCUMENTS

| | | |
|---|---|---|
| EP | 1364967 A2 | 11/2003 |
| JP | 05-506427 | 9/1993 |
| JP | 2001-504105 A | 3/2001 |
| JP | 2006-520818 A | 9/2006 |
| WO | 96/29342 | 9/1996 |
| WO | 9808871 A1 | 3/1998 |
| WO | 99/43708 A1 | 9/1999 |
| WO | 00/34331 | 6/2000 |
| WO | 00/69911 | 11/2000 |
| WO | 01/04156 | 1/2001 |
| WO | 02/46227 A2 | 6/2002 |
| WO | 03/011892 A2 | 2/2003 |
| WO | 2005/027978 A2 | 3/2005 |
| WO | 2005/058954 A1 | 6/2005 |
| WO | 2006/005667 A2 | 1/2006 |
| WO | 2006/037810 | 4/2006 |
| WO | 2006/097535 A2 | 9/2006 |
| WO | 2006/097536 A2 | 9/2006 |
| WO | 2006/097537 A2 | 9/2006 |
| WO | 2006/097538 | 9/2006 |

OTHER PUBLICATIONS

Pan, 2006, JBC, 281, 12506-12515.*
Runge et al., "Crystal Structure of the Ligand-Bound Glucagon-Like Peptide-1 Receptor Extracellular Domain," J Biol Chem 2008, vol. 283, No. 17, pp. 11340-11347.
Adelhorst, K et al Journal of Biological Chemistry Structure Activity Studies of GLP-1 1994 269 9 6275-6278.
Knudsen, L.B. Journal of Medicinal Chemistry Glucagon-Like Peptide-1: The Basis of a New Class of Treatment for Type 2 Diabetes 2004 47 17 4128-4134.
Leger et al., "Identification of CJC-1131-Albumin Bioconjugate as a Stable and Bioactive GLP-1 (7-36) Analog," Bioorganic and Medicinal Chemistry Letters, vol. 14, pp. 4395-4398 (2004).
Pan, 2006 Journal of Biological Chemistry vol. 281 pp. 12506-12515.
The Medical Dictionary Online. http://cancerweb.ncl.ac.uklomd/abouthtml. 2005.
Nauck, M A. Regulatory Peptides. "Glucagon-Like Peptide 1 and its Derivatives in the Treatment od Diabetes." 2005. vol. 128(2). pp. 135-148.
David M. Irwin, Trout and chicken Proglucagon: Alternative Splicing Generates mRNA Transcripts Encoding Glucagon-Like Peptide 2, Molecular Endocrinology, 1995, vol. 9 No. 3, 267-277.

* cited by examiner

*Primary Examiner* — Satyanarayana R Gudibande
(74) *Attorney, Agent, or Firm* — Richard W. Bork

(57) ABSTRACT

The invention relates to truncated GLP-1 analogs, in particular a GLP-1 analog which is a modified GLP-1(7-35) (SEQ ID No 1) having: i) a total of 2, 3, 4, 5 6, 7, 8, or 9 amino acid substitutions as compared to GLP-1(7-35), including a) a Glu residue at a position equivalent to position 22 of GLP-1(7-35), and b) an Arg residue at a position equivalent to position 26 of GLP-1(7-35); as well as derivatives thereof, and therapeutic uses and compositions. These analogs and derivatives are highly potent, have a good binding affinity to the GLP-1 receptor, also to the extracellular domain of the GLP-1 receptor, which is of potential relevance achieving long-acting, stable GLP-1 compounds with a potential for once weekly administration.

14 Claims, No Drawings

TRUNCATED GLP-1 DERIVATIVES AND THEIR THERAPEUTICAL USE

CROSS-REFERENCE TO RELATED APPLICATIONS

This application is a continuation of U.S. application Ser. No. 12/676,453, filed Jul. 9, 2010, which is a 35 U.S.C. §371 national stage application of International Patent Application PCT/EP2008/061833 (published as WO 09/030774), filed Sep. 5, 2008, which claimed priority of European Patent Applications 07115743.2, filed Sep. 5, 2007 and 08101010.0, filed Jan. 28, 2008; this application further claims priority under 35 U.S.C. §119 of U.S. Provisional Application 60/971,932, filed Sep. 13, 2007 and 61/024,939, filed Jan. 31, 2008; the contents of which are incorporated herein by reference.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Feb. 15, 2013. The Sequence Listing is made up of 18 kilobytes, and the information contained in the attached "SEQUENCE LISTING" is identical to the information in the specification as originally filed. No new matter is added.

FIELD OF THE INVENTION

This invention relates to the field of therapeutic peptides, i.e. to new truncated Glucagon-Like Peptide-1 (GLP-1) analogues and derivatives thereof.

BACKGROUND OF THE INVENTION

A range of different approaches have been used for modifying the structure of glucagon-like peptide 1 (GLP-1) compounds in order to provide a longer duration of action in vivo.

WO 2006/097538, WO 2006/097536, WO 2006/037810, WO2006005667, WO 2005/027978. WO 98/08871 and US 2001/0011071 describes various GLP-1 analogues and derivatives thereof.

Runge et al (Journal of Biological Chemistry, vol. 283, no. 17, pp. 11340-11347), which was published after the priority dates of the present invention, discloses the crystal structure of the extracellular domain of the ligand-bound GLP-1 receptor.

Many diabetes patients particularly in the type 2 diabetes segment are subject to so-called "needle-phobia", i.e. a substantial fear of injecting themselves. In the type 2 diabetes segment most patients are treated with oral hypoglycaemic agents, and since GLP-1 compounds are expected to be an injectable pharmaceutical product these patients will be administered, the fear of injections may become a serious obstacle for the widespread use of the clinically very promising compounds. Thus, there is a need to develop new compounds which can be administered less than once daily, e.g. once every second or third day preferably once weekly, while retaining an acceptable clinical profile or optionally via non invasive administration such as pulmonary, nasal, sublingual, buccal or oral administration.

One object of the present invention is to provide a chemically, physically and enzymatically stable GLP-1 analogue or derivative thereof.

A further object of the invention is to provide a long acting, i.e. having an administration regimen as described above, GLP-1 analogue or derivative thereof.

Another object of this invention is to provide a GLP-1 analogue or derivative thereof with high potency (receptor affinity) in order to reduce the therapeutic dose used for example for once weekly s.c. dosing or alternatively for non-invasive delivery.

Another object of this invention is to provide a GLP-1 compound with a high binding affinity to the GLP-1 receptor (GLP-1R).

A still further object of this invention is to provide a GLP-1 compound with a high binding affinity to the extracellular domain of the GLP-1 receptor (nGLP-1R).

Another object of this invention is to provide a GLP-1 analogue or derivative thereof with high albumin binding affinity which protects the peptide for proteolytic degradation and reduce renal clearance of the peptide.

Potency, binding affinity to the GLP-1 receptor, and possibly also to the extracellular domain of the GLP-1 receptor are properties of potential relevance for an overall object of achieving long-acting, stable and of course therapeutically active GLP-1 derivatives with a potential for once weekly administration.

SUMMARY OF THE INVENTION

The invention relates to truncated analogues of GLP-1 (7-37), and derivatives thereof.

The invention relates to a GLP-1 analogue which is a modified GLP-1(7-35) (SEQ ID No 1) having: i) a total of 2, 3, 4, 5 6, 7, 8, or 9 amino acid substitutions as compared to GLP-1(7-35), including a) a Glu residue at a position equivalent to position 22 of GLP-1(7-35), and b) an Arg residue at a position equivalent to position 26 of GLP-1(7-35); or a derivative thereof.

The invention also relates to compositions and uses of these derivatives and analogues.

Optionally the amino acid(s) at a position equivalent to position 30, 31, 32, 33, 34, or 35 of GLP-1(7-35) can be absent provided that if the amino acid at position 30, 31, 32, 33 or 34 is absent then each amino acid residue downstream is also absent Also optionally, the GLP-1 analogue of the invention comprises a C-terminal amide group, or a C-terminal carboxylic acid group.

In a further aspect, pharmaceutical compositions and methods and uses of the analogues and derivatives according to the invention, is provided.

DESCRIPTION OF THE INVENTION

Definitions and Particular Embodiments

In the present specification, the following terms have the indicated meaning: The term "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g., γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The 22 proteogenic amino acids are: Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, Valine.

Thus a non-proteogenic (also designated non-natural) amino acid is a moiety which can be incorporated into a peptide via peptide bonds but is not a proteogenic amino acid. Examples are γ-carboxyglutamate, ornithine, phosphoserine, the D-amino acids such as D-alanine and D-glutamine, Synthetic non-proteogenic amino acids comprise amino acids manufactured by chemical synthesis, i.e. D-isomers of the amino acids encoded by the genetic code such as D-alanine and D-leucine, Aib (α-aminoisobutyric acid), Abu α-aminobutyric acid), Tle (tert-butylglycine), 3-aminomethyl benzoic acid, anthranilic acid, des-amino-Histidine, the beta analogs of amino acids such as β-alanine etc., D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid.

The term "analogue" as used herein referring to a polypeptide means a modified peptide wherein one or more amino acid residues of the peptide have been substituted by other amino acid residues and/or wherein one or more amino acid residues have been deleted from the peptide in the C-terminal of the peptide.

The term "modified peptide" as used herein refers to a modified peptide as defined above. For the present purposes this term is used interchangeably with the term "modified peptide sequence". Consistently herewith, the term "modification" when used herein in connection with peptide sequences refers to amino acid substitutions, additions, and/or deletions.

For the present purposes any amino acid substitution, deletion, and/or addition refers to the sequence of human GLP-1(7-35) which is included herein as SEQ ID No: 1. However, the numbering of the amino acid residues in the sequence listing always starts with no. 1, whereas for the present purpose we want, following the established practice in the art, to start with amino acid residue no. 7 and assign number 7 to it. Therefore, generally, any reference herein to a position number of the GLP-1(7-35) sequence is to the sequence starting with His at position 7 and ending with Gly at position 35.

A simple system is often used to describe analogues: For example [Arg$^{34}$]GLP-1(7-37)Lys designates a GLP-1(7-37) analogue wherein the naturally occurring lysine at position 34 has been substituted with arginine and wherein a lysine has been added to the terminal amino acid residue, i.e. to the Gly$^{37}$.

The expression "a position equivalent to" when used herein to characterize a modified GLP-1(7-35) sequence refers to the corresponding position in the natural GLP-1(7-35) sequence (having the sequence of SEQ ID No: 1). Corresponding positions are easily deduced, e.g. by simple handwriting and eyeballing. In the alternative, a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM50 and the default identity matrix may be used, and the penalty for the first residue in a gap may be set at −12 and the penalties for additional residues in a gap at −2.

All amino acids for which the optical isomer is not stated is to be understood to mean the L-isomer.

The term "each amino acid residue downstream" as used herein refers to each amino acid positioned towards the C-terminal relative to a specific amino acid. As an example Lys34 and Gly35 are each amino acid residues downstream of Val33 in GLP-1 (7-35).

In embodiments of the invention a maximum of 8 amino acids have been modified. In embodiments of the invention a maximum of 7 amino acids have been modified. In embodiments of the invention a maximum of 6 amino acids have been modified. In embodiments of the invention a maximum of 5 amino acids have been modified. In embodiments of the invention a maximum of 4 amino acids have been modified. In embodiments of the invention a maximum of 3 amino acids have been modified. In embodiments of the invention a maximum of 2 amino acids have been modified.

In embodiments of the invention, one or more amino acid(s) have been deleted in the C-terminal end.

In one aspect of the invention, the C-terminal of the analogue or derivative according to the invention may be terminated as either an acid or amide. In a preferred aspect, the C-terminal of the analogue or derivative of the invention is an amide.

In one aspect, the invention relates to a GLP-1 analogue or derivative thereof, wherein the amino acids at position 35, 36 and 37 are absent, and wherein the total length of the GLP-1 analogue is 28 amino acids. In a further aspect, the invention relates to a GLP-1 analogue or derivative thereof, wherein the amino acids at position 34, 35, 36 and 37 are absent, and wherein the total length of the GLP-1 analogue is 27 amino acids. In a further aspect, the invention relates to a GLP-1 analogue or derivative thereof, wherein the amino acids at position 33, 34, 35, 36 and 37 are absent, and wherein the total length of the GLP-1 analogue is 26 amino acids. In a further aspect, the invention relates to a GLP-1 analogue or derivative thereof, wherein the amino acids at position 32, 33, 34, 35, 36 and 37 are absent, and wherein the total length of the GLP-1 analogue is 25 amino acids. In a further aspect, the invention relates to a GLP-1 analogue or derivative thereof, wherein the amino acids at position 31, 32, 33, 34, 35, 36 and 37 are absent, and wherein the total length of the GLP-1 analogue is 24 amino acids. In a further aspect, the invention relates to a GLP-1 analogue or derivative thereof, wherein the amino acids at position 30, 31, 32, 33, 34, 35, 36 and 37 are absent, and wherein the total length of the GLP-1 analogue is 23 amino acids.

In one aspect, the invention relates to a GLP-1 analogue or derivative thereof having a C-terminal amide group.

In one aspect, the invention relates to a GLP-1 analogue or derivative thereof having 3 amino acid substitutions compared to the sequence 7-35 of SEQ ID NO 1 including the substitutions at position 22 and 26. In a further aspect, the invention relates to a GLP-1 analogue or derivative thereof, which has a substitution selected from the group of positions 7, 8, 18, 20, 23, 24, 25, 27, 30, 31, 33 and 34 compared to the sequence 7-35 of SEQ ID NO 1. In a further aspect, the invention relates to a GLP-1 analogue or derivative thereof, which has a substitution selected from the group consisting of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34 and Asn34. In a further aspect, the invention relates to a GLP-1 analogue or derivative thereof, which has a substitution selected from the group consisting of desaminoHis7, Aib8, Lys18, Lys20, Lys23, Glu30, Lys31, Lys33 and Lys34. In a further aspect, the invention relates to a GLP-1 analogue or derivative thereof, which has a substitution selected from the group consisting of desaminoHis7 and Aib8.

In one aspect, the invention relates to a GLP-1 analogue or derivative thereof having 4 amino acid substitutions compared to the sequence 7-35 of SEQ ID NO 1 including the substitutions at position 22 and 26. In a further aspect, the invention relates to a GLP-1 analogue or derivative thereof, which has two substitutions selected from the group of positions 7, 8, 18, 20, 23, 24, 25, 27, 30, 31, 33 and 34 compared to the sequence 7-35 of SEQ ID NO 1. In a further aspect, the invention relates to a GLP-1 analogue or derivative thereof, which has two substitutions selected from the group consisting of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34 and Asn34. In a further aspect, the invention relates to a GLP-1 analogue or derivative thereof having an amino acid substitution selected from the group consisting of desaminoHis7 and Aib8 and an amino acid substitution selected from the group consisting Lys18, Lys20, Lys23, Glu30, Lys31, Lys33 and Lys34. In a further aspect, the invention relates to a GLP-1 analogue or derivative thereof having an amino acid substitution selected from the group consisting desamino-His7 and Aib8, and an amino acid substitution selected from the group consisting Lys18, Lys20, Lys23, Glu30, Lys31, Lys33 and Lys34.

In a one aspect, the invention relates to a GLP-1 analogue or derivative thereof having 5 amino acid substitutions compared to the sequence 7-35 of SEQ ID NO 1 including the substitutions at position 22 and 26. In a further aspect, the invention relates to a GLP-1 analogue or derivative thereof, which has three amino acid substitutions selected from the group of positions 7, 8, 18, 20, 23, 24, 25, 27, 30, 31, 33 and 34 compared to the sequence 7-35 of SEQ ID NO 1. In a further aspect, the invention relates to a GLP-1 analogue or derivative thereof, which has three amino acid substitutions selected from the group of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34 and Asn34. In a further aspect, the invention relates to a GLP-1 analogue or derivative thereof having an amino acid substitution selected from the group consisting of desaminoHis7 and Aib8, and two amino acid substitutions selected from the group consisting of Lys18, Lys20, Lys23, Glu30, Lys31, Lys33 and Lys34. In a further aspect, the invention relates to a GLP-1 analogue or derivative thereof having an amino acid substitution selected from the group consisting of desaminoHis7 and Aib8, and two amino acid substitutions selected from the group consisting of Lys18, Lys20, Lys23, Glu30, Lys31, Lys33 and Lys34.

In one aspect, the invention relates to a GLP-1 analogue or derivative thereof having 6, 7 or 8 amino acid substitutions compared to the sequence 7-35 of SEQ ID NO 1 including the substitutions at position 22 and 26. In a further aspect, the invention relates to a GLP-1 analogue or derivative thereof, which has four, five or six amino acid substitutions selected from the group of positions 7, 8, 18, 20, 23, 24, 25, 27, 30, 31, 33 and 34. In a further aspect, the invention relates to a GLP-1 analogue or derivative thereof, which has four, five or six amino acid substitutions selected from the group consisting of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34 and Asn34. In a further aspect, the invention relates to a GLP-1 analogue or derivative thereof having an amino acid substitution selected from the group consisting of desamino-His7 and Aib8 and three, four or five amino acid substitutions selected from the group consisting of Lys18, Lys20, Lys23, Glu30, Lys31, Lys33 and Lys34. In a further aspect, the invention relates to a GLP-1 analogue or derivative thereof having an amino acid substitution selected from the group consisting of desaminoHis7 and Aib8 and three, four or five amino acid substitutions selected from the group consisting of Lys18, Lys20, Lys23, Glu30, Lys31, Lys33 and Lys34.

In one aspect, the invention relates to a GLP-1 analogue or derivative thereof having the sequence of formula (I)

```
Formula (I)
                                          (SEQ ID No: 2)
Xaa7-Xaa8-Xaa9-Gly-Thr-Phe-Thr-Ser-Asp-Xaa16-Ser- Xaa18-Tyr-Xaa20-Glu-Glu-Xaa23-Xaa24-Xaa25-Arg- Xaa27-Phe-Ile-Xaa30-Xaa31-Leu-Xaa33-Xaa34-Xaa35-R
``` wherein $Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_9$ is Glu or a Glu derivative such as alpha, alpha dimethyl-Glu;

$Xaa_{16}$ is Val or Leu;

$Xaa_{18}$ is Ser, Lys, Cys or Arg;

$Xaa_{20}$ is Leu, Lys or Cys;

$Xaa_{23}$ is Gln, Glu, Lys, Cys or Arg;

$Xaa_{24}$ is Ala or Asn;

$Xaa_{25}$ is Ala or Val;

$Xaa_{27}$ is Glu, Ala or Leu;

$Xaa_{30}$ is Ala, Glu, Lys, Arg or absent;

$Xaa_{31}$ is Trp, Lys, Cys or absent;

$Xaa_{33}$ is Val, Lys, Cys or absent;

$Xaa_{34}$ is Lys, Glu, Asn, Arg, Cys or absent;

$Xaa_{35}$ is Gly, Aib or absent;

R is amide or is absent;

provided that if $Xaa_{30}$, $Xaa_{31}$, $Xaa_{32}$, $Xaa_{33}$, or $Xaa_{34}$ is absent then each amino acid residue downstream is also absent.

In another aspect, the invention relates to a GLP-1 analogue or derivative thereof having the sequence of formula (II)

```
Formula (II)
                                          (SEQ ID No: 3)
Xaa7-Xaa8-Glu-Gly-Thr-Phe-Thr-Ser-Asp-Val-Ser- Xaa18-Tyr-Leu-Glu-Glu-Gln-Ala-Ala-Arg-Glu-Phe- Ile-Xaa30-Trp-Leu-Xaa33-Xaa34-Xaa35-R
``` wherein
Xaa$_7$ is L-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine;
Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{18}$ is Ser, Lys or Arg;
Xaa$_{30}$ is Ala, Glu, Lys, Arg or is absent;
Xaa$_{33}$ is Val, Lys or absent;
Xaa$_{34}$ is Lys, Glu, Arg or is absent;
Xaa$_{35}$ is Gly, Aib or is absent;
R is amide or is absent.

In one aspect of the invention, R is absent. In a further aspect of the invention, Xaa$_{35}$ and R are absent. In a further aspect of the invention, Xaa$_{34}$, Xaa$_{35}$ and R are absent. In a further aspect of the invention, Xaa$_{33}$, Xaa$_{34}$, Xaa$_{35}$ and R are absent. In a further aspect of the invention, Xaa$_{30}$, Xaa$_{33}$, Xaa$_{34}$, Xaa$_{35}$ and R are absent.

The term "derivative" as used herein in relation to a peptide means a chemically modified peptide or an analogue thereof, wherein at least one substituent is not present in the unmodified peptide or an analogue thereof, i.e. a peptide which has been covalently modified.

Typical modifications are amides, carbohydrates, alkyl groups, acyl groups, esters and the like. An example of a derivative according to the invention is N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8, Lys20, Glu22, Val25, Arg26, Leu27, Glu30, Lys33)GLP-1(7-33)amide (structure 1) wherein the naturally occurring Tyr at position 20 has been substituted with lysine which has been derivatised at N-epsilon20 with epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl} and wherein the naturally occurring alanine at position 8 has been substituted with Aib and glycine in pos 22 with glutamate and alanine at position 25 with valine and lysine at position 26 with arginine and glutamate at position 27 with leucine and alanine at position 30 with glutamate and valine at position 33 with lysineamide.

In one aspect of the invention, a GLP-1 analogue or derivative thereof, which is derivatised with an albumin binding residue or is pegylated, is provided.

In one aspect, the invention relates to a GLP-1 analogue or derivative, wherein the amino acid which is pegylated or derivatised with an albumin binding residue is a Lys-residue or a Cys-residue. In one aspect, the amino acid which is pegylated or derivatised with an albumin binding residue is a Lys-residue. In one aspect, the amino acid which is pegylated or derivatised with an albumin binding residue is a Cys-residue. In one aspect, the C-terminal amino acid is pegylated or derivatised with an albumin binding residue. In one aspect, the invention relates to a GLP-1 analogue or derivative thereof pegylated or derivatised with an albumin binding residue at position 18, 20, 23, 31, 33, 34 or at the C-terminal amino acid. In a further aspect, the invention relates to a GLP-1 analogue or derivative pegylated or derivatised with an albumin binding residue at position 18. In further aspect, the invention relates to a GLP-1 analogue or derivative thereof pegylated or derivatised with an albumin binding residue at position 20. In a further aspect, the invention relates to a GLP-1 analogue or derivative thereof pegylated or derivatised with an albumin binding residue at position 23. In further aspect, the invention relates to a GLP-1 analogue or derivative thereof pegylated or derivatised with an albumin binding residue at position 31. In a further aspect, the invention relates to a GLP-1 analogue or derivative thereof pegylated or derivatised with an albumin binding residue at position 33. In a further aspect, the invention relates to a GLP-1 analogue or derivative thereof pegylated or derivatised with an albumin binding residue at position 34.

In one aspect, the invention relates to a GLP-1 analogue or derivative thereof, which has been derivatised with an albumin binding residue.

The term "derivatised" as used herein means chemically connected via a covalent bond. For example a lysine residue or cysteine residue is linked to an albumin binding residue via a chemical bond. Such a chemical bond can as an example be obtained by derivatisation of an epsilon amino group of lysine by acylation with an active ester of an albumin binding residue such as a long fatty acid.

Other examples of connecting two chemical moieties as used in the present invention includes but is not limited to alkylation, ester formation, amide formation or maleimide coupling.

Structure 1

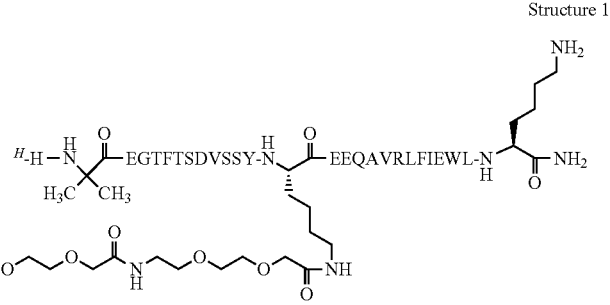

The term "linker" as used herein means a spacer (the two terms spacer and linker is used interchangeably in the present specification) that separates a peptide and an albumin binding residue or a polyethylene glycol polymer.

In one aspect of the invention, the linker comprises one or more alkylene glycol units, such as 1 to 5 alkylene glycol units. The alkylene glycol units are in a further aspect ethylene glycol, propylene glycol or butylene glycol but can also be higher alkylene glycols.

In another aspect of the invention, the linker is a hydrophilic linker selected from —(CH$_2$)$_l$D[(CH$_2$)$_n$E]$_m$(CH$_2$)$_p$-Q$_q$-, wherein l, m and n independently are 1-20 and p is 0-10, Q is —Z—(CH$_2$)$_l$D[(CH$_2$)$_n$G]$_m$(CH$_2$)$_p$—, q is an integer in the range from 0 to 5,
each D, E, and G are independently selected from —O—, —NR$^3$—, —N(COR$^4$)—, —PR$^5$(O)—, and —P(OR$^6$)(O)—, wherein R$^3$, R$^4$, R$^5$, and R$^6$ independently represent hydrogen or C$_{1-6}$-alkyl,
Z is selected from —C(O)NH—, —C(O)NHCH$_2$—, —OC(O)NH—, —C(O)NHCH$_2$CH$_2$—, —C(O)CH$_2$—, —C(O)CH═CH—, —(CH$_2$)$_s$—, —C(O)—, —C(O)O— or —NHC(O)—, wherein s is 0 or 1.

In another aspect of the invention, the linker is a hydrophilic linker as defined above wherein l is 1 or 2, n and m are independently 1-10 and p is 0-10.

In another aspect of the invention, the linker is a hydrophilic linker as defined above wherein D is —O—.

In a further aspect of the invention, the linker is a hydrophilic linker as defined above wherein E is —O—.

In yet another aspect of the invention, the hydrophilic linker is
—CH$_2$O[(CH$_2$)$_2$O]$_m$(CH$_2$)$_p$Q$_q$-, wherein m is 1-10, p is 1-3, and Q is —Z—CH$_2$O[(CH$_2$)$_2$O]$_m$(CH$_2$)$_p$— wherein Z is as defined above.

In another aspect of the invention, the linker is a hydrophilic linker as defined above wherein q is 1.

In another aspect of the invention, the linker is a hydrophilic linker as defined above wherein G is —O—.

In another aspect of the invention, the linker is a hydrophilic linker as defined above wherein Z is selected from the group consisting of —C(O)NH—, —C(O)NHCH$_2$—, and —OC(O)NH—.

In another aspect of the invention, the linker is a hydrophilic linker as defined above wherein q is 0.

In another aspect of the invention, the linker is a hydrophilic linker as defined above wherein l is 2.

In another aspect of the invention, the linker is a hydrophilic linker as defined above wherein n is 2.

In one aspect of this invention a "hydrophilic linker" is used that separates a peptide and an albumin binding residue with a chemical moiety.

In one aspect of this invention, the hydrophilic linker is
—C(O)—(CH$_2$)$_l$—O—[(CH$_2$CH$_2$—O]$_m$—(CH$_2$)$_p$—[NHC(O)—(CH$_2$)$_l$—O—[(CH$_2$)$_n$—O]$_m$—(CH$_2$)$_p$]$_q$—NH—,
wherein l, m, n, and p independently are 1-5, and q is 0-5.

In yet another aspect of this invention, the hydrophilic linker is —C(O)—CH$_2$—O—CH$_2$CH$_2$—O—CH$_2$CH$_2$[NHC(O)—CH$_2$—O—CH$_2$CH$_2$O—CH$_2$CH$_2$]$_q$—NH—, wherein q is 0-5.

In yet another aspect of this invention, the hydrophilic linker is —C(O)—CH$_2$—O—CH$_2$CH$_2$—O—CH$_2$CH$_2$—NHC(O)—CH$_2$—O—CH$_2$CH$_2$O—CH$_2$CH$_2$—NH—.

In yet another aspect of the invention, the hydrophilic linker is —[CH$_2$CH$_2$O]$_{m+1}$(CH$_2$)$_p$Q$_q$-
wherein m and p independently is 0-10, and
Q is —Z—(CH$_2$)$_l$D[(CH$_2$)$_n$G]$_m$(CH$_2$)$_p$— as defined above.

In yet another aspect of the invention, the hydrophilic linker is —(CH$_2$)$_l$—O—[(CH$_2$)$_n$—O]$_m$—(CH$_2$)$_p$—[C(O)NH—(CH$_2$)$_l$—O—[(CH$_2$)$_n$—O]$_m$—(CH$_2$)$_p$]$_q$—,
wherein l, m, n, and p independently are 1-5, and q is 0-5.

In a further aspect of the invention, the linker comprises an amino acid residue except Cys, or a dipeptide such as Gly-Lys. In the present text, the expression "a dipeptide such as Gly-Lys" is used to designate a dipeptide wherein the C-terminal amino acid residue is Lys, His or Trp, preferably Lys, and wherein the N-terminal amino acid residue is selected from the group comprising Ala, Arg, Asp, Asn, Gly, Glu, Gln, Ile, Leu, Val, Phe and Pro.] Suitable PEG polymers are typically commercially available or may be made by techniques well-known to those skilled in the art.

In one aspect of the invention, the PEG polymer has a molecular weight of greater than 700 D, in a further aspect a molecular weight greater than 5 kD, in yet a further aspect greater than 10 kD, and in a even further aspect greater that 20 kD. The PEG polymer may be linear or branched. In cases where the PEG polymer is greater than 20 KDa, the PEG polymer is preferable having a branched structure, such as for example, a 43 kD branched PEG-peptide (Shearwater 2001 catalog #2D3XOT01, mPEG2-MAL).

The attachment of a PEG on an intact peptide can be accomplished by attaching the PEG on the opposite side of the peptide surface that interacts with the receptor.

There are several strategies for coupling PEG to peptides (see, e.g. Veronese, Biomaterials 22:405-417, 2001), all of which are incorporated herein by reference in their entirety. Those skilled in the art, will therefore be able to utilize well-known techniques for linking the PEG polymer to human amylin or the amylin analogs described herein.

Briefly, cysteine PEGylation is one method for site-specific PEGylation, and can be accomplished by introducing a unique cysteine mutation at one of the specific positions on human amylin or the amylin analog and then reacting the resulting peptide with a cysteine-specific PEGylation reagent, such as PEG-maleimide. It may be necessary to mutate the peptide in order to allow for site-specific PEGylation. For example, if the peptide contains cysteine residues, these will need to be substituted with conservative amino acids in order to ensure site-specific PEGylation. In addition, rigid linkers, including but not limited to "GGS", "GGSGGS", and "PPPS" may be added to the C-terminus, but before the site of PEG attachment (i.e. a unique cysteine residue).

In one aspect of the invention, the albumin binding residue is a lipophilic residue. In a further aspect, the lipophilic residue is attached to a lysine residue optionally via a linker by conjugation chemistry such as by alkylation, acylation, ester formation, or amide formation or to a cysteine residue by maleimide coupling.

In a further aspect of the invention, the albumin binding residue is negatively charged at physiological pH. In another aspect of the invention, the albumin binding residue comprises a group which can be negatively charged. One preferred group which can be negatively charged is a carboxylic acid group.

In yet another aspect of the invention, the albumin binding residue is selected from the group consisting of a straight chain alkyl group, a branched alkyl group, a group which has an w-carboxylic acid group, and a partially or completely hydrogenated cyclopentanophenanthrene skeleton.

In a further aspect of the invention, the albumin binding residue is a cibacronyl residue.

In a further aspect of the invention, the albumin binding residue has from 6 to 40 carbon atoms, from 8 to 26 carbon atoms or from 8 to 20 carbon atoms.

In a further aspect of the invention, the albumin binding residue is an acyl group selected from the group comprising CH$_3$(CH$_2$)$_r$CO—, wherein r is an integer from 4 to 38, preferably an integer from 4 to 24, more preferred selected from the group comprising CH$_3$(CH$_2$)$_6$CO—, CH$_3$(CH$_2$)$_8$CO—, CH$_3$(CH$_2$)$_{10}$CO—, CH$_3$(CH$_2$)$_{12}$CO—, CH$_3$(CH$_2$)$_{14}$ CO—, CH$_3$(CH$_2$)$_{16}$CO—, CH$_3$(CH$_2$)$_{18}$CO—, CH$_3$(CH$_2$)$_{20}$CO— and CH$_3$(CH$_2$)$_{22}$CO—.

In another aspect of the invention, the albumin binding residue is an acyl group of a straight-chain or branched alkane α,ω-dicarboxylic acid.

In one aspect, the invention relates to a GLP-1 analogue or derivative thereof, wherein at least one amino acid residue is derivatised with A-B-C-D- wherein A- is selected from the group consisting of

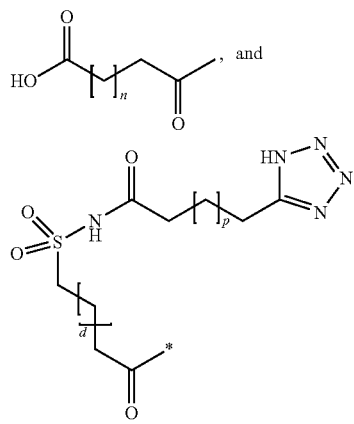

wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, -B- is selected from the group consisting of

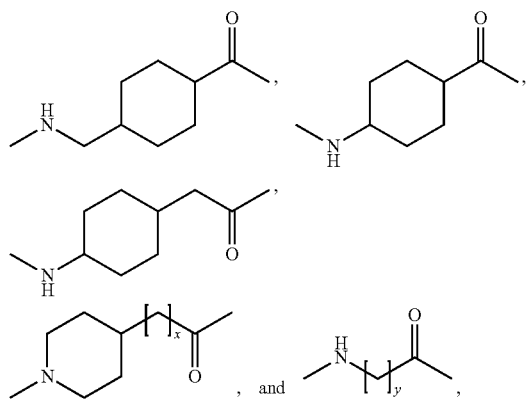

wherein x is selected from the group consisting of 0, 1, 2, 3 and 4, and y is selected from the group consisting of 1, 2, 3, 4, 5, 6, 7, 8, 9, 10, 11 and 12, -C- is selected from the group consisting of

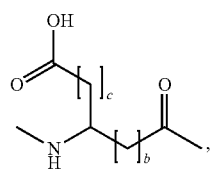

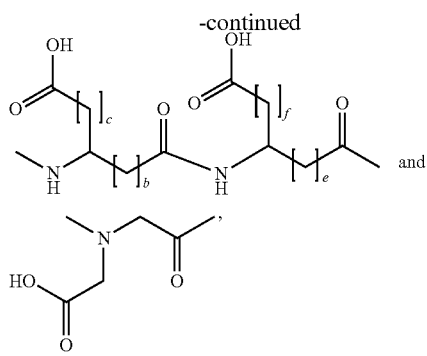

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker.

In one aspect of the invention, one amino acid residue of the analogue according to the invention is derivatised with A-B-C-D-.

In one aspect, the derivatised amino acid residue comprises an amino group. In a further aspect, the derivatised amino acid residue comprises a primary amino group in a side chain. In yet a further aspect, the derivatised amino acid residue is lysine.

In one aspect, A- is

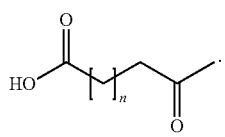

In one aspect, n is selected from the group consisting of 15 and 17, and more is preferred 17.

In one aspect, A- is

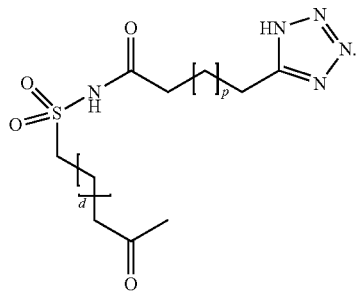

In one aspect, p is selected from the group consisting of 12, 13, and 14 and more preferred is 13. In one aspect, d is selected from the group consisting of 0, 1, 2, 3 and 4, more preferred 0, 1 and 2 and most preferred 1. In one aspect, d is selected from the group consisting of 0, 1 and 2 and p is selected from the group consisting of 12, 13 or 14, more preferred d is selected from the group consisting of 1 and 2 and p is selected from the group consisting of 13 and 14, and most preferred d is 1 and p is 13.

In one aspect, -B- is

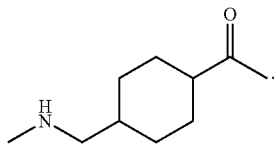

In one aspect, -B- is

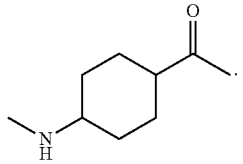

In one aspect, -B- is

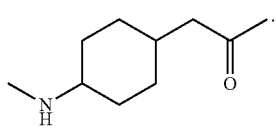

In one aspect, -B- is

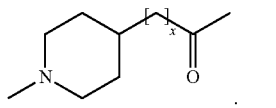

In one aspect, x is selected from the group consisting of 0, 1 and 2, more preferred x is selected from the group consisting of 0 and 1 and most preferred x is 1.

In one aspect, -B- is

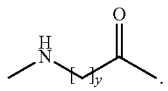

In one aspect, y is selected from the group consisting of 2, 3, 4, 5, 6, 7, 8, 9 and 10 and more preferred y is selected from the group consisting of 2, 3, 4, 5, 6, 7, and 8.

In one aspect, -C- is

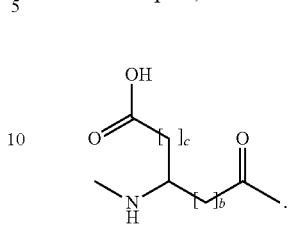

In one aspect, c is selected from the group consisting of 0 and 1 and b is selected from the group consisting of 1 and 2, more preferred b is 1 and c is 0.

In one aspect, -C- is

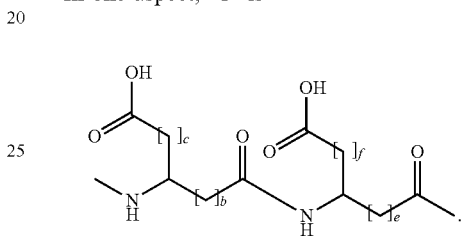

In one aspect, f is selected from the group consisting of 0 and 1 and e is selected from the group consisting of 1 and 2, more preferred e is 1 and f is 0.

In one aspect, -C- is

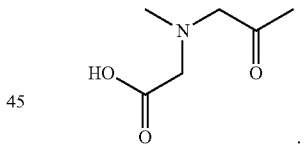

In one aspect, D is selected from the group consisting of

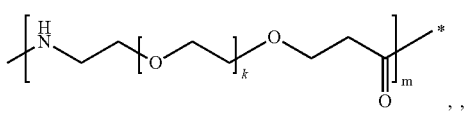,

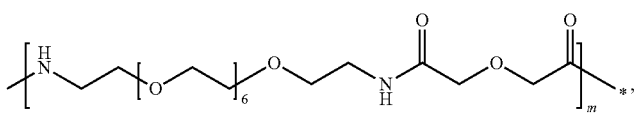,

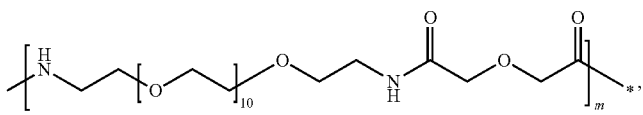,

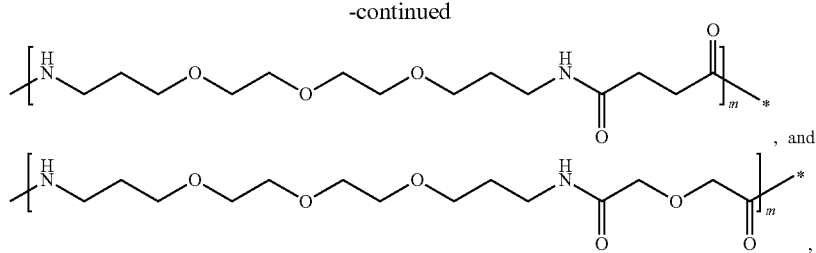

, and and wherein k is selected from the group consisting of 0, 1, 2, 3, 4, 5, 11 and 27, and m is selected from the group consisting of 0, 1, 2, 3, 4, 5 and 6.

In one aspect, -D- is

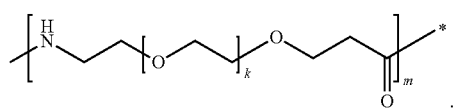

In one aspect, k is selected from the group consisting of 1, 2, 3, 11 and 27 and more preferred k is 1. In one aspect, m is selected from the group consisting of 0, 1, 2, 3, and 4 and more preferred m is selected from the group consisting of 0, 1 and 2.

In one aspect, -D- is

In one aspect, -D- is

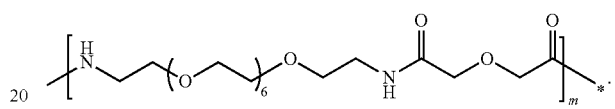

In one aspect, -D- is

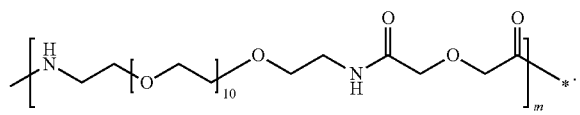

In one aspect, -D- is

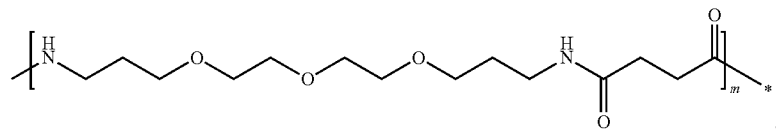

In one aspect, -D- is

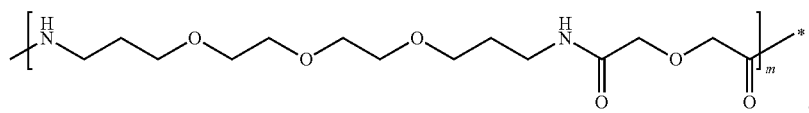

In one aspect, m is selected from the group consisting of 0, 1, 2, 3, and 4 and more preferred m is selected from the group consisting of 0, 1 and 2.

In one aspect, A-B-C-D- is selected and combined from

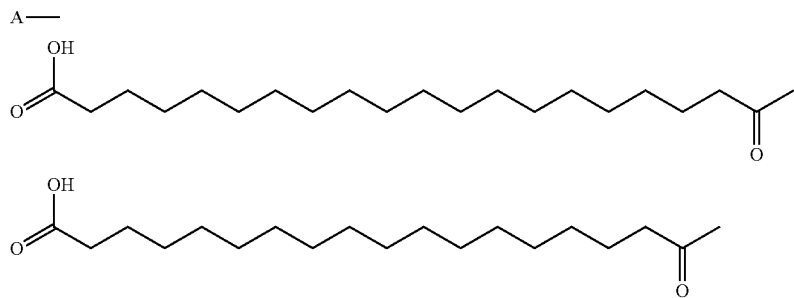

-continued
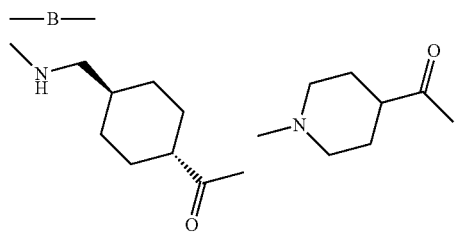
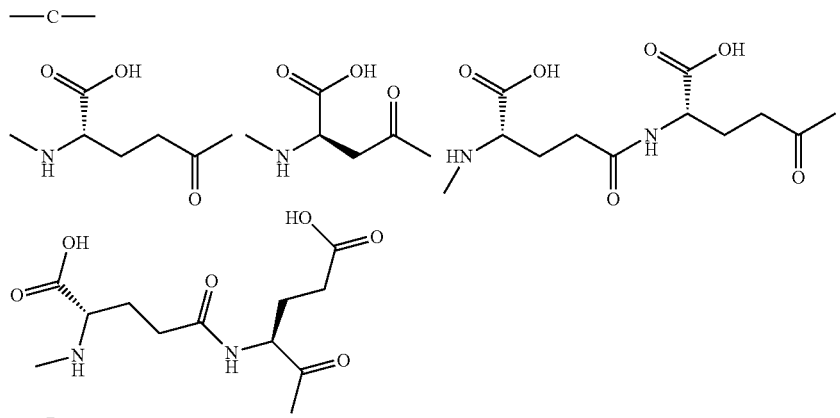
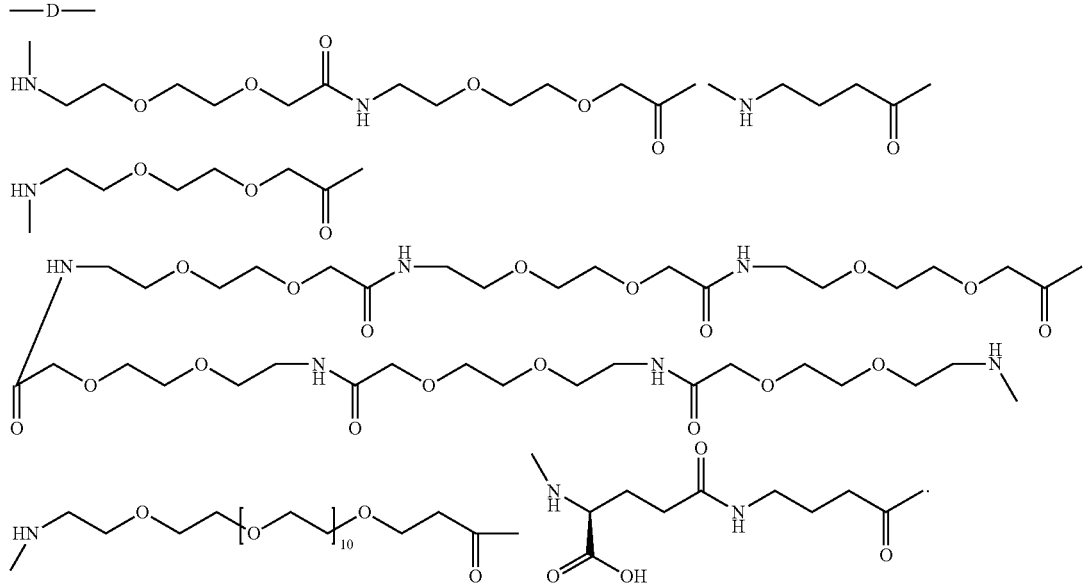
In one aspect, A-B-C-D- is selected and combined from
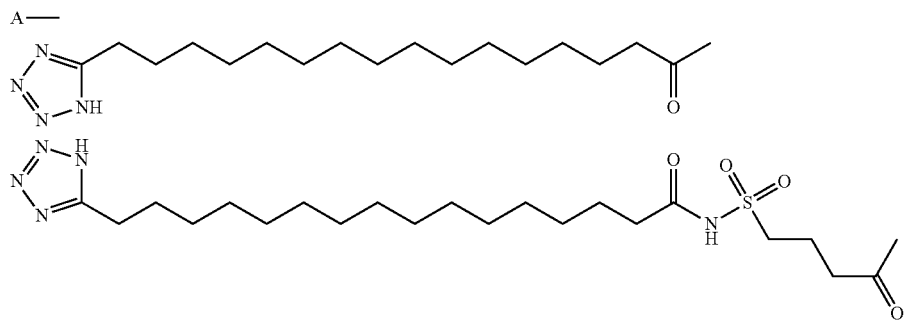

-continued
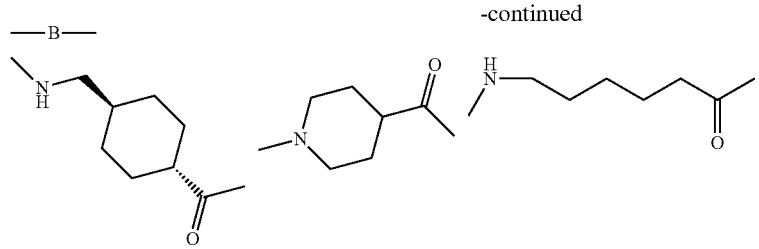
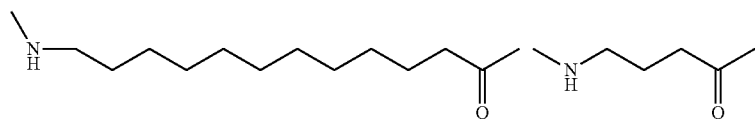
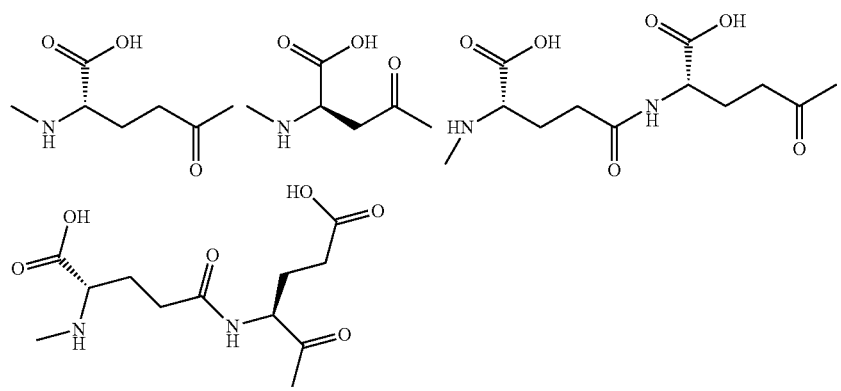
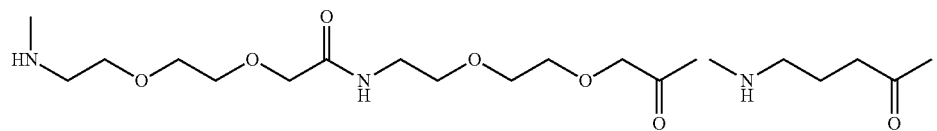
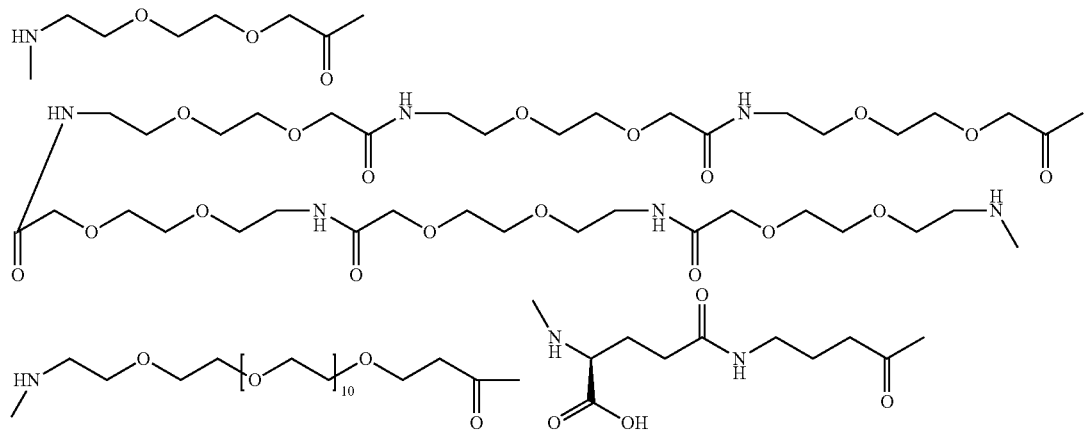
In one aspect, A-B-C-D- is selected from the group consisting of

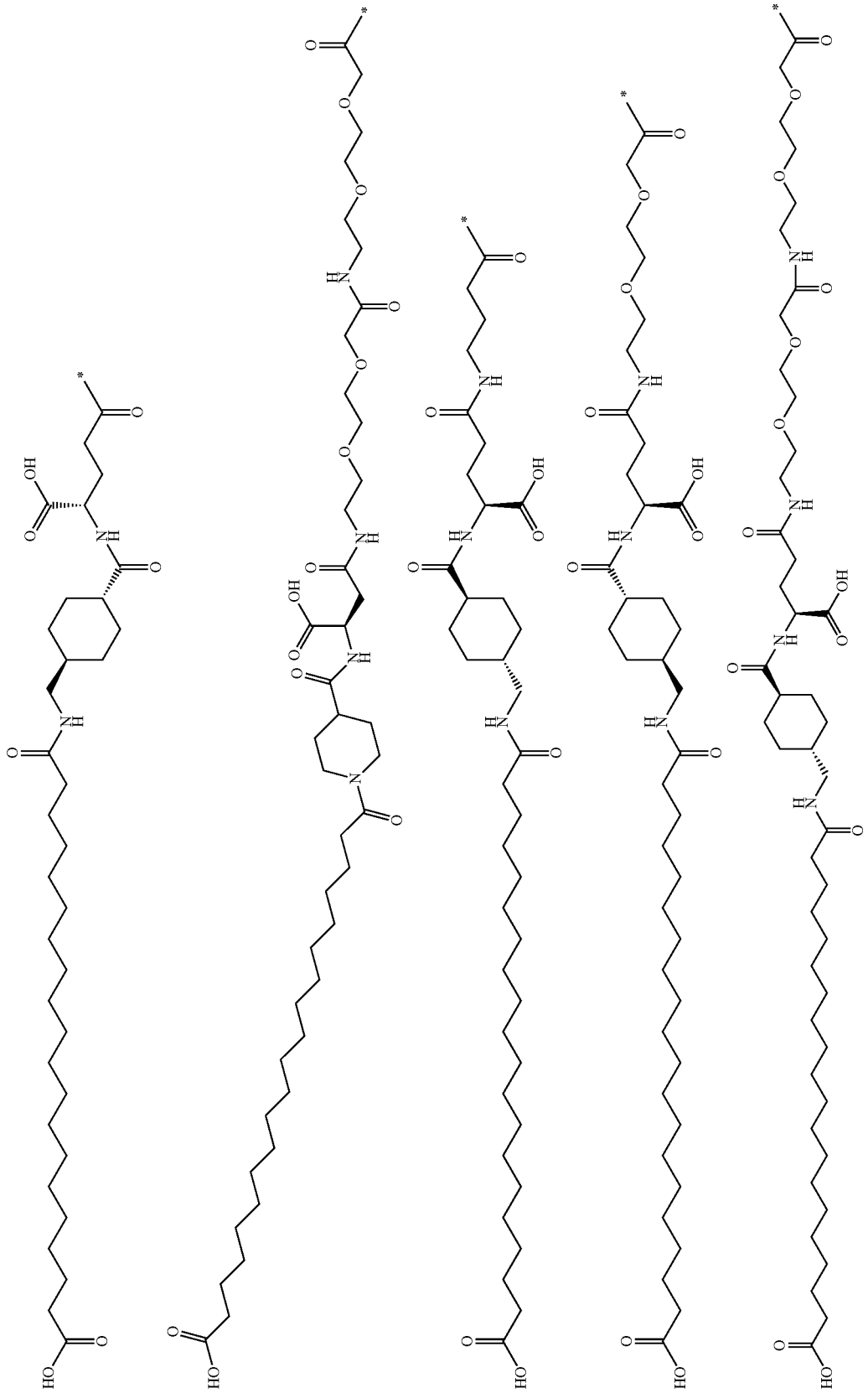

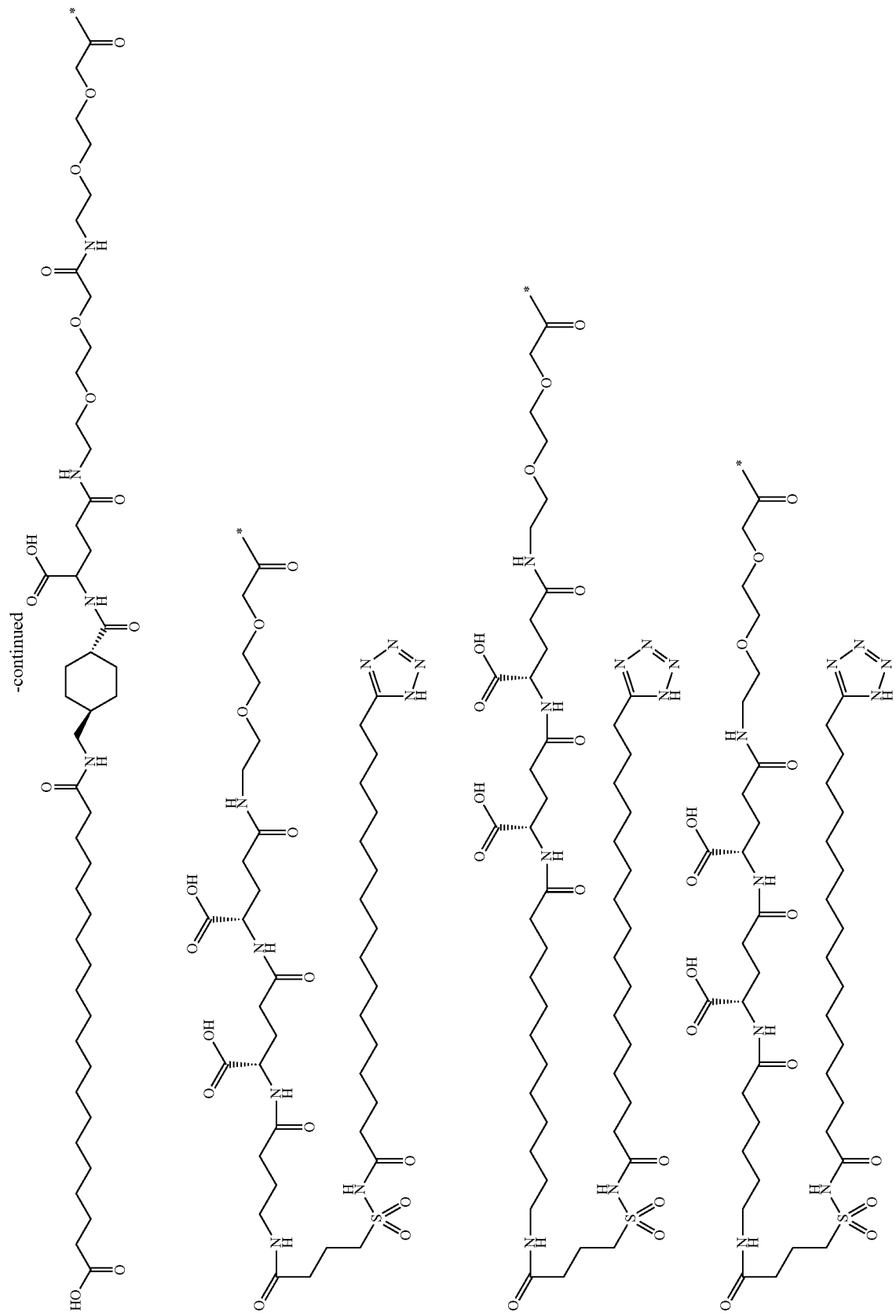
-continued 25
26
-continued
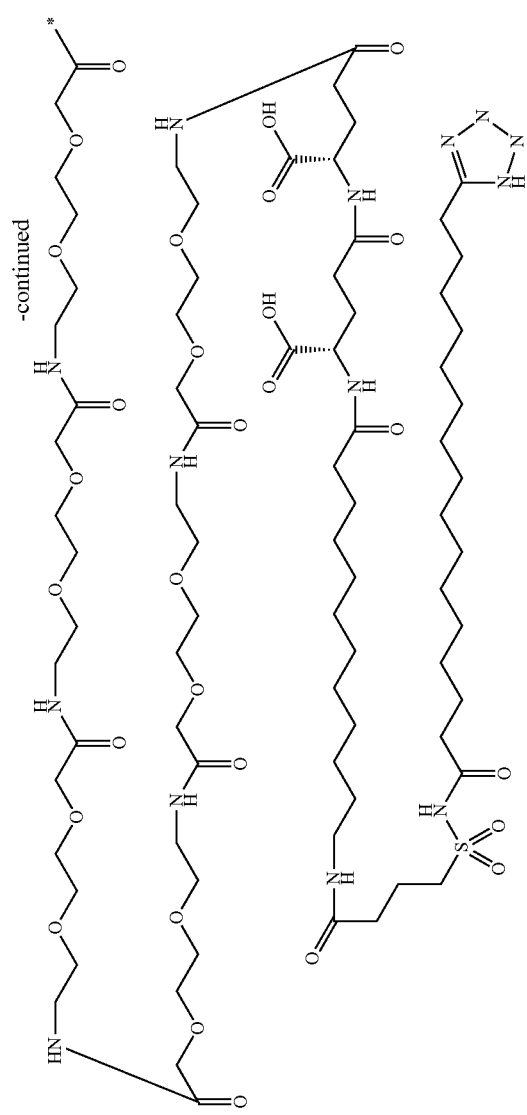
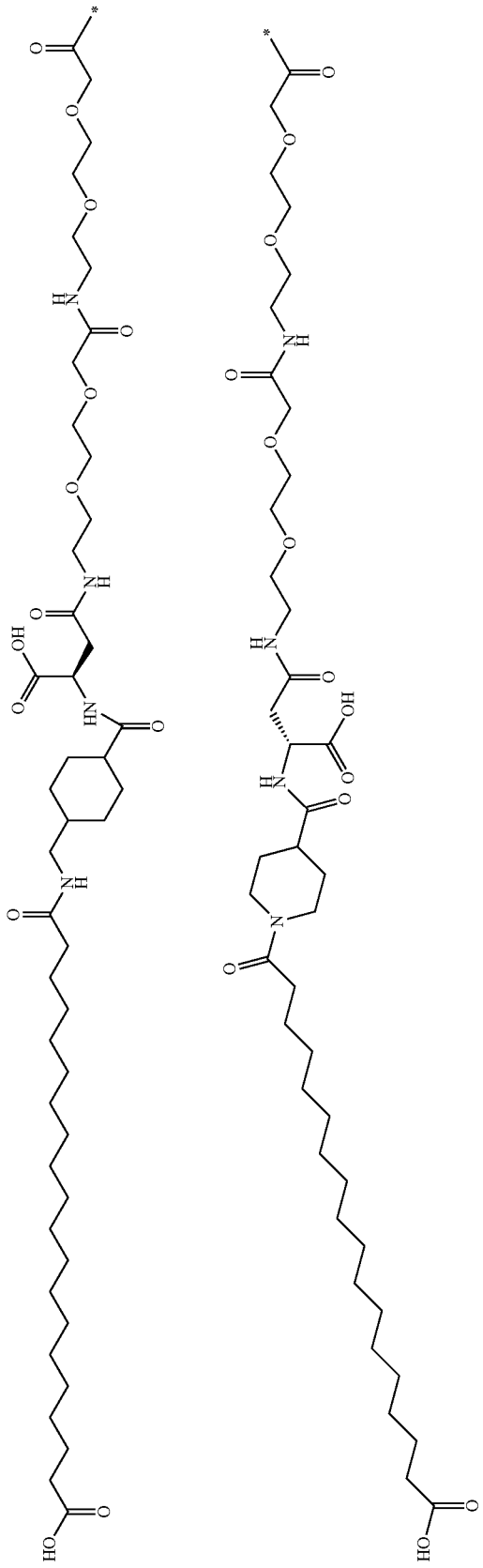

-continued
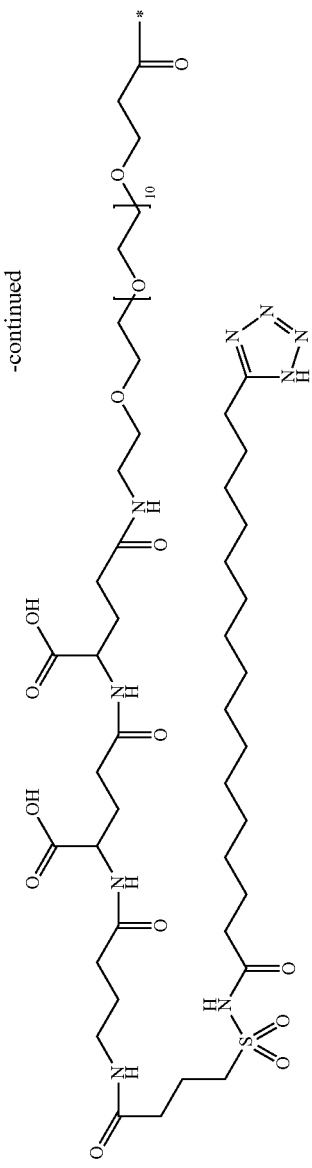
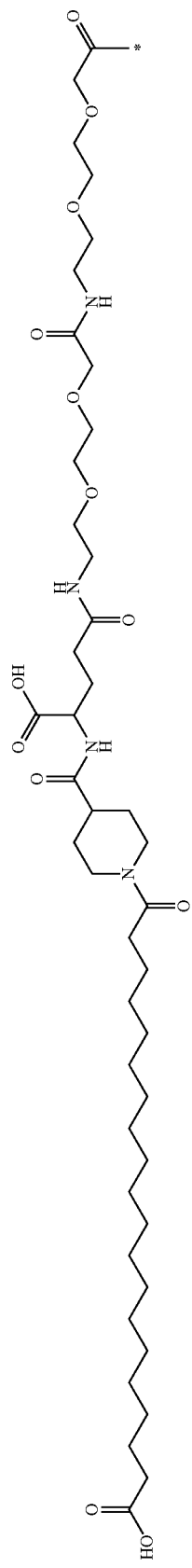
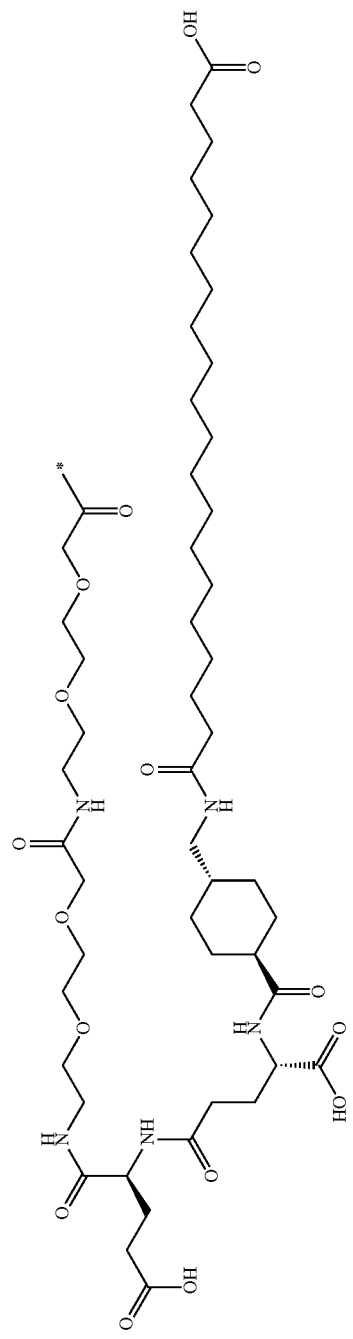

In one aspect, the invention relates to a GLP-1 analogue or derivative thereof, wherein at least one amino acid residue is derivatised with A-B-C-D-, and where the derivative binds to albumin.

In one aspect, A-B-C-D is composed of an albumin binding fragment A-B-C- and a hydrophilic linker D.

The term "GLP-1 peptide" as used herein means GLP-1 (7-35) (SEQ ID No 1) or a GLP-1(7-35) analogue thereof.

In one embodiment the GLP-1 analogue or derivative thereof according to the invention is an insulinotropic agent.

In the aspect of the invention, wherein the analogue is derivatised any amino acid position in the GLP-1 analogue may be derivatised. In one aspect of the invention, the amino acid residue which is derivatised comprises an amino group. Examples of amino acid residues comprising an amino group is lysine, ornithine, Epsilon-N-alkylated lysine such as Epsilon-N methylLysine, O-aminoethylserine, O-aminopropylserine or longer O alkylated serines containing a primary or secondary amino group in the side chain.

In a further aspect of the invention, the derivatised amino acid residue comprises a primary amino group in a side chain. Examples of amino acid residues comprising a primary amino group is lysine ornithine, O-aminoethylserine, O-aminopropylserine or longer O alkylated serines containing a primary amino group in the side chain.

In yet a further aspect of the invention, the derivatised amino acid residue is lysine. In yet a further aspect of the invention, the derivative according to the invention is only derivatised in one position, e.g. only one amino acid residue is derivatised.

In another aspect of this invention, the amino acid residue which is derivatised is cysteine.

Functional Properties

A number of GLP-1 compounds of the invention have been synthesized and tested as described in the experimental part.

The GLP-1 compounds of the invention have several advantageous and beneficial properties as explained in the following, by reference to the Examples.

The term "insulinotropic agent" as used herein means a GLP-1 analogue or derivative thereof which is an agonist of the human GLP-1 receptor, i.e. a GLP-1 analogue or derivative thereof which stimulates the formation of cAMP in a suitable medium containing the human GLP-1 receptor (one such medium disclosed below).

In a first aspect, the GLP-1 analogue or derivative of the invention has an acceptable, preferably high potency (at the receptor).

The potency of an insulinotropic agent such as the GLP-1 compounds of the invention may be determined by calculating the $EC_{50}$ value from the dose-response curve, e.g. as described in Example 21.

In particular embodiments (i) baby hamster kidney (BHK) cells expressing the cloned human GLP-1 receptor are used, preferably BHK-467-12A, more preferably BHK-467-12A (tk-ts13); (ii) the cells are grown in DMEM media with the addition of 100 IU/mL penicillin, 100 μg/mL streptomycin, 5% fetal calf serum and 0.5 mg/mL Geneticin G-418 (Life Technologies), preferably at 5% CO2; (iii) the cells, preferably at approximately 80% confluence, are washed twice in phosphate buffered saline; (iv) the cells are harvested with an aqueous solution of tetrasodium salt of ethylenediaminetetraacetic acid, such as Versene; (v) plasma membranes are prepared from the cells by homogenisation, preferably in buffer 1; the homogenate is centrifuged, e.g. at 48,000×g for 15 min at 4° C.; and/or (vii) the pellet is suspended by homogenization in buffer 2. Steps (vi) and (vii) are preferably repeated, e.g. one or two times more.

The functional receptor assay may be carried out as described in Example 21 by measuring cyclic AMP (cAMP) as a response to stimulation by the insulinotropic agent. cAMP formed is preferably quantified by the AlphaScreen™ cAMP Kit (Perkin Elmer Life Sciences). Incubations may be carried out in half-area 96-well microtiter plates in a total volume of 50 μL buffer 3 (50 mM Tris-HCl, 5 mM HEPES, 10 mM $MgCl_2$, pH 7.4) and with the following additions: 1 mM ATP, 1 μM GTP, 0.5 mM 3-isobutyl-1-methylxanthine (IBMX), 0.01% Tween-20, 0.1% BSA, 6 μg membrane preparation, 15 μg/mL acceptor beads, 20 μg/mL donor beads preincubated with 6 nM biotinyl-cAMP. Analogues or derivatives to be tested for agonist activity are preferably dissolved and diluted in buffer 3. GTP is freshly prepared for each experiment. The plate is incubated in the dark with slow agitation for three hours at room temperature followed by counting in the Fusion™ instrument (Perkin Elmer Life Sciences). Concentration-response curves are plotted for the individual analogues or derivatives and $EC_{50}$ values estimated using a four-parameter logistic model with Prism v. 4.0, or 5.0 (GraphPad, Carlsbad, Calif.).

In a first particular embodiment, the GLP-1 derivative of the invention has a potency ($EC_{50}$ in nM), as determined using the cAMP assay, below 10.00, preferably below 9.00, more preferably below 8.00, even more preferably below 7.00, and most preferably below 6.00 (nM).

In a second particular embodiment, the GLP-1 derivative of the invention has a potency ($EC_{50}$ in nM), as determined using the cAMP assay, below 5.00, preferably below 4.00, more preferably below 3.00, even more preferably below 2.00, and most preferably below 1.00 (nM).

In a third particular embodiment, the GLP-1 derivative of the invention has a potency ($EC_{50}$ in nM), as determined using the cAMP assay, below 0.80, preferably below 0.60, more preferably below 0.40, even more preferably below 0.20, and most preferably below 0.10 (nM).

In a fourth particular embodiment, the GLP-1 derivative of the invention has a potency ($EC_{50}$ in nM), as determined using the cAMP assay, below 0.090, preferably below 0.080, more preferably below 0.070, even more preferably below 0.060, and most preferably below 0.050 (nM).

In a fifth particular embodiment, the GLP-1 derivative of the invention has a potency ($EC_{50}$ in nM), as determined using the cAMP assay, below 0.040, preferably below 0.030, more preferably below 0.020, and most preferably below 0.010 (nM).

Accordingly, exemplary ranges of potency ($EC_{50}$ in nM, as determined using the cAMP assay) of GLP-1 derivatives of the invention are 0.010-10.0, 0.010-8.0, 0.010-6.0, 0.010-4.0, 0.010-2.0, 0.010-1.00, 0.010-0.80, 0.010-0.60, 0.010-0.40, 0.010-0.30, 0.010-0.20, 0.010-0.10, and 0.010-0.90 (nM), preferably 0.010-0.40, 0.010-0.30, 0.010-0.20, 0.010-0.10, and 0.010-0.90 (nM).

In a second aspect, the GLP-1 analogue or derivative thereof ("GLP-1 compound") has a high affinity to the GLP-1 receptor. The affinity to the GLP-1 receptor may be determined as described in Example 23, i.e. by way of displacement of $^{125}$I-GLP-1 from the receptor. BHK cells may be used for membrane preparation, preferably strain tk-ts13. The membranes may be purified, preferably as described in Example 23, A preferred binding assay method is the SPA assay of Example 23. The $IC_{50}$ value may be read from the resulting (binding) curve as the concentration which displaces 50% of $^{125}$I-GLP-1 from the receptor.

In a first particular embodiment, the $IC_{50}$ value is below 500 nM, preferably below 400 nM, more preferably below 300 nM, even more preferably below 200 nM, and most preferably below 100 nM.

In a second particular embodiment, the $IC_{50}$ value is below 80 nM, preferably below 60 nM, more preferably below 50 nM, even more preferably below 40 nM, and most preferably below 30 nM.

In a third particular embodiment, the $IC_{50}$ value is below 20 nM, preferably below 15 nM, more preferably below 10 nM, even more preferably below 5.0 nM, and most preferably below 4.0 nM.

In a fourth particular embodiment, the $IC_{50}$ value is below 3.0 nM, preferably below 2.0 nM, more preferably below 1.0 nM, even more preferably below 0.80 nM, and most preferably below 0.60 nM.

In a fifth particular embodiment, the $IC_{50}$ value is below 0.50 nM, preferably below 0.40 nM, more preferably below 0.30 nM, even more preferably below 0.20 nM, and most preferably below 0.10 nM.

Accordingly, exemplary ranges of $IC_{50}$ are: 0.1-400, 0.2-300, 0.3-200, 0.4-100, 0.5-50, and 1-10 nM.

In a third aspect, the present invention relates to a GLP-1 analogue or derivative thereof with high affinity binding to the isolated N-terminal extracellular domain of the GLP-1 receptor (nGLP-1R). The affinity may be measured as the ability to displace $^{125}$I-Exendin-4(9-39) from binding to nGLP-1R, e.g. as described in Example 22.

In this assay Exendin-4 binds nGLP-1R with an $IC_{50}$ value of 5 nM, GLP-1(7-37) binds nGLP-1R with an $IC_{50}$ value of 1120 nM and liraglutide binds nGLP-1R with an $IC_{50}$ value of 1500 nM. In one aspect of the invention, the GLP-1 analogues or derivatives thereof of this invention binds nGLP-1R with an $IC_{50}$ value lower than that of liraglutide. More preferable the GLP-1 analogues or derivatives thereof of this invention binds nGLP-1R with an $IC_{50}$ value lower than 100 nM and even more preferable below 10 nM or even below 5 nM.

The protein nGLP-1R may be prepared as described by Runge et al 2007 (In Biochemistry, vol. 46, pp. 5830-5840). The protein is then biotinylated and immobilized, preferably on streptavidin-coated SPA beads. The nGLP1R in a suitable buffer such as 0.1M $NaHCO_3$ may be biotinylated using 75 μg BNHS (Sigma H1759) to 1 mg protein. The biotinylated nGLP1R is subsequently preferably dialyzed against PBS. All reagents and analogues or derivatives are preferably diluted in PBS with 0.05% v/v Tween 20. The binding assay may e.g. be carried out in 96 well OptiPlates (PerkinElmer 6005290) in a final volume of 200 μl. Each well may contain 2 mg streptavidin coated SPA beads (PerkinElmer RPNQ007), 0.1 pmol biotinylated nGLP1R, 50 pCi $^{125}$I-Exendin (9-39) and test peptide in suitable final concentrations, e.g. ranging from 1000 nM to 0.064 nM. The plates are incubated on a shaker, preferably at RT for 3 hours. The SPA particles may be spun down by centrifugation, e.g. for 10 min at 1500 rpm, and the plates are counted, e.g. in a TopCount-NXT (PerkinElmer).

The affinity may be expressed by way of an $IC_{50}$ value, which is read from the curve as the concentration of the GLP-1 derivative which displaces 50% of $^{125}$I-Exendin-4 (9-39) from binding to nGLP-1R.

In a first particular embodiment, the GLP-1 derivative of the invention has an affinity to the extracellular domain of the GLP-1 receptor (nGLP-1R), measured as $IC_{50}$/nM in the assay of Example 22, of below 1500, preferably below 1000, even more preferably below 900, and most preferably below 800 (nM).

In a second particular embodiment, the GLP-1 derivative of the invention has an affinity to the extracellular domain of the GLP-1 receptor (nGLP-1R), measured as $IC_{50}$/nM in the assay of Example 22, of below 700, preferably below 600, even more preferably below 500, and most preferably below 400 (nM).

In a third particular embodiment, the GLP-1 derivative of the invention has an affinity to the extracellular domain of the GLP-1 receptor (nGLP-1R), measured as $IC_{50}$/nM in the assay of Example 22, of below 300, preferably below 200, even more preferably below 100, and most preferably below 80 (nM).

In a fourth particular embodiment, the GLP-1 derivative of the invention has an affinity to the extracellular domain of the GLP-1 receptor (nGLP-1R), measured as $IC_{50}$/nM in the assay of Example 22, of below 60, preferably below 50, even more preferably below 40, and most preferably below 30 (nM).

In a fifth particular embodiment, the GLP-1 derivative of the invention has an affinity to the extracellular domain of the GLP-1 receptor (nGLP-1R), measured as $IC_{50}$/nM in the assay of Example 22, of below 20, preferably below 15, even more preferably below 10.0, and most preferably below 5.0 (nM).

Accordingly, exemplary ranges of affinity to nGLP-1R ($IC_{50}$ in nM) of the GLP-1 derivative of the invention are: 5-1500, 5-1000, 10-500, 20-300, 50-500, 10-500, and 5-50 (nM).

The term "DPP-IV protected" as used herein referring to a polypeptide means a polypeptide which has been chemically modified in order to render said derivative resistant to the plasma peptidase dipeptidyl aminopeptidase-4 (DPP-IV). The DPP-IV enzyme in plasma is known to be involved in the degradation of several peptide hormones, e.g. GLP-1, GLP-2, Exendin-4 etc. Thus, a considerable effort is being made to develop analogues and derivatives of the polypeptides susceptible to DPP-IV mediated hydrolysis in order to reduce the rate of degradation by DPP-IV.

In one embodiment a GLP-1 analogue or derivative thereof according to the invention is a DPP-IV protected GLP-1 analogue or derivative thereof.

In one embodiment a GLP-1 analogue or derivative thereof according to the invention is a DPP-IV protected GLP-1 analogue or derivative thereof which is more resistant to DPP-IV than liraglutide.

Resistance of a peptide to degradation by dipeptidyl aminopeptidase IV is determined by the following degradation assay:

Aliquots of the peptide (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed.

Alternatively, the resistance of a peptide to degradation by dipeptidyl aminopeptidase IV is determined by the following degradation assay:

Aliquots of the peptide (4 nmol) are incubated at 37° C. with 10.9 mU of purified dipeptidyl aminopeptidase IV for 22 hours in 40 µL of 0.085 M Tris-HCl buffer, pH 8.0, in presence or absence of 1.6% human serum albumin. After 0, 4, and 22 hours samples of 10 µl are taken and enzymatic reactions are terminated by mixing with 100 µl of 1% trifluoroacetic acid. The peptide degradation products are separated and quantified using HPLC analysis. One method for performing this analysis is: The mixtures are applied onto an Agilent Zorbax 300SB-C18 (5 µm particles) 150×2.1 mm column and eluted at a flow rate of 0.5 ml/min with a linear gradient from 0.1% trifluoroacetic acid to 100% acetonitrile with 0.07% TFA in 30 minutes. Peptides and their degradation products are monitored by their absorbance at 214 nm, and are quantified by integration of their peak areas. The stability of a peptide against dipeptidyl aminopeptidase IV is determined as the peak area of the intact peptide relative to the sum of the peak areas of the intact peptide and the degradation product lacking the two aminoterminal amino acids after cleavage.

The term "pharmaceutically acceptable" as used herein means suited for normal pharmaceutical applications, i.e. giving rise to no serious adverse events in patients etc.

The term "excipient" as used herein means the chemical compounds which are normally added to pharmaceutical compositions, e.g. buffers, tonicity agents, preservatives and the like.

The term "effective amount" as used herein means a dosage which is sufficient to be effective for the treatment of the patient compared with no treatment.

The term "pharmaceutical composition" as used herein means a product comprising an active GLP-1 analogue or derivative thereof according to the invention together with pharmaceutical excipients such as buffer, preservative, and optionally a tonicity modifier and/or a stabilizer. Thus a pharmaceutical composition is also known in the art as a pharmaceutical formulation.

The term "treatment of a disease" as used herein means the management and care of a patient having developed the disease, condition or disorder. The purpose of treatment is to combat the disease, condition or disorder. Treatment includes the administration of the active analogue or derivative according to the invention to eliminate or control the disease, condition or disorder as well as to alleviate the symptoms or complications associated with the disease, condition or disorder.

In another aspect, the present invention relates to a GLP-1 analogue or derivative thereof that can bind to albumin and the GLP-1 receptor simultaneously.

In another aspect the present invention relates to a GLP-1 analogue or derivative thereof that bind to the GLP-1 receptor with an affinity below 100 nM, preferable below 30 nM in the presence of 2% albumin.

In another aspect, the GLP-1 analogue or derivative thereof ("GLP-1 compound") has an affinity to the GLP-1 receptor which is only partly decreased when comparing the affinity in the presence of very low concentration (e.g. 0.005% to 0.2%) of human albumin to the affinity in the presence of 2% human albumin. The shift in binding affinity under these conditions is less than 50 fold, preferable below 30 fold and more preferable below 10 fold.

In another aspect the present invention relates to a GLP-1 analogue or derivative thereof which is stable against the chemical degradation normally seen with exendin-4-especially oxidation and deamidation.

In another aspect, the present invention relates to a GLP-1 analogue or derivative thereof which has a high potency at the receptor. For very strong albumin binding analogues with albumin binding affinity below 100 nM, the GLP-1 potency is better than 3 micro molar and preferable the potency is better than 1 micromolar in the cAMP assay.

For strong albumin binding analogues or derivatives with albumin binding affinity below 500 nM, the GLP-1 potency is better than 1 micro molar and preferable the potency is better than 0.2 micromolar in the cAMP assay.

In another aspect, the present invention relates to a GLP-1 analogue or derivative thereof which has high albumin binding affinity. The analogues or derivatives of this invention have an albumin binding affinity that is below 1 micromolar. More preferable the analogues or derivatives of this invention has an albumin binding affinity that is below 500 nM and even more preferable below 200 nM or even below 100 nM.

The albumin binding affinity can be measured using the following assay:

Albumin binding assay:

The affinities of the GLP-1 analogue or derivative thereof for human serum albumin (HSA) are measured by a competition scintillation proximity assay (SPA). Streptavidin-SPA beads (GE Healthcare RPNQ0009) are incubated with biotinylated HSA for 5 hours. The beads are washed with buffer to remove unbound HSA. The beads are mixed with an $^{125}$I-labeled acylated GLP-1 analogue such as N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][A ib8, $^{125}$I-Tyr19, Arg34] GLP-1(7-37) or N-epsilon37-[2-(2-[2-((S)-4-((S)-4-(12-[4-(16-(1H-tetrazol-5-yl)hexadecanoylsulfamoyl) butyrylamino]dodecanoylamino)-4-carboxybutyrylamino)-4-carboxybutyrylamino)ethoxy]ethoxy)acetyl][Aib8, $^{125}$I-Tyr19, Glu22, Arg26, 34, Lys37] GLP-1(7-37)-NH2 in a buffer containing 100 mM Hepes, 100 mM NaCl, 10 mM MgSO$_4$, 0.025% Tween-20, pH 7.4. The mixture is pipetted into the wells of a Perkin Elmer Optiplate-96 6005290 (100 µl per well) and 100 µl of a dilution series of the GLP-1 analogue or derivative to be measured is added in the same buffer. After 20 hours of gentle rocking at room temperature the plates are centrifuged and counted on a TopCounter. Bound cpm are plotted as a function of GLP-1 analogue or derivative concentration end the EC50 value of the competition curve is used as a measure of the affinity of the analogue or derivative for HSA.

In another aspect, the present invention relates to a GLP-1 analogue or derivative thereof which has substantially improved terminal half-life in rodent and in a non-rodent model relative to liraglutide.

In one aspect of this invention, the terminal half-life in rodent or in a non-rodent model is improved at least 3 fold relative to liraglutide.

In another aspect of this invention, the terminal half-life in a non-rodent model is improved at least 6 fold relative to liraglutide.

In another aspect, the present invention relates to a GLP-1 analogue or derivative thereof which has an in vivo half-life of at least 10 hrs after i.v. administration to rats.

In another aspect, the present invention relates to a GLP-1 analogue or derivative thereof which has an in vivo half-life of at least 50 hrs after s.c. administration to mini pigs, and preferable an in vivo half-life of at least 80 hrs after s.c. administration to mini pigs.

In another aspect, the present invention relates to a GLP-1 analogue or derivative thereof which can be formulated into particles suitable for pulmonary administration.

In another aspect, the present invention relates to a GLP-1 analogue or derivative thereof which is chemically and physically stable at neutral pH, most preferably in the range 6-8.

In another aspect, the present invention relates to a GLP-1 analogue or derivative thereof which has little or no tendency to aggregate. In one aspect the aggregation tendency is significantly improved relatively to the aggregation tendency of liraglutide when tested in a thioflavin assay.

In another aspect, the present invention relates to a GLP-1 analogue or derivative thereof which is suitable for pulmonal delivery. This may be with regard to physical or chemical aspects which are useful for a pulmonal formulation. Alternatively, the analogues or derivatives are stable against degradation by enzymes in the airways and lungs.

In embodiments of the invention a combination of the above features is achieved.

The term "albumin binding moiety" as used herein means a residue which binds non-covalently to human serum albumin. The albumin binding residue attached to the therapeutic polypeptide typically has an albumin binding affinity that is below 1 micromolar, preferable below 500 nM and even more preferable below 200 nM or even below 100 nM.

A range of albumin binding residues are known among linear and branched lipohophillic moieties containing 4-40 carbon atoms having a distal acidic group.

The term "hydrophilic linker" as used herein means a spacer that separates a peptide and an albumin binding residue with a chemical moiety which comprises at least 5 non-hydrogen atoms where 30-50% of these are either N or O.

In one aspect the invention relates to a GLP-1 analogue or derivative thereof, which comprises a hydrophilic linker between the modified GLP-1 sequence and one or more albumin binding residue(s).

In one aspect, the hydrophilic linker is an unbranched oligo ethylene glycol moiety with appropriate functional groups at both terminals that forms a bridge between an amino group of the modified GLP-1 sequence and a functional group of the albumin binding residue.

In the formulas herein the terminal bonds from the attached groups are to be regarded as attachment bonds and not ending in methylene groups unless stated.

In one aspect of the invention, the GLP-1 analogue or derivative is selected form the group consisting of
[Glu22,Arg26]GLP-1 (7-33) amide,
N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Val25,Arg26,Leu27,Glu30,Lys33)GLP-1(7-33)amide,
N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Arg26,Glu30) GLP-1(7-33) amide,
[Glu22,Val25,Arg26] GLP-1 (7-33)amide,
N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Arg26,Glu30) GLP-1(7-33) amide,
[Glu22, Arg26]GLP-1(7-33)peptide,
N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-[Aib8,Lys20,Glu22,Val25,Arg26,Glu30] GLP-1 (7-33) amide, and
[Glu22,Val25,Arg26] GLP-1 (7-32)amide.

Formulation

Another object of the present invention is to provide a pharmaceutical formulation comprising an analogue or derivative according to the present invention which is present in a concentration from 0.1 mg/ml to 25 mg/ml, and wherein said formulation has a pH from 3.0 to 9.0. The formulation may further comprise a buffer system, preservative(s), tonicity agent(s), chelating agent(s), stabilizers and surfactants.

In one embodiment of the invention, the pharmaceutical formulation is an aqueous formulation, i.e. formulation comprising water. Such formulation is typically a solution or a suspension.

In a further embodiment of the invention, the pharmaceutical formulation is an aqueous solution.

The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the invention relates to a pharmaceutical formulation comprising an aqueous solution of an analogue or derivative according to the present invention, and a buffer, wherein said analogue or derivative is present in a concentration from 0.1 mg/ml or above, and wherein said formulation has a pH from about 3.0 to about 9.0.

In another embodiment of the invention, the pH of the formulation is from about 7.0 to about 9.5. In another embodiment of the invention, the pH of the formulation is from about 3.0 to about 7.0. In another embodiment of the invention, the pH of the formulation is from about 5.0 to about 7.5. In another embodiment of the invention, the pH of the formulation is from about 7.5 to about 9.0. In another embodiment of the invention, the pH of the formulation is from about 7.5 to about 8.5. In another embodiment of the invention, the pH of the formulation is from about 6.0 to about 7.5. In another embodiment of the invention, the pH of the formulation is from about 6.0 to about 7.0. In another embodiment, the pharmaceutical formulation is from 8.0 to 8.5.

In an embodiment of the invention, each administered dose contains from 0.01 mg-10 mg of active analogue or derivative according to the invention. In an embodiment, the dose administered contains more than 0.05 mg active analogue or derivative. In an embodiment, the dose administered contains more than 0.1 mg active analogue or derivative according to the invention. In an embodiment, the dose administered contains up to 10 mg active analogue or derivative according to the invention. In an embodiment, the dose administered contains up to 9 mg active analogue or derivative according to the invention. In an embodiment, the dose administered contains up to 8 mg active analogue or derivative according to the invention. In an embodiment, the dose administered contains up to 7 mg active analogue or derivative according to the invention. In an embodiment, the dose administered contains up to 6 mg active analogue or derivative according to the invention. In an embodiment, the dose administered contains up to 5 mg active analogue or derivative according to the invention. In an embodiment, the dose administered contains from 0.2 mg to 5 mg active analogue or derivative according to the invention.

In a further embodiment of the invention, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention, the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In an embodiment, the preservative is phenol or m-cresol. In a further embodiment of the invention, the preservative is present in a concentration from 0.1 mg/ml to 20 mg/ml. In a further embodiment of the invention, the preservative is present in a concentration from 0.1 mg/ml to 5 mg/ml. In a further embodiment of the invention, the preservative is present in a concentration from 5 mg/ml to 10 mg/ml. In a further embodiment of the invention, the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy,* 19$^{th}$ edition, 1995.

In a further embodiment of the invention, the formulation further comprises an isotonic agent. In a further embodiment of the invention, the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol)polyethyleneglycol (e.g. PEG400), or mixtures thereof. In an embodiment, the isotoncity agent is propyleneglycol. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. In one embodiment, the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention, the isotonic agent is present in a concentration from 1 mg/ml to 50 mg/ml. In a further embodiment of the invention, the isotonic agent is present in a concentration from 1 mg/ml to 7 mg/ml. In an embodiment of the invention, the isotonic agent is present in a concentration from 5 mg/ml to 7 mg/ml. In a further embodiment of the invention, the isotonic agent is present in a concentration from 8 mg/ml to 24 mg/ml. In a further embodiment of the invention, the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy,* 19$^{th}$ edition, 1995.

In a further embodiment of the invention, the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy,* 19$^{th}$ edition, 1995.

In a further embodiment of the invention, the formulation further comprises a stabilizer. The use of a stabilizer in pharmaceutical compositions is well-known to the skilled person. For convenience reference is made to Remington: *The Science and Practice of Pharmacy,* 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations.

By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention, methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention, the formulation further comprises a stabilizer selected from the group of high molecular weight polymers or low molecular compounds.

In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein.

Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention, the formulation further comprises a surfactant. In another embodiment of the invention, the pharmaceutical composition comprises two different surfactants. The term "Surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "Detergent" is a synonym used for surfactants in general.

Anionic surfactants may be selected from the group of: Chenodeoxycholic acid, Chenodeoxycholic acid sodium salt, Cholic acid, Dehydrocholic acid, Deoxycholic acid, Deoxycholic acid methyl ester, Digitonin, Digitoxigenin, N,N-Dimethyldodecylamine N-oxide, Docusate sodium, Glycochenodeoxycholic acid sodium, Glycocholic acid hydrate, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine sodium salt, N-Lauroylsarcosine, N-Lauroylsarcosine, Lithium dodecyl sulfate, Lugol, 1-Octanesulfonic acid sodium salt, 1-Octanesulfonic acid sodium salt, Sodium 1-butanesulfonate, Sodium 1-decanesulfonate, Sodium 1-dodecanesulfonate, Sodium 1-heptanesulfonate, Sodium 1-heptanesulfonate, Sodium 1-nonanesulfonate, Sodium 1-propanesulfonate monohydrate, Sodium 2-bromoethanesulfonate, Sodium cholate hydrate, ox or sheep bile, Sodium cholate hydrate, Sodium choleate, Sodium deoxycholate, Sodium dodecyl sulfate, Sodium dodecyl sulfate, Sodium hexanesulfonate, Sodium octyl sulfate, Sodium pentanesulfonate, Sodium taurocholate, Taurochenodeoxycholic acid sodium salt, Taurodeoxycholic acid sodium salt monohydrate, Taurolithocholic acid 3-sulfate disodium salt, Tauroursodeoxycholic acid sodium salt, Trizma® dodecyl sulfate, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), Dodecylphosphocholine (FOS-Choline-12), Decylphosphocholine (FOS-Choline-10), Nonylphosphocholine (FOS-Choline-9), dipalmitoyl phosphatidic acid, sodium caprylate, and/or Ursodeoxycholic acid.

Cationic surfactants may be selected from the group of: Alkyltrimethylammonium bromide Benzalkonium chloride, Benzalkonium chloride, Benzyldimethylhexadecylammonium chloride, Benzyldimethyltetradecylammonium chloride, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Hexadecyltrimethylammonium bromide, Hexadecyltrimethylammonium bromide, Polyoxyethylene (10)-N-tallow-1,3-diaminopropane, Thonzonium bromide, and/or Trimethyl(tetradecyl)ammonium bromide.

Nonionic surfactants may be selected from the group of: BigCHAP, Bis(polyethylene glycol bis[imidazoyl carbonyl]), block copolymers as polyethyleneoxide/polypropyleneoxide block copolymers such as poloxamers, poloxamer 188 and poloxamer 407, Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Dodecanoyl-N-methylglucamide, alkyl-polyglucosides, ethoxylated castor oil, Heptaethylene glycol monodecyl ether, Heptaethylene glycol monododecyl ether, Heptaethylene glycol monotetradecyl ether, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-beta-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-β-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tetradecyl-β-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165 solution, Triton® X-305 solution, Triton® X-405, Triton X-45, Triton® X-705-70, TWEEN® 20, TWEEN® 40, TWEEN® 60, TWEEN® 6, TWEEN® 65, TWEEN® 80, TWEEN® 81, TWEEN® 85, Tyloxapol, sphingophospholipids (sphingomyelin), and sphingoglycolipids (ceramides, gangliosides), phospholipids, and/or n-Undecyl β-D-glucopyranoside.

Zwitterionic surfactants may be selected from the group of: CHAPS, CHAPSO, 3-(Decyldimethylammonio)propanesulfonate inner salt, 3-(Dodecyldimethylammonio)propanesulfonate inner salt, 3-(Dodecyldimethylammonio)propanesulfonate inner salt, 3-(N,N-Dimethylmyristylammonio)propanesulfonate, 3-(N,N-Dimethyloctadecyl-ammonio)propanesulfonate, 3-(N,N-Dimethyloctylammonio)propanesulfonate inner salt, 3-(N,N-Dimethylpalmitylammonio)propanesulfonate, N-alkyl-N,N-dimethylammonio-1-propanesulfonates, 3-cholamido-1-propyldimethylammonio-1-propanesulfonate, Dodecylphosphocholine, myristoyl lysophosphatidylcholine, Zwittergent 3-12 (N-dodecyl-N,N-dimethyl-3-ammonio-1-propanesulfonate), Zwittergent 3-10 (3-(Decyldimethyl-ammonio)propanesulfonate inner salt), Zwittergent 3-08 (3-(Octyldimethyl-ammonio)pro-panesulfonate), glycerophospholipids (lecithins, kephalins, phosphatidyl serine), glyceroglycolipids (galactopyranoside), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, lysophosphatidylserine and lysophosphatidylthreonine, acylcarnitines and derivatives, $N^{beta}$-acylated derivatives of lysine, arginine or histidine, or side-chain acylated derivatives of lysine or arginine, $N^{beta}$-acylated derivatives of dipeptides comprising any combination of lysine, arginine or histidine and a neutral or acidic amino acid, $N^{beta}$-acylated derivative of a tripeptide comprising any combination of a neutral amino acid and two charged amino acids, or the surfactant may be selected from the group of imidazoline derivatives, long-chain fatty acids and salts thereof $C_6$-$C_{12}$ (e.g. oleic acid and caprylic acid), N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), or mixtures thereof.

The term "alkyl-polyglucosides" as used herein in relates to an straight or branched $C_{5-20}$-alkyl, -alkenyl or -alkynyl chain which is substituted by one or more glucoside moieties such as maltoside, saccharide etc. Embodiments of these alkyl-polyglucosides include $C_{6-18}$-alkyl-polyglucosides. Specific embodiments of these alkyl-polyglucosides includes the even numbered carbon-chains such as $C_6$, $C_8$, $C_{10}$, $C_{12}$, $C_{14}$, $C_{16}$, $C_{18}$ and $C_{20}$ alkyl chain. Specific embodiments of the glucoside moieties include pyranoside, glucopyranoside, maltoside, maltotrioside and sucrose. In embodiments of the invention, less than 6 glucosid moieties are attached to the alkyl group. In embodiments of the invention, less than 5 glucosid moieties are attached to the alkyl group. In embodiments of the invention, less than 4 glucosid moieties are attached to the alkyl group. In embodiments of the invention, less than 3 glucosid moieties are attached to the alkyl group. In embodiments of the invention, less than 2 glucosid moieties are attached to the alkyl group. Specific embodiments of alkyl-polyglucosides are alkyl glucosides such n-decyl β-D-glucopyranoside, decyl β-D-maltopyranoside, dodecyl β-D-glucopyranoside, n-dodecyl β-D-maltoside, n-dodecyl β-D-maltoside, n-dodecyl β-D-maltoside, tetradecyl β-D-glucopyranoside, decyl β-D-maltoside, hexadecyl β-D-maltoside, decyl β-D-maltotrioside, dodecyl β-D-maltotrioside, tetradecyl β-D-maltotrioside, hexadecyl β-D-maltotrioside, n-dodecyl-sucrose, n-decyl-sucrose, sucrose monocaprate, sucrose monolaurate, sucrose monomyristate, and sucrose monopalmitate.

The use of a surfactant in pharmaceutical compositions is well-known to the skilled person. For convenience reference is made to Remington: *The Science and Practice of Pharmacy*, 19th edition, 1995.

In a further embodiment of the invention, the formulation further comprises protease inhibitors such as EDTA (ethylenediamine tetraacetic acid) and benzamidineHCl, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an analogue or derivative according to the invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, chewing gum, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants. Compositions of the invention may further be compounded in, or attached to, for example through covalent, hydrophobic and electrostatic interactions, a drug carrier, drug delivery system and advanced drug delivery system in order to further enhance stability of the analogue or derivative of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of an analogue or derivative according to the invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension or a powder for the administration of the analogue or derivative of the present invention in the form of a nasal or pulmonal liquid or powder spray. As a still further option, the pharmaceutical compositions containing the analogue or derivative according to the invention can also be adapted to transdermal administration, e.g. by needle-free injection or from a patch, optionally an iontophoretic patch, or transmucosal, e.g. buccal, administration.

The analogues or derivatives according to the present invention can be administered via the pulmonary route in a vehicle, as a solution, suspension or dry powder using any of known types of devices suitable for pulmonary drug delivery. Examples of these comprise, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit Rev Ther Drug Carr Sys 14(4) (1997) 395-453).

Based on standardised testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. 3 Appl Physiol 84(2) (1998) 379-385). Mass median aerodynamic diameter (MMAD) and mass median effective aerodynamic diameter (MMEAD) are used interchangeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. 3 Appl Physiol 84(2) (1998) 379-385). MMAD is normally calculated from the measurement made with impactors, an instrument that measures the particle inertial behaviour in air.

In a further embodiment, the formulation could be aerosolized by any known aerosolisation technology, such as nebulisation, to achieve a MMAD of aerosol particles less than 10 µm, more preferably between 1-5 µm, and most preferably between 1-3 µm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the analogue or derivative according to the invention may optional be further optimized by using modifications of the inhalation techniques, for example, but not limited to: slow inhalation flow (e.g. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention, the pharmaceutical formulation comprising the analogue or derivative according to the present invention is stable for more than 6 weeks of usage and for more than 3 years of storage.

In another embodiment of the invention, the pharmaceutical formulation comprising the analogue or derivative according to the present invention is stable for more than 4 weeks of usage and for more than 3 years of storage.

In a further embodiment of the invention, the pharmaceutical formulation comprising the analogue or derivative according to the present invention is stable for more than 4 weeks of usage and for more than two years of storage.

In an even further embodiment of the invention, the pharmaceutical formulation comprising the analogue or derivative according to the present invention is stable for more than 2 weeks of usage and for more than two years of storage.

In another aspect, the present invention relates to the use of an analogue or derivative according to the present for the preparation of a medicament.

In one embodiment, an analogue or derivative according to the present is used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, stroke, coronary heart disease and other cardiovascular disorders, inflammatory bowel syndrome, dyspepsia and gastric ulcers.

In another embodiment, an analogue or derivative according to the present is used for the preparation of a medicament for delaying or preventing disease progression in type 2 diabetes.

In another embodiment an analogue or derivative according to the present is used for the preparation of a medicament for decreasing food intake, decreasing β-cell apoptosis, increasing β-cell function and β-cell mass, and/or for restoring glucose sensitivity to β-cells.

The treatment with an analogue or derivative according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonist, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with an analogue or derivative according to the present may also be combined with surgery—a surgery that influence the glucose levels and/or lipid homeostasis such as gastric banding or gastric bypass.

It should be understood that any suitable combination of the analogues or derivatives according to the present with one or more of the above-mentioned compounds and optionally one or more further pharmacologically active substances are considered to be within the scope of the present invention.

Method of Manufacturing Analogues

Depending on the sequence the analogues of this invention can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the therapeutic polypeptide may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well-known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein. The procedures used to ligate the DNA sequences coding for the present peptide, the promoter and optionally the terminator and/or secretory signal sequence, respectively, and to insert them into suitable vectors containing the information necessary for replication, are well-known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well-known and used in the art are, without limitation, *E. coli, Saccharomyces cerevisiae*, or mammalian BHK or CHO cell lines.

Embodiments According to the Invention

1. A GLP-1 analogue or derivative thereof, which comprises a modified GLP-1 sequence 7-35 (SEQ ID No 1) having:

i) a total of 2, 3, 4, 5 6, 7 or 8 amino acid substitutions compared to the sequence 7-35 of SEQ ID No 1, including
        a) a Glu residue at a position equivalent to position 22 of SEQ ID No 1, and
        b) an Arg residue at a position equivalent to position 26 of SEQ ID No 1,
    ii) optionally the amino acid(s) at a position equivalent to position 30, 31, 32, 33, 34, or 35 of SEQ ID No 1 can be absent provided that if the amino acid at position 30, 31, 32, 33 or 34 is absent then each amino acid residue downstream is also absent, and
    iii) optionally a C-terminal amide group.

2. The GLP-1 analogue or derivative thereof according to embodiment 1, which is derivatised with an albumin binding residue or is pegylated.

3. The GLP-1 analogue or derivative thereof according to any one of the embodiments 1-2, wherein the amino acid at position 35 is absent, and wherein the total length of the GLP-1 analogue is 28 amino acids.

4. The GLP-1 analogue or derivative thereof according to any one of the embodiments 1-2, wherein the amino acids at position 34 and 35 are absent, and wherein the total length of the GLP-1 analogue is 27 amino acids.

5. The GLP-1 analogue or derivative thereof according to any one of the embodiments 1-2, wherein the amino acids at position 33, 34 and 35 are absent, and wherein the total length of the GLP-1 analogue is 26 amino acids.

6. The GLP-1 analogue or derivative thereof according to any one of the embodiments 1-2, wherein the amino acids at position 32, 33, 34 and 35 are absent, and wherein the total length of the GLP-1 analogue is 25 amino acids.

7. The GLP-1 analogue or derivative thereof according to any one of the embodiments 1-2, wherein the amino acids at position 31, 32, 33, 34 and 35 are absent, and wherein the total length of the GLP-1 analogue is 24 amino acids.

8. The GLP-1 analogue or derivative thereof according to any one of the embodiments 1-2, wherein the amino acids at position 30, 31, 32, 33, 34 and 35 are absent, and wherein the total length of the GLP-1 analogue is 23 amino acids.

9. The GLP-1 analogue or derivative thereof according to any one of the embodiments 1-8 having a C-terminal amide group.

10. The GLP-1 analogue or derivative thereof according to any one of the embodiments 1-9 having the sequence of formula (I)

```
Formula (I)
                                        (SEQ ID No: 2)
Xaa7-Xaa8-Xaa9-Gly-Thr-Phe-Thr-Ser-Asp-Xaa16-

Ser-Xaa18-Tyr-Xaa20-Glu-Glu-Xaa23-Xaa24-Xaa25-

Arg-Xaa27-Phe-Ile-Xaa30-Xaa31-Leu-Xaa33-Xaa34-

Xaa35-R
``` wherein $Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_9$ is Glu or a Glu derivative such as alpha, alpha dimethyl-Glu;

$Xaa_{16}$ is Val or Leu;

$Xaa_{18}$ is Ser, Lys, Cys or Arg;

$Xaa_{20}$ is Leu, Lys or Cys;

$Xaa_{23}$ is Gln, Glu, Lys, Cys or Arg;

$Xaa_{24}$ is Ala or Asn;

$Xaa_{25}$ is Ala or Val;

$Xaa_{27}$ is Glu, Ala or Leu;

$Xaa_{30}$ is Ala, Glu, Arg or absent;

$Xaa_{31}$ is Trp, Lys, Cys or absent;

$Xaa_{33}$ is Val, Lys, Cys or absent;

$Xaa_{34}$ is Lys, Glu, Asn, Arg, Cys or absent;

$Xaa_{35}$ is Gly, Aib or absent;

R is amide or is absent;

provided that if $Xaa_{30}$, $Xaa_{31}$, $Xaa_{32}$, $Xaa_{33}$, or $Xaa_{34}$ is absent then each amino acid residue downstream is also absent.

11. The GLP-1 analogue or derivative thereof according to any one of the embodiments 1-9 having the sequence of formula (II)

```
Formula (II)
                                    (SEQ ID No: 3)
Xaa7-Xaa8-Glu-Gly-Thr-Phe-Thr-Ser-Asp-Val-Ser- Xaa18-Tyr-Leu-Glu-Glu-Gln-Ala-Ala-Arg-Glu-Phe- Ile-Xaa30-Trp-Leu-Xaa33-Xaa34-Xaa35-R
``` wherein $Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{18}$ is Ser, Lys or Arg;

$Xaa_{30}$ is Ala, Glu, Arg or is absent;

$Xaa_{33}$ is Val, Lys or absent;

$Xaa_{34}$ is Lys, Glu, Arg or is absent;

$Xaa_{35}$ is Gly, Aib or is absent;

R is amide or is absent.

12. The GLP-1 analogue or derivative thereof according to any one of the embodiments 1-11, wherein at least one amino acid residue is derivatised with A-B-C-D- wherein A- is selected from the group consisting of

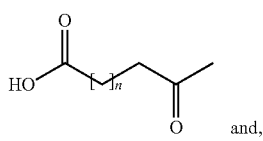
and,

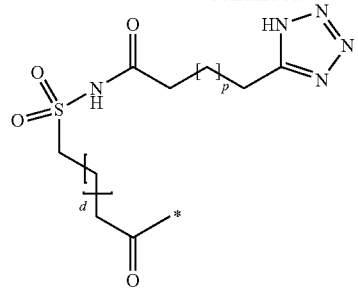

wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, -B- is selected from the group consisting of

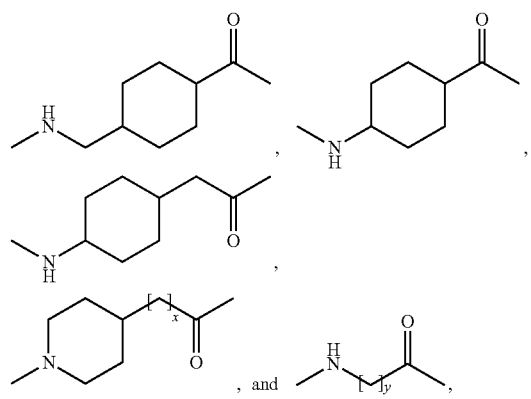
, and , wherein x is selected from the group consisting of 0, 1, 2, 3 and 4, and y is selected from the group consisting of 1, 2, 3, 4, 5, 6, 7, 8, 9, 10, 11 and 12, -C- is selected from the group consisting of

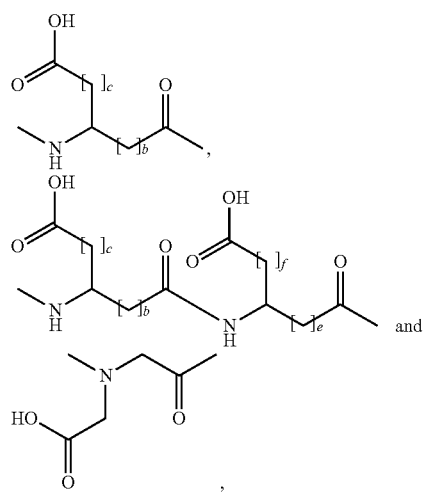
and
, wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and
-D- is attached to said amino acid residue and is a linker.
13. The GLP-1 analogue or derivative thereof according to embodiment 12, wherein D is selected from the group consisting of

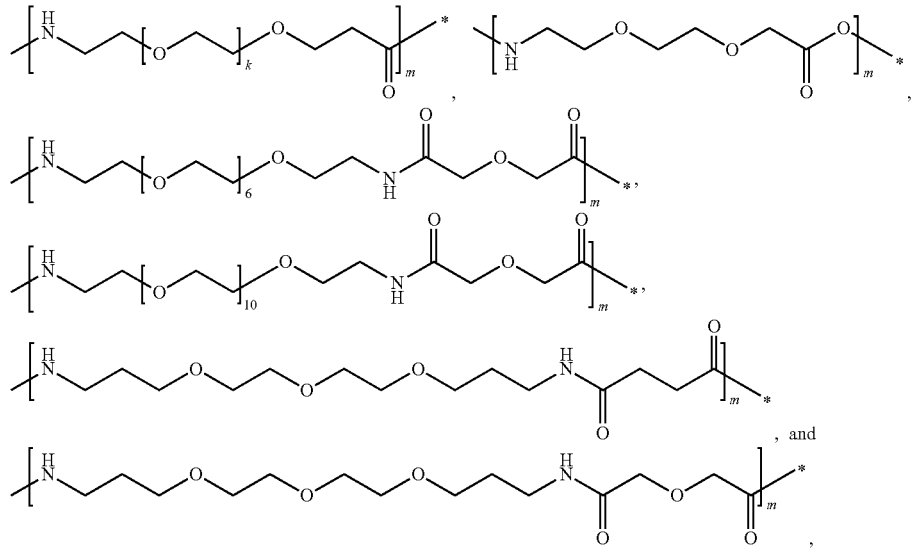

and wherein k is selected from the group consisting of 0, 1, 2, 3, 4, 5, 11 and 27, and m is selected from the group consisting of 0, 1, 2, 3, 4, 5 and 6.
14. A pharmaceutical composition comprising a GLP-1 analogue or derivative thereof according to any one of embodiments 1-13, and a pharmaceutically acceptable excipient.
15. A GLP-1 analogue or derivative thereof according to any one of embodiments 1-14 for use in the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

The amino acid sequence of human GLP-1(7-35) is included in the Sequence Listing as SEQ ID No 1, and SEQ ID Nos 2 and 3 are derivatives thereof according to the invention.

In the Sequence Listing, the numbering starts with amino acid residue no. 1. Accordingly, e.g., position 1 of SEQ ID No 1 is equivalent to position 7 of GLP-1(7-35) (His), position 16 of SEQ ID No 1 is equivalent to position 22 of GLP-1(7-35) (Gly), and position 20 of SEQ ID No 1 is equivalent to position 26 of GLP-1(7-35) (Lys)—and vice versa for the other positions and the other sequences.

Accordingly, the invention also provides, in above embodiment 1, a GLP-1 analogue or derivative which comprises a modified GLP-1(7-35) sequence having:
i) a total of 2, 3, 4, 5, 6, 7 or 8 amino acid substitutions compared to the sequence of SEQ ID No 1, including
a) a Glu residue at a position equivalent to position 22 of GLP-1(7-35) (position 16 of SEQ ID No 1), and
b) an Arg residue at a position equivalent to position 26 of GLP-1(7-35) (position 20 of SEQ ID No 1),
ii) optionally the amino acid(s) at a position equivalent to position 30, 31, 32, 33, 34, or 35 of GLP-1(7-35) (position 24, 25, 26, 27, 28, or 29, respectively, of SEQ ID No 1) can be absent provided that if the amino acid at position 30, 31, 32, 33 or 34 of GLP1(7-35) (position 24, 25, 26, 27, or 28 of SEQ ID No 1) is absent then each amino acid residue downstream is also absent, and
iv) optionally a C-terminal amide group.

The invention furthermore provides GLP-1 analogues or derivatives, methods and uses thereof, and pharmaceutical compositions with a content thereof corresponding to any of the above embodiments and particular embodiments according to the invention, in which corresponding position numbering amendments have been made as explained above, and shown above for the GLP-1 analogue or derivative of above embodiment 1.

1. A GLP-1 analogue or derivative thereof, which comprises a modified GLP-1 sequence 7-35 (SEQ ID No 1) having:
i) a total of 2, 3, 4, 5 6, 7 or 8 amino acid substitutions compared to the sequence 7-35 of SEQ ID No 1, including
a) a Glu residue at a position equivalent to position 22 of SEQ ID No 1, and
b) an Arg residue at a position equivalent to position 26 of SEQ ID No 1,
ii) optionally the amino acid(s) at a position equivalent to position 30, 31, 32, 33, 34, or 35 of SEQ ID No 1 can be absent provided that if the amino acid at position 30, 31, 32, 33 or 34 is absent then each amino acid residue downstream is also absent, and
iii) optionally a C-terminal amide group.
2. The GLP-1 analogue or derivative thereof according to embodiment 1, which is derivatised with an albumin binding residue or is pegylated.
3. The GLP-1 analogue or derivative thereof according to any one of the embodiments 1-2, wherein the amino acid at position 35 is absent, and wherein the total length of the GLP-1 analogue is 28 amino acids.
4. The GLP-1 analogue or derivative thereof according to any one of the embodiments 1-2, wherein the amino acids at position 34 and 35 are absent, and wherein the total length of the GLP-1 analogue is 27 amino acids.

5. The GLP-1 analogue or derivative thereof according to any one of the embodiments 1-2, wherein the amino acids at position 33, 34 and 35 are absent, and wherein the total length of the GLP-1 analogue is 26 amino acids.

6. The GLP-1 analogue or derivative thereof according to any one of the embodiments 1-2, wherein the amino acids at position 32, 33, 34 and 35 are absent, and wherein the total length of the GLP-1 analogue is 25 amino acids.

7. The GLP-1 analogue or derivative thereof according to any one of the embodiments 1-2, wherein the amino acids at position 31, 32, 33, 34 and 35 are absent, and wherein the total length of the GLP-1 analogue is 24 amino acids.

8. The GLP-1 analogue or derivative thereof according to any one of the embodiments 1-2, wherein the amino acids at position 30, 31, 32, 33, 34 and 35 are absent, and wherein the total length of the GLP-1 analogue is 23 amino acids.

9. The GLP-1 analogue or derivative thereof according to any one of the embodiments 1-8 having a C-terminal amide group.

10. The GLP-1 analogue or derivative thereof according to any one of the embodiments 1-9 having the sequence of formula (I)

```
Formula (I)
                                           (SEQ ID No: 2)
Xaa7-Xaa8-Xaa9-Gly-Thr-Phe-Thr-Ser-Asp-Xaa16-Ser- Xaa18-Tyr-Xaa20-Glu-Glu-Xaa23-Xaa24-Xaa25-Arg- Xaa27-Phe-Ile-Xaa30-Xaa31-Leu-Xaa33-Xaa34-Xaa35-R
``` wherein $Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_9$ is Glu or a Glu derivative such as alpha, alpha dimethyl-Glu;

$Xaa_{16}$ is Val or Leu;

$Xaa_{18}$ is Ser, Lys, Cys or Arg;

$Xaa_{20}$ is Leu, Lys or Cys;

$Xaa_{23}$ is Gln, Glu, Lys, Cys or Arg;

$Xaa_{24}$ is Ala or Asn;

$Xaa_{25}$ is Ala or Val;

$Xaa_{27}$ is Glu, Ala or Leu;

$Xaa_{30}$ is Ala, Glu, Lys, Arg or absent;

$Xaa_{31}$ is Trp, Lys, Cys or absent;

$Xaa_{33}$ is Val, Lys, Cys or absent;

$Xaa_{34}$ is Lys, Glu, Asn, Arg, Cys or absent;

$Xaa_{35}$ is Gly, Aib or absent;

R is amide or is absent;

provided that if $Xaa_{30}$, $Xaa_{31}$, $Xaa_{32}$, $Xaa_{33}$, or $Xaa_{34}$ is absent then each amino acid residue downstream is also absent.

11. The GLP-1 analogue or derivative thereof according to any one of the embodiments 1-9 having the sequence of formula (II)

```
Formula (II)
                                           (SEQ ID No: 3)
Xaa7-Xaa8-Glu-Gly-Thr-Phe-Thr-Ser-Asp-Val-Ser- Xaa18-Tyr-Leu-Glu-Glu-Gln-Ala-Ala-Arg-Glu-Phe- Ile-Xaa30-Trp-Leu-Xaa33-Xaa34-Xaa35-R
``` wherein $Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{18}$ is Ser, Lys or Arg;

$Xaa_{30}$ is Ala, Glu, Lys, Arg or is absent;

$Xaa_{33}$ is Val, Lys or absent;

$Xaa_{34}$ is Lys, Glu, Arg or is absent;

$Xaa_{35}$ is Gly, Aib or is absent;

R is amide or is absent.

12. The GLP-1 analogue or derivative thereof according to any one of the embodiments 1-11, wherein at least one amino acid residue is derivatised with A-B-C-D- wherein A- is selected from the group consisting of

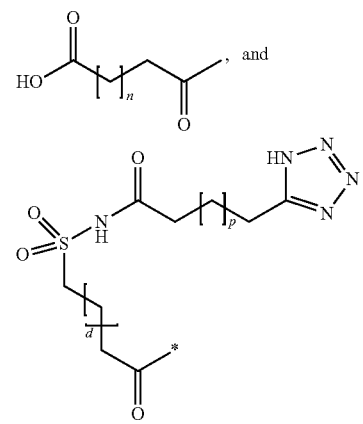

wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, -B- is selected from the group consisting of

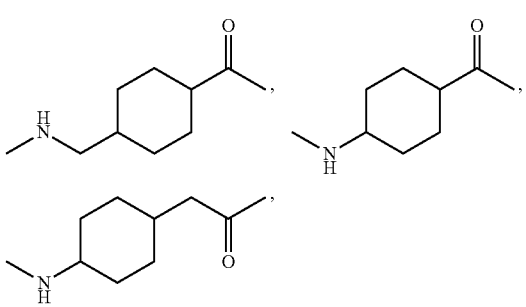

-continued

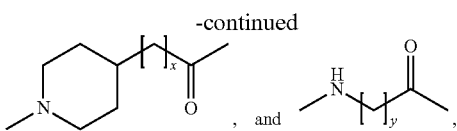, and wherein x is selected from the group consisting of 0, 1, 2, 3 and 4, and y is selected from the group consisting of 1, 2, 3, 4, 5, 6, 7, 8, 9, 10, 11 and 12,
-C- is selected from the group consisting of

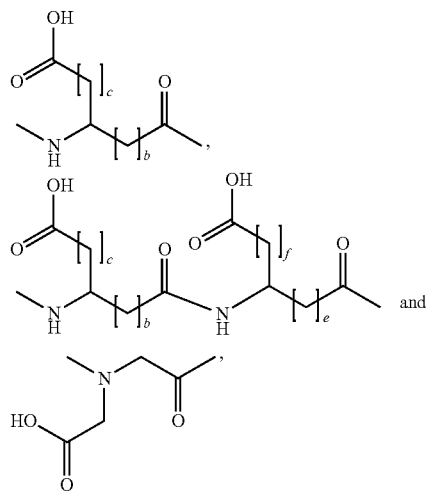

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and
-D- is attached to said amino acid residue and is a linker.

13. The GLP-1 analogue or derivative thereof according to embodiment 12, wherein D is selected from the group consisting of

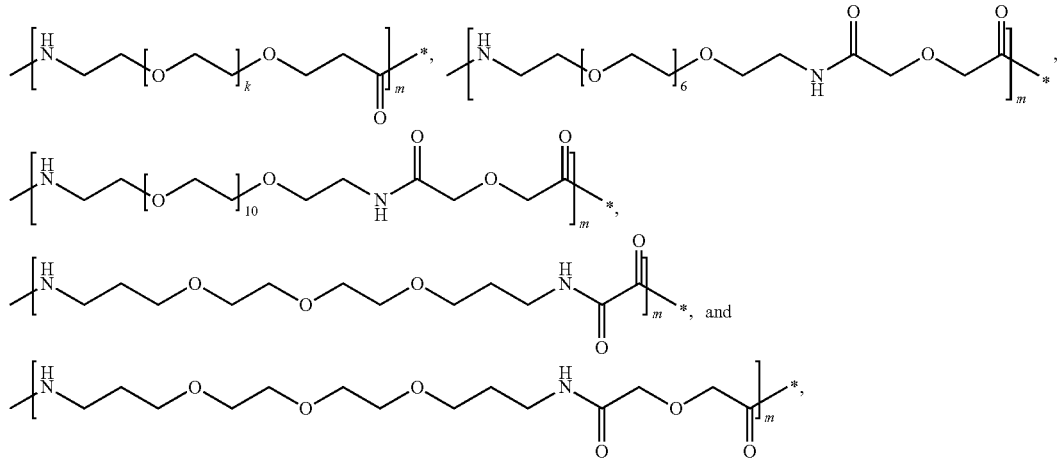

and wherein k is selected from the group consisting of 0, 1, 2, 3, 4, 5, 11 and 27, and m is selected from the group consisting of 0, 1, 2, 3, 4, 5 and 6.

14. A pharmaceutical composition comprising a GLP-1 analogue or derivative thereof according to any one of embodiments 1-13, and a pharmaceutically acceptable excipient.

15. A GLP-1 analogue or derivative thereof according to any one of embodiments 1-14 for use in the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

oOo

1. A GLP-1 analogue which is a modified GLP-1(7-35) (SEQ ID No 1) having:
   i) a total of 2, 3, 4, 5 6, 7, 8, or 9 amino acid substitutions as compared to GLP-1(7-35), including
   a) a Glu residue at a position equivalent to position 22 of GLP-1(7-35), and
   b) an Arg residue at a position equivalent to position 26 of GLP-1(7-35); or a derivative thereof.

2. The GLP-1 analogue or derivative thereof according to embodiment 1, wherein the amino acid(s) at a position equivalent to position 30, 31, 32, 33, 34, or 35 of GLP-1 (7-35) are absent, provided that if the amino acid at position 30, 31, 32, 33, or 34 is absent then each amino acid residue downstream is also absent.

3. The GLP-1 analogue or derivative thereof according to any one of embodiments 1-2, wherein the GLP-1 analogue comprises i) a C-terminal carboxylic acid group; or iii) a C-terminal amide group.

4. The GLP-1 analogue or derivative thereof according to any one of embodiments 1-3, which is derivatised with an albumin binding residue or is pegylated.

5. The GLP-1 analogue or derivative thereof according to any one of the embodiments 1-4, wherein the amino acid at position 35 is absent, and wherein the total length of the GLP-1 analogue is 28 amino acids.

6. The GLP-1 analogue or derivative thereof according to any one of the embodiments 1-5, wherein the amino acids at position 34 and 35 are absent, and wherein the total length of the GLP-1 analogue is 27 amino acids.

7. The GLP-1 analogue or derivative thereof according to any one of embodiments 1-6, wherein the amino acids at position 33, 34, and 35 are absent, and wherein the total length of the GLP-1 analogue is 26 amino acids.

8. The GLP-1 analogue or derivative thereof according to any one of the embodiments 1-7, wherein the amino acids at position 32, 33, 34, and 35 are absent, and wherein the total length of the GLP-1 analogue is 25 amino acids.

9. The GLP-1 analogue or derivative thereof according to any one of the embodiments 1-8, wherein the amino acids at position 31, 32, 33, 34, and 35 are absent, and wherein the total length of the GLP-1 analogue is 24 amino acids.

10. The GLP-1 analogue or derivative thereof according to any one of the embodiments 1-9, wherein the amino acids at position 30, 31, 32, 33, 34, and 35 are absent, and wherein the total length of the GLP-1 analogue is 23 amino acids.

11. A GLP-1 analogue or derivative thereof having the sequence of formula (I)

```
Formula (I)
                                          (SEQ ID No: 2)
Xaa7-Xaa8-Xaa9-Gly-Thr-Phe-Thr-Ser-Asp-Xaa16-

Ser-Xaa18-Tyr-Xaa20-Glu-Glu-Xaa23-Xaa24-Xaa25-Arg-

Xaa27-Phe-Ile-Xaa30-Xaa31-Leu-Xaa33-Xaa34-Xaa35-R
``` wherein
$Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_9$ is Glu or a Glu derivative such as alpha, alpha dimethyl-Glu;
$Xaa_{16}$ is Val or Leu;
$Xaa_{18}$ is Ser, Lys, Cys or Arg;
$Xaa_{20}$ is Leu, Lys or Cys;
$Xaa_{23}$ is Gln, Glu, Lys, Cys or Arg;
$Xaa_{24}$ is Ala or Asn;
$Xaa_{25}$ is Ala or Val;
$Xaa_{27}$ is Glu, Ala or Leu;
$Xaa_{30}$ is Ala, Glu, Lys, Arg or absent;
$Xaa_{31}$ is Trp, Lys, Cys or absent;
$Xaa_{33}$ is Val, Lys, Cys or absent;
$Xaa_{34}$ is Lys, Glu, Asn, Arg, Cys or absent;
$Xaa_{35}$ is Gly, Aib or absent;
R is amide or is absent;
provided that if $Xaa_{30}$, $Xaa_{31}$, $Xaa_{32}$, $Xaa_{33}$, or $Xaa_{34}$ is absent then each amino acid residue downstream is also absent.

12. A GLP-1 analogue or derivative thereof having the sequence of formula (II)

```
Formula (II)
                                          (SEQ ID No: 3)
Xaa7-Xaa8-Glu-Gly-Thr-Phe-Thr-Ser-Asp-Val-Ser- Xaa18-Tyr-Leu-Glu-Glu-Gln-Ala-Ala-Arg-Glu-Phe- Ile-Xaa30-Trp-Leu-Xaa33-Xaa34-Xaa35-R
``` wherein
$Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{18}$ is Ser, Lys or Arg;
$Xaa_{30}$ is Ala, Glu, Lys, Arg or is absent;
$Xaa_{33}$ is Val, Lys or absent;
$Xaa_{34}$ is Lys, Glu, Arg or is absent;
$Xaa_{35}$ is Gly, Aib or is absent;
R is amide or is absent.

13. The GLP-1 analogue or derivative thereof according to any one of the embodiments 1-12, wherein at least one amino acid residue is derivatised with A-B-C-D-
wherein A- is selected from the group consisting of

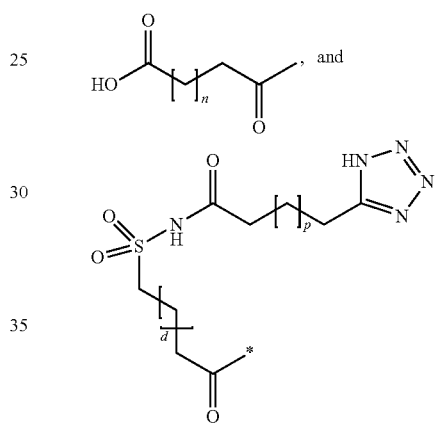

wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, -B- is selected from the group consisting of

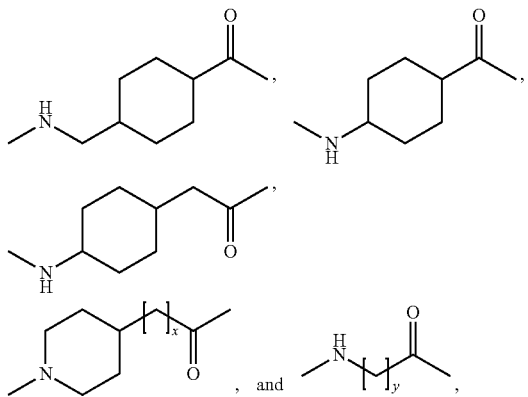

wherein x is selected from the group consisting of 0, 1, 2, 3 and 4, and y is selected from the group consisting of 1, 2, 3, 4, 5, 6, 7, 8, 9, 10, 11 and 12, -C- is selected from the group consisting of

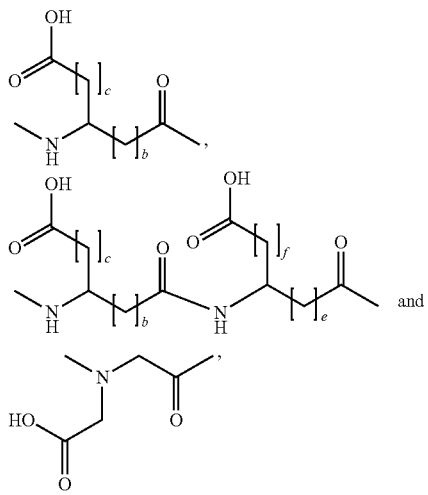

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker.

14. The GLP-1 analogue or derivative thereof according to embodiment 13, wherein D is selected from the group consisting of

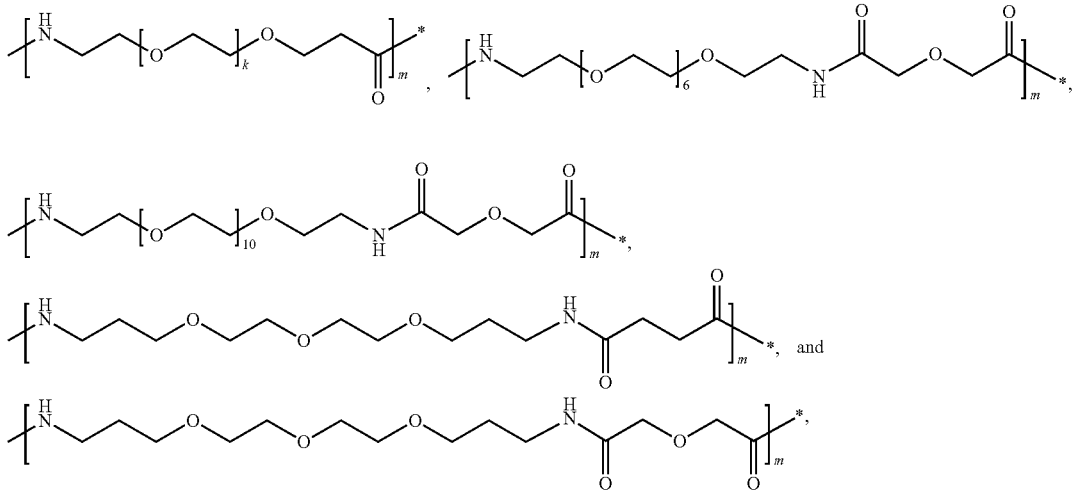

and wherein k is selected from the group consisting of 0, 1, 2, 3, 4, 5, 11 and 27, and m is selected from the group consisting of 0, 1, 2, 3, 4, 5 and 6.

15. A GLP-1 analogue or derivative which is selected from the following:

[Glu22, Arg26]GLP-1 (7-33) amide
N epsilon20 {2-(2-{2-[2-(2-{2-[4-Carboxy-4-(17-carboxy-heptadecanoylamino)butyrylamino]ethoxy}ethoxy) acetylamino]ethoxy}ethoxy)acetyl}-(Aib8,Lys20,Glu22, Val25,Arg26,Leu27,Glu30,Lys33)GLP-1(7-33)amide;
N epsilon20 {2-(2-{2-[2-(2-{2-[4-Carboxy-4-(17-carboxy-heptadecanoylamino)butyrylamino]ethoxy}ethoxy) acetylamino]ethoxy}ethoxy)acetyl}-(Aib8,Lys20,Glu22, Arg26,Glu30) GLP-1(7-33) amide;
[Glu22,Val25,Arg26] GLP-1 (7-33)amide;
[Aib8,Lys20,Glu22,Val25,Arg26,Glu30] GLP-1 (7-33) amide;
N epsilon20 {2-(2-{2-[2-(2-{2-[4-Carboxy-4-(17-carboxy-heptadecanoylamino)butyrylamino]ethoxy}ethoxy) acetylamino]ethoxy}ethoxy)acetyl}-[Aib8,Lys20,Glu22, Val25,Arg26,Glu30] GLP-1 (7-33) amide;
[Glu22, Arg26]GLP-1(7-33)peptide;
[Glu22,Val25,Arg26] GLP-1 (7-32)amide;
N-epsilon20 {2-(2-{2-[2-(2-{2-[4-Carboxy-4-(17-carboxy-heptadecanoylamino)butyrylamino]ethoxy}ethoxy) acetylamino]ethoxy}ethoxy)acetyl}-(Aib8,Lys20,Glu22, Arg26) GLP-1(7-33) amide;
N-epsilon31 {2-(2-{2-[2-(2-{2-[4-Carboxy-4-(17-carboxy-heptadecanoylamino)butyrylamino]ethoxy}ethoxy) acetylamino]ethoxy}ethoxy)acetyl}-(Aib8,Glu22,Val25, Arg26,Lys31) GLP-1(7-33) amide;
N-epsilon20 {2-(2-{2-[2-(2-{2-[4-Carboxy-4-(17-carboxy-heptadecanoylamino)butyrylamino]ethoxy}ethoxy) acetylamino]ethoxy}ethoxy)acetyl}-(DesaminoHis7, Lys20,Glu22,Arg26) GLP-1(7-33) amide;
N-epsilon31 {2-(2-{2-[2-(2-{2-[4-Carboxy-4-(17-carboxy-heptadecanoylamino)butyrylamino]ethoxy}ethoxy) acetylamino]ethoxy}ethoxy)acetyl}-(DesaminoHis7, Glu22,Arg26,Lys31)GLP-1(7-33) amide;
N-epsilon20 {2-(2-{2-[2-(2-{2-[4-Carboxy-4-(17-carboxy-heptadecanoylamino)butyrylamino]ethoxy}ethoxy) acetylamino]ethoxy}ethoxy)acetyl}-(Aib8,Lys20,Glu22, Val25,Arg26,Leu27,Glu30,Lys31)GLP-1(7-32) amide;
N-epsilon20 {2-(2-{2-[2-(2-{2-[4-Carboxy-4-(17-carboxy-heptadecanoylamino)butyrylamino]ethoxy}ethoxy) acetylamino]ethoxy}ethoxy)acetyl}-(Aib8, Lys20,Glu22, Val25,Arg26,Leu27,Nle30,Lys31)GLP-1(7-32) amide;
N-epsilon31-[2-(2-{2-[2-(2-{2-[(S)-4-Carboxy-4-({trans-4-[(19-carboxynonadecanoylamino)methyl] cyclohexanecarbonyl}amino)butyrylamino] ethoxy}ethoxy)acetylamino]ethoxy}ethoxy)acetyl]-[Aib8,Glu22,Val25,Arg26,Lys31]GLP-1-(7-33) amide;
[Desamino His7,Glu22,Arg26]-GLP-1 (7-34);
[Aib8,Lys20,Glu22,Val25,Arg26,Leu27,Lys31]GLP-1 (7-32) amide;
N-epsilon31-[2-(2-{2-[2-(2-{2-[(S)-4-Carboxy-4-(17-carboxyheptadecanoylamino)butyrylamino]ethoxy}ethoxy)

acetylamino]ethoxy}ethoxy)acetyl][DesaminoHis7, Asp11,Glu18,Glu22,Val25,Arg26,Asp27,Glu30,Lys31] GLP-1 (7-33) amide;

[Aib8,Glu22,Val25,Lys31]GLP-1(7-33)-amide; and

N-epsilon31-{2-(2-{2-[2-(2-{2-[4-Carboxy-4-(17-carboxy-heptadecanoylamino)butyrylamino]ethoxy}ethoxy)acetylamino]ethoxy}ethoxy)acetyl}-N-beta34-(2-(bis-carboxymethylamino)acetyl)[Aib8,Glu22,Val25,Arg26, Lys31,Dap34] GLP-1(7-34) amide.

16. A pharmaceutical composition comprising a GLP-1 analogue or derivative thereof according to any one of embodiments 1-15 or a pharmaceutically acceptable salt, amide, alkyl, or ester thereof, and a pharmaceutically acceptable excipient.

17. A GLP-1 analogue or derivative thereof according to any one of embodiments 1-15 or a pharmaceutical composition according to embodiment 16, for use as a medicament.

18. A GLP-1 analogue or derivative thereof according to any one of embodiments 1-15 or a pharmaceutical composition according to embodiment 16, for use in the treatment or prevention of hyperglycemia, type 2 diabetes, impaired glucose tolerance, type 1 diabetes, obesity, hypertension, syndrome X, dyslipidemia, cognitive disorders, ateroschlerosis, myocardial infarction, coronary heart disease and other cardiovascular disorders, stroke, inflammatory bowel syndrome, dyspepsia and gastric ulcers.

19. Use of a GLP-1 analogue or derivative thereof according to any one of embodiments 1-15 or a pharmaceutical composition according to embodiment 16, in the manufacture of a medicament for use in the treatment or prevention of hyperglycemia, type 2 diabetes, impaired glucose tolerance, type 1 diabetes, obesity, hypertension, syndrome X, dyslipidemia, cognitive disorders, ateroschlerosis, myocardial infarction, coronary heart disease and other cardiovascular disorders, stroke, inflammatory bowel syndrome, dyspepsia and gastric ulcers.

20. A method of treating or preventing hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and gastric ulcers by administering a pharmaceutically active amount of a GLP-1 analogue or derivative thereof according to any one of embodiments 1-15 or a pharmaceutical composition according to embodiment 16.

Embodiments

1. A GLP-1 analogue or derivative thereof, which comprises a modified GLP-1 sequence 7-35 (SEQ ID No 1) having:
a total of 2, 3, 4, 5 6, 7 or 8 amino acid substitutions compared to the sequence 7-35 of SEQ ID No 1, including a Glu residue at a position equivalent to position 22 of SEQ ID No 1, and
an Arg residue at a position equivalent to position 26 of SEQ ID No 1,
optionally the amino acid(s) at a position equivalent to position 30, 31, 32, 33, 34, or 35 of SEQ ID No 1 can be absent provided that if the amino acid at position 30, 31, 32, 33 or 34 is absent then each amino acid residue downstream is also absent, and
optionally a C-terminal amide group.

2. The GLP-1 analogue or derivative thereof according to embodiment 1, which is derivatised with an albumin binding residue or is pegylated.

3. The GLP-1 analogue or derivative thereof according to any one of the embodiments 1-2, wherein the amino acid at position 35 is absent, and wherein the total length of the GLP-1 analogue is 28 amino acids.

4. The GLP-1 analogue or derivative thereof according to any one of the embodiments 1-2, wherein the amino acids at position 34 and 35 are absent, and wherein the total length of the GLP-1 analogue is 27 amino acids.

5. The GLP-1 analogue or derivative thereof according to any one of the embodiments 1-2, wherein the amino acids at position 33, 34 and 35 are absent, and wherein the total length of the GLP-1 analogue is 26 amino acids.

6. The GLP-1 analogue or derivative thereof according to any one of the embodiments 1-2, wherein the amino acids at position 32, 33, 34 and 35 are absent, and wherein the total length of the GLP-1 analogue is 25 amino acids.

7. The GLP-1 analogue or derivative thereof according to any one of the embodiments 1-2, wherein the amino acids at position 31, 32, 33, 34 and 35 are absent, and wherein the total length of the GLP-1 analogue is 24 amino acids.

8. The GLP-1 analogue or derivative thereof according to any one of the embodiments 1-2, wherein the amino acids at position 30, 31, 32, 33, 34 and 35 are absent, and wherein the total length of the GLP-1 analogue is 23 amino acids.

9. The GLP-1 analogue or derivative thereof according to any one of the embodiments 1-8 having a C-terminal amide group.

10. The GLP-1 analogue or derivative thereof according to any one of the embodiments 1-9 having 3 amino acid substitutions compared to the sequence 7-35 of SEQ ID NO 1 including the substitutions at position 22 and 26.

11. The GLP-1 analogue or derivative thereof according to any one of the embodiments 1-10, which has a substitution at a position selected from the group of position 7, 8, 18, 20, 23, 24, 25, 27, 30, 31, 33 and 34 compared to the sequence 7-35 of SEQ ID NO 1.

12. The GLP-1 analogue or derivative thereof according to embodiment 11, which has a substitution selected from the group consisting of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34 and Asn34.

13. The GLP-1 analogue or derivative thereof according to any one of the embodiments 11-12, which has a substitution selected from the group consisting of desaminoHis7, Aib8, Lys18, Lys20, Lys23, Glu30, Lys31, Lys33 and Lys34.

14. The GLP-1 analogue or derivative thereof according to any one of the embodiments 11-13, which has a substitution selected from the group consisting of desaminoHis7 and Aib8.

15. The GLP-1 analogue or derivative thereof according to any one of the embodiments 1-9 having 4 amino acid substitutions compared to the sequence 7-35 of SEQ ID NO 1 including the substitutions at position 22 and 26.

16. The GLP-1 analogue or derivative thereof according to any one of the embodiments 1-9 and 15, which has two substitutions at positions selected from the group of positions 7, 8, 18, 20, 23, 24, 25, 27, 30, 31, 33 and 34 compared to the sequence 7-35 of SEQ ID NO 1.

17. The GLP-1 analogue or derivative thereof according to any one of the embodiments 15-16, which has two substitutions selected from the group consisting of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34 and Asn34.

18. The GLP-1 analogue or derivative thereof according to any one of the embodiments 15-17 having an amino acid substitution selected from the group consisting of desamino-His7 and Aib8 and an amino acid substitution selected from the group consisting Lys18, Lys20, Lys23, Glu30, Lys31, Lys33 and Lys34.

19. The GLP-1 analogue or derivative thereof according to any one of the embodiments 15-18 having an amino acid substitution selected from the group consisting of desamino-His7 and Aib8, and an amino acid substitution selected from the group consisting Lys18, Lys20, Lys23, Glu30, Lys31, Lys33 and Lys34.

20. The GLP-1 analogue or derivative thereof according to any one of the embodiments 1-9 having 5 amino acid substitutions compared to the sequence 7-35 of SEQ ID NO 1 including the substitutions at position 22 and 26.

21. The GLP-1 analogue or derivative thereof according to any one of the embodiments 1-9 and 20, which has three amino acid substitutions at positions selected from the group of positions 7, 8, 18, 20, 23, 24, 25, 27, 30, 31, 33 and 34 compared to the sequence 7-35 of SEQ ID NO 1.

22. The GLP-1 analogue or derivative thereof according to any one of the embodiments 20-21, which has three amino acid substitutions selected from the group of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34 and Asn34.

23. The GLP-1 analogue or derivative thereof according to any one of the embodiments 20-22 having an amino acid substitution selected from the group consisting of desamino-His7 and Aib8, and two amino acid substitutions selected from the group consisting of Lys18, Lys20, Lys23, Glu30, Lys31, Lys33 and Lys34.

24. The GLP-1 analogue or derivative thereof according to any one of the embodiments 20-23 having an amino acid substitution selected from the group consisting of desamino-His7 and Aib8, and two amino acid substitutions selected from the group consisting of Lys18, Lys20, Lys23, Glu30, Lys31, Lys33 and Lys34.

25. The GLP-1 analogue or derivative thereof according to any one of the embodiments 1-9 having 6 amino acid substitutions compared to the sequence 7-35 of SEQ ID NO 1 including the substitutions at position 22 and 26.

26. The GLP-1 analogue or derivative thereof according to any one of the embodiments 1-9 and 25, which has four amino acid substitutions at positions selected from the group of positions 7, 8, 18, 20, 23, 24, 25, 27, 30, 31, 33 and 34.

27. The GLP-1 analogue or derivative thereof according to any one of the embodiments 25-26, which has four amino acid substitutions selected from the group consisting of desaminoHis7, Aib8, Lys18, Cys18, Lys20, Cys20, Lys23, Cys23, Asn24, Val25, Ala27, Leu27, Glu30, Lys31, Cys31, Lys33, Cys33, Lys34, Cys34 and Asn34.

28. The GLP-1 analogue or derivative thereof according to any one of the embodiments 25-27 having an amino acid substitution selected from the group consisting of desamino-His7 and Aib8 and three amino acid substitutions selected from the group consisting of Lys18, Lys20, Lys23, Glu30, Lys31, Lys33 and Lys34.

29. The GLP-1 analogue or derivative thereof according to any one of the embodiments 25-28 having an amino acid substitution selected from the group consisting of desamino-His7 and Aib8 and three amino acid substitutions selected from the group consisting of Lys18, Lys20, Lys23, Glu30, Lys31, Lys33 and Lys34.

30. The GLP-1 analogue or derivative thereof according to any one of the embodiments 1-29 having the sequence of formula (I)

Formula (I)
(SEQ ID No: 2)
$Xaa_7$-$Xaa_8$-$Xaa_9$-Gly-Thr-Phe-Thr-Ser-Asp-$Xaa_{16}$-

Ser-$Xaa_{18}$-Tyr-$Xaa_{20}$-Glu-Glu-$Xaa_{23}$-$Xaa_{24}$-$Xaa_{25}$-Arg- $Xaa_{27}$-Phe-Ile-$Xaa_{30}$-$Xaa_{31}$-Leu-$Xaa_{33}$-$Xaa_{34}$-$Xaa_{35}$-R wherein
$Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_9$ is Glu or a Glu derivative such as alpha, alpha dimethyl-Glu;
$Xaa_{16}$ is Val or Leu;
$Xaa_{18}$ is Ser, Lys, Cys or Arg;
$Xaa_{20}$ is Leu, Lys or Cys;
$Xaa_{23}$ is Gln, Glu, Lys, Cys or Arg;
$Xaa_{24}$ is Ala or Asn;
$Xaa_{25}$ is Ala or Val;
$Xaa_{27}$ is Glu, Ala or Leu;
$Xaa_{30}$ is Ala, Glu, Lys, Arg or absent;
$Xaa_{31}$ is Trp, Lys, Cys or absent;
$Xaa_{33}$ is Val, Lys, Cys or absent;
$Xaa_{34}$ is Lys, Glu, Asn, Arg, Cys or absent;
$Xaa_{35}$ is Gly, Aib or absent;
R is amide or is absent;
provided that if $Xaa_{30}$, $Xaa_{31}$, $Xaa_{32}$, $Xaa_{33}$, or $Xaa_{34}$ is absent then each amino acid residue downstream is also absent.

31. The GLP-1 analogue or derivative thereof according to any one of the embodiments 1-29 having the sequence of formula (II)

Formula (II)
(SEQ ID No: 3)
$Xaa_7$-$Xaa_8$-Glu-Gly-Thr-Phe-Thr-Ser-Asp-Val-Ser- $Xaa_{18}$-Tyr-Leu-Glu-Glu-Gln-Ala-Ala-Arg-Glu-Phe- Ile-$Xaa_{30}$-Trp-Leu-$Xaa_{33}$-$Xaa_{34}$-$Xaa_{35}$-R wherein
$Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{18}$ is Ser, Lys or Arg;
$Xaa_{30}$ is Ala, Glu, Lys, Arg or is absent;
$Xaa_{33}$ is Val, Lys or absent;
$Xaa_{34}$ is Lys, Glu, Arg or is absent;
$Xaa_{35}$ is Gly, Aib or is absent;
R is amide or is absent.

32. The GLP-1 analogue or derivative thereof according to any one of the embodiments 30-31, wherein R is absent.

33. The GLP-1 analogue or derivative thereof according to any one of the embodiments 30-32, wherein $Xaa_{35}$ and R are absent.

34. The GLP-1 analogue or derivative thereof according to any one of the embodiments 30-33, wherein $Xaa_{34}$, $Xaa_{35}$ and R are absent.

35. The GLP-1 analogue or derivative thereof according to any one of the embodiments 30-34, wherein $Xaa_{33}$, $Xaa_{34}$, $Xaa_{35}$ and R are absent.

36. The GLP-1 analogue or derivative thereof according to any one of the embodiments 30 and 32-35 having a total of 2 amino acids substitutions compared to the sequence 7-35 of SEQ ID NO 1, which are a Glu residue at a position equivalent to position 22 of SEQ ID No 2 and an Arg residue at a position equivalent to position 26 of SEQ ID No 2.

37. The GLP-1 analogue or derivative thereof according to any one of the embodiments 30 and 32-35 having a total of 3 amino acids substitutions compared to the sequence 7-35 of SEQ ID NO 1, which are a Glu residue at a position equivalent to position 22 of SEQ ID No 2, an Arg residue at a position equivalent to position 26 of SEQ ID No 2 and one amino acid substitution selected from the group consisting of $Xaa_7$, $Xaa_8$, $Xaa_9$, $Xaa_{16}$, $Xaa_{18}$, $Xaa_{20}$, $Xaa_{23}$, $Xaa_{24}$, $Xaa_{25}$, $Xaa_{27}$, $Xaa_{30}$, $Xaa_{31}$, $Xaa_{33}$, $Xaa_{34}$ and $Xaa_{35}$ in SEQ ID No 2 compared to the sequence 7-35 of SEQ ID No 1.

38. The GLP-1 analogue or derivative thereof according to any one of the embodiments 30 and 32-35 having a total of 4 amino acids substitutions compared to the sequence 7-35 of SEQ ID NO 1, which are a Glu residue at a position equivalent to position 22 of SEQ ID No 2, an Arg residue at a position equivalent to position 26 of SEQ ID No 2 and 2 amino acid substitution selected from the group consisting of $Xaa_7$, $Xaa_8$, $Xaa_9$, $Xaa_{16}$, $Xaa_{18}$, $Xaa_{20}$, $Xaa_{23}$, $Xaa_{24}$, $Xaa_{25}$, $Xaa_{27}$, $Xaa_{30}$, $Xaa_{31}$, $Xaa_{33}$, $Xaa_{34}$ and $Xaa_{35}$ in SEQ ID No 2 compared to the sequence 7-35 of SEQ ID No 1.

39. The GLP-1 analogue or derivative thereof according to any one of the embodiments 30 and 32-35 having a total of 5 amino acids substitutions compared to the sequence 7-35 of SEQ ID NO 1, which are a Glu residue at a position equivalent to position 22 of SEQ ID No 2, an Arg residue at a position equivalent to position 26 of SEQ ID No 2 and 3 amino acid substitution selected from the group consisting of $Xaa_7$, $Xaa_8$, $Xaa_9$, $Xaa_{16}$, $Xaa_{18}$, $Xaa_{20}$, $Xaa_{23}$, $Xaa_{24}$, $Xaa_{25}$, $Xaa_{27}$, $Xaa_{30}$, $Xaa_{31}$, $Xaa_{33}$, $Xaa_{34}$ and $Xaa_{35}$ in SEQ ID No 2 compared to the sequence 7-35 of SEQ ID No 1.

40. The GLP-1 analogue or derivative thereof according to any one of the embodiments 30 and 32-35 having a total of 6 amino acids substitutions compared to the sequence 7-35 of SEQ ID NO 1, which are a Glu residue at a position equivalent to position 22 of SEQ ID No 2, an Arg residue at a position equivalent to position 26 of SEQ ID No 2 and 4 amino acid substitution selected from the group consisting of $Xaa_7$, $Xaa_8$, $Xaa_9$, $Xaa_{16}$, $Xaa_{18}$, $Xaa_{20}$, $Xaa_{23}$, $Xaa_{24}$, $Xaa_{25}$, $Xaa_{27}$, $Xaa_{30}$, $Xaa_{31}$, $Xaa_{33}$, $Xaa_{34}$ and $Xaa_{35}$ in SEQ ID No 2 compared to the sequence 7-35 of SEQ ID No 1.

41. The GLP-1 analogue or derivative thereof according to any one of the embodiments 30 and 32-35 having a total of 7 amino acids substitutions compared to the sequence 7-35 of SEQ ID NO 1, which are a Glu residue at a position equivalent to position 22 of SEQ ID No 2, an Arg residue at a position equivalent to position 26 of SEQ ID No 2 and 5 amino acid substitution selected from the group consisting of $Xaa_7$, $Xaa_8$, $Xaa_9$, $Xaa_{16}$, $Xaa_{18}$, $Xaa_{20}$, $Xaa_{23}$, $Xaa_{24}$, $Xaa_{25}$, $Xaa_{27}$, $Xaa_{30}$, $Xaa_{31}$, $Xaa_{33}$, $Xaa_{34}$ and $Xaa_{35}$ in SEQ ID No 2 compared to the sequence 7-35 of SEQ ID No 1.

42. The GLP-1 analogue or derivative thereof according to any one of the embodiments 30 and 32-35 having a total of 8 amino acids substitutions compared to the sequence 7-35 of SEQ ID NO 1, which are a Glu residue at a position equivalent to position 22 of SEQ ID No 2, an Arg residue at a position equivalent to position 26 of SEQ ID No 2 and 3 amino acid substitution selected from the group consisting of $Xaa_7$, $Xaa_8$, $Xaa_9$, $Xaa_{16}$, $Xaa_{18}$, $Xaa_{20}$, $Xaa_{23}$, $Xaa_{24}$, $Xaa_{25}$, $Xaa_{27}$, $Xaa_{30}$, $Xaa_{31}$, $Xaa_{33}$, $Xaa_{34}$ and $Xaa_{35}$ in SEQ ID No 2 compared to the sequence 7-35 of SEQ ID No 1.

43. The GLP-1 analogue or derivative thereof according to any one of the embodiments 31-35 having a total of 2 amino acids substitutions compared to the sequence 7-35 of SEQ ID NO 1, which are a Glu residue at a position equivalent to position 22 of SEQ ID No 3 and an Arg residue at a position equivalent to position 26 of SEQ ID No 3.

44. The GLP-1 analogue or derivative thereof according to any one of the embodiments 31-35 having a total of 3 amino acids substitutions compared to the sequence 7-35 of SEQ ID NO 1, which are a Glu residue at a position equivalent to position 22 of SEQ ID No 3, an Arg residue at a position equivalent to position 26 of SEQ ID No 3 and one amino acid substitution selected from the group consisting of $Xaa_7$, $Xaa_8$, $Xaa_{18}$, $Xaa_{30}$, $Xaa_{33}$, $Xaa_{34}$ and $Xaa_{35}$ in SEQ ID No 3 compared to the sequence 7-35 of SEQ ID No 1.

45. The GLP-1 analogue or derivative thereof according to any one of the embodiments 31-35 having a total of 4 amino acids substitutions compared to the sequence 7-35 of SEQ ID NO 1, which are a Glu residue at a position equivalent to position 22 of SEQ ID No 3, an Arg residue at a position equivalent to position 26 of SEQ ID No 3 and 2 amino acid substitution selected from the group consisting of $Xaa_7$, $Xaa_8$, $Xaa_{18}$, $Xaa_{30}$, $Xaa_{33}$, $Xaa_{34}$ and $Xaa_{35}$ in SEQ ID No 3 compared to the sequence 7-35 of SEQ ID No 1.

46. The GLP-1 analogue or derivative thereof according to any one of the embodiments 31-35 having a total of 5 amino acids substitutions compared to the sequence 7-35 of SEQ ID NO 1, which are a Glu residue at a position equivalent to position 22 of SEQ ID No 3, an Arg residue at a position equivalent to position 26 of SEQ ID No 3 and 3 amino acid substitution selected from the group consisting of $Xaa_7$, $Xaa_8$, $Xaa_{18}$, $Xaa_{30}$, $Xaa_{33}$, $Xaa_{34}$ and $Xaa_{35}$ in SEQ ID No 3 compared to the sequence 7-35 of SEQ ID No 1.

47. The GLP-1 analogue or derivative thereof according to any one of the embodiments 31-35 having a total of 6 amino acids substitutions compared to the sequence 7-35 of SEQ ID NO 1, which are a Glu residue at a position equivalent to position 22 of SEQ ID No 3, an Arg residue at a position equivalent to position 26 of SEQ ID No 3 and 4 amino acid substitution selected from the group consisting of $Xaa_7$, $Xaa_8$, $Xaa_{18}$, $Xaa_{30}$, $Xaa_{33}$, $Xaa_{34}$ and $Xaa_{35}$ in SEQ ID No 3 compared to the sequence 7-35 of SEQ ID No 1.

48. The GLP-1 analogue or derivative thereof according to any one of the embodiments 31-35 having a total of 7 amino acids substitutions compared to the sequence 7-35 of SEQ ID NO 1, which are a Glu residue at a position equivalent to position 22 of SEQ ID No 3, an Arg residue at a position equivalent to position 26 of SEQ ID No 3 and 5 amino acid substitution selected from the group consisting of $Xaa_7$, $Xaa_8$, $Xaa_{18}$, $Xaa_{30}$, $Xaa_{33}$, $Xaa_{34}$ and $Xaa_{35}$ in SEQ ID No 3 compared to the sequence 7-35 of SEQ ID No 1.

49. The GLP-1 analogue or derivative thereof according to any one of the embodiments 31-35 having a total of 8 amino acids substitutions compared to the sequence 7-35 of SEQ ID NO 1, which are a Glu residue at a position equivalent to position 22 of SEQ ID No 3, an Arg residue at a position equivalent to position 26 of SEQ ID No 3 and 3 amino acid substitution selected from the group consisting of $Xaa_7$, $Xaa_8$, $Xaa_{18}$, $Xaa_{30}$, $Xaa_{33}$, $Xaa_{34}$ and $Xaa_{35}$ in SEQ ID No 3 compared to the sequence 7-35 of SEQ ID No 1.

50. The GLP-1 analogue or derivative thereof according to any one of the embodiments 30-49 wherein $Xaa_7$ is desamino-histidine.

51. The GLP-1 analogue or derivative thereof according to any one of the embodiments 30-49 wherein $Xaa_8$ is Aib.

52. The GLP-1 analogue or derivative thereof according to any one of the embodiments 1-51, wherein the amino acid which is pegylated or derivatised with an albumin binding residue is a Lys-residue or a Cys-residue.

53. The GLP-1 analogue or derivative thereof according to any one of the embodiments 1-51, wherein the amino acid which is pegylated or derivatised with an albumin binding residue is a Lys-residue.

54. The GLP-1 analogue or derivative thereof according to any one of the embodiments 1-51, wherein the C-terminal amino acid is pegylated or derivatised with an albumin binding residue.

55. The GLP-1 analogue or derivative thereof according to any one of the embodiments 1-54, which has been pegylated or derivatised with an albumin binding residue at position 18, 20, 23, 31, 33, 34 or at the C-terminal amino acid.

56. The GLP-1 analogue or derivative thereof according to any one of the embodiments 1-55, which has been pegylated or derivatised with an albumin binding residue at position 18.

57. The GLP-1 analogue or derivative thereof according to any one of the embodiments 1-55, which has been pegylated or derivatised with an albumin binding residue at position 20.

58. The GLP-1 analogue or derivative thereof according to any one of the embodiments 1-55, which has been pegylated or derivatised with an albumin binding residue at position 23.

59. The GLP-1 analogue or derivative thereof according to any one of the embodiments 1-55, which has been pegylated or derivatised with an albumin binding residue at position 31.

60. The GLP-1 analogue or derivative thereof according to any one of the embodiments 1-55, which has been pegylated or derivatised with an albumin binding residue at position 33.

61. The GLP-1 analogue or derivative thereof according to any one of the embodiments 1-55, which has been pegylated or derivatised with an albumin binding residue at position 34.

62. The GLP-1 analogue or derivative thereof according to any one of the embodiments 1-55, which has been derivatised with an albumin binding residue.

63. The GLP-1 analogue or derivative thereof according to any one of the embodiments 1-62, wherein at least one amino acid residue is derivatised with A-B-C-D- wherein A- is selected from the group consisting of

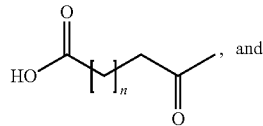
, and

-continued

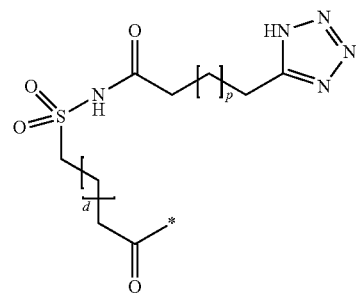

wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, -B- is selected from the group consisting of

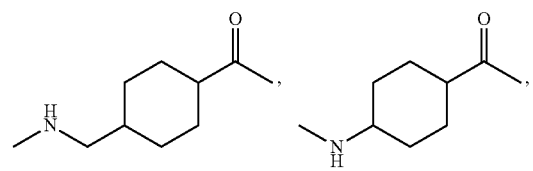

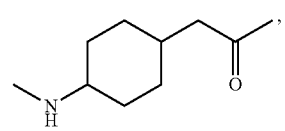

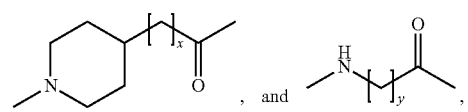
, and wherein x is selected from the group consisting of 0, 1, 2, 3 and 4, and y is selected from the group consisting of 1, 2, 3, 4, 5, 6, 7, 8, 9, 10, 11 and 12, -C- is selected from the group consisting of

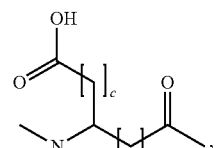

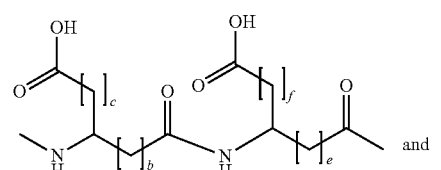
and

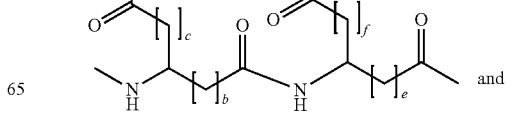

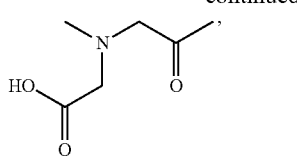

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker.

64. The GLP-1 analogue or derivative thereof according to embodiment 61, wherein one amino acid residue is derivatised with A-B-C-D-.

65. The GLP-1 analogue or derivative thereof according to any one of embodiments 63-64, wherein the derivatised amino acid residue comprises an amino group.

66. The GLP-1 analogue or derivative thereof according to any one of embodiments 63-65, wherein the derivatised amino acid residue comprises a primary amino group in a side chain.

67. The GLP-1 analogue or derivative thereof according to any one of embodiments 63-66, wherein the derivatised amino acid residue is lysine.

68. The GLP-1 analogue or derivative thereof according to any one of embodiments 63-67, wherein only one amino acid residue is derivatised.

69. The GLP-1 analogue or derivative thereof according to any one of embodiments 63-68, wherein A- is

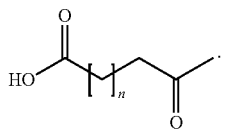

70. The GLP-1 analogue or derivative thereof according to any of the embodiments 63-69, wherein n is selected from the group consisting of 15 and 17, and more is preferred 17.

71. The GLP-1 analogue or derivative thereof according to any one of the embodiments 63-68, wherein A- is

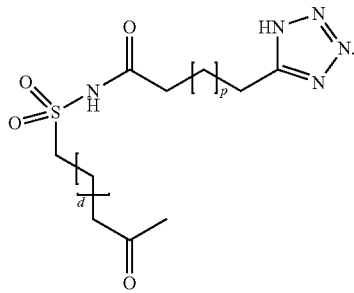

72. The GLP-1 analogue or derivative thereof according to any of the embodiments 63-68 and 69, wherein p is selected from the group consisting of 12, 13, and 14 and more preferred is 13.

73. The GLP-1 analogue or derivative thereof according to any of the embodiments 61-68 and 69-70, wherein d is selected from the group consisting of 0, 1, 2, 3 and 4, more preferred 0, 1 and 2 and most preferred 1.

74. The GLP-1 analogue or derivative thereof according to any of the embodiments 63-68 and 69-71, wherein d isselected from the group consisting of 0, 1 and 2 and p is selected from the group consisting of 12, 13 or 14, more preferred d is selected from the group consisting of 1 and 2 and p is selected from the group consisting of 13 and 14, and most preferred d is 1 and p is 13.

75. The GLP-1 analogue or derivative thereof according to any of the embodiments 63-74, wherein -B- is

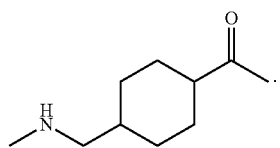

76. The GLP-1 analogue or derivative thereof according to any of the embodiments 63-74, wherein -B- is

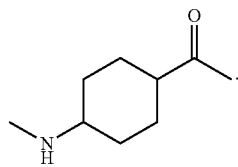

77. The GLP-1 analogue or derivative thereof according to any of the embodiments 63-74, wherein -B- is

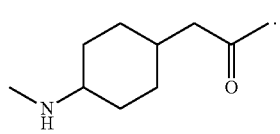

78. The GLP-1 analogue or derivative thereof according to any of the embodiments 63-74, wherein -B- is

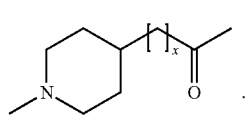

79. The GLP-1 analogue or derivative thereof according to embodiment 78, wherein x is selected from the group consisting of 0, 1 and 2, more preferred x is selected from the group consisting of 0 and 1 and most preferred x is 1.

80. The GLP-1 analogue or derivative thereof according to any of the embodiments 63-74, wherein -B- is

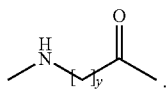

81. The GLP-1 analogue or derivative thereof according to embodiment 80, wherein y is selected from the group consisting of 2, 3, 4, 5, 6, 7, 8, 9 and 10 and more preferred y is selected from the group consisting of 2, 3, 4, 5, 6, 7, and 8

82. The GLP-1 analogue or derivative thereof according to any of the embodiments 63-81, wherein -C- is

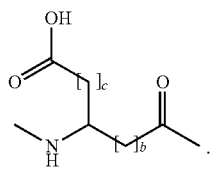

83. The GLP-1 analogue or derivative thereof according to embodiment 82, wherein c is selected from the group consisting of 0 and 1 and b is selected from the group consisting of 1 and 2, more preferred b is 1 and c is 0.

84. The GLP-1 analogue or derivative thereof according to any of the embodiments 63-81, wherein -C- is

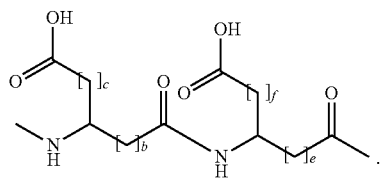

85. The GLP-1 analogue or derivative thereof according to embodiment 84, wherein f is selected from the group consisting of 0 and 1 and e is selected from the group consisting of 1 and 2, more preferred e is 1 and f is 0.

86. The GLP-1 analogue or derivative thereof according to any of the embodiments 63-81, wherein -C- is

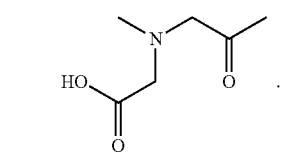

87. The GLP-1 analogue or derivative thereof according to any of the embodiments 63-86, wherein D is selected from the group consisting of

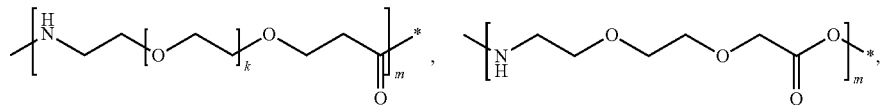

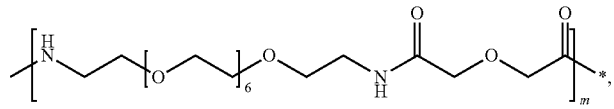

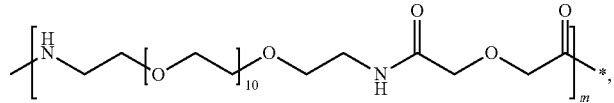

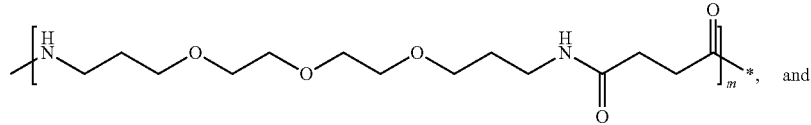 and

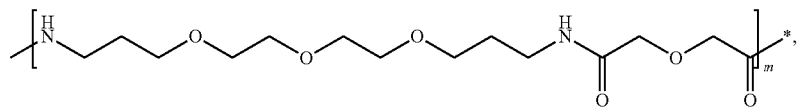

and wherein k is selected from the group consisting of 0, 1, 2, 3, 4, 5, 11 and 27, and m is selected from the group consisting of 0, 1, 2, 3, 4, 5 and 6.

88. The GLP-1 analogue or derivative thereof according to any of the embodiments 63-87, wherein -D- is

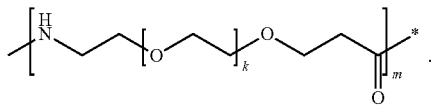

89. The GLP-1 analogue or derivative thereof according to embodiment 88, wherein k is selected from the group consisting of 1, 2, 3, 11 and 27 and more preferred k is 1.
90. The GLP-1 analogue or derivative thereof according to any of the embodiments 88-89, wherein m is selected from the group consisting of 0, 1, 2, 3, and 4 and more preferred m is selected from the group consisting of 0, 1 and 2.
91. The GLP-1 analogue or derivative thereof according to embodiment 91, wherein m is selected from the group consisting of 0, 1, 2, 3, and 4 and more preferred m is selected from the group consisting of 0, 1 and 2.
92. The GLP-1 analogue or derivative thereof according to any of the embodiments 63-87, wherein -D- is

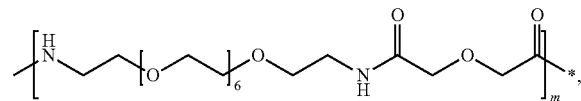

93. The GLP-1 analogue or derivative thereof according to embodiment 93, wherein m is selected from the group consisting of 0, 1, 2, 3, and 4 and more preferred m is selected from the group consisting of 0, 1 and 2.
94. The GLP-1 analogue or derivative thereof according to any of the embodiments 1-87, wherein -D- is

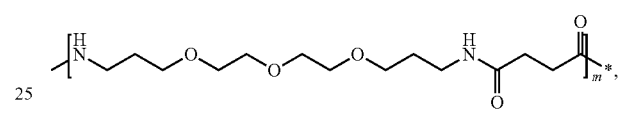

95. The GLP-1 analogue or derivative thereof according to embodiment 95, wherein m is selected from the group consisting of 0, 1, 2, 3, and 4 and more preferred m is selected from the group consisting of 0, 1 and 2.
96. The GLP-1 analogue or derivative thereof according to any of the embodiments 1-87, wherein -D- is

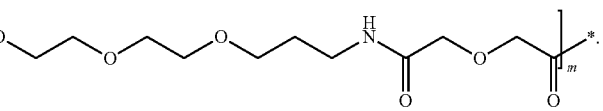

97. The GLP-1 analogue or derivative thereof according to embodiment 97, wherein m is selected from the group consisting of 0, 1, 2, 3, and 4 and more preferred m is selected from the group consisting of 0, 1 and 2.
98. The GLP-1 analogue or derivative thereof according to any of the embodiments 1-87, wherein -D- is

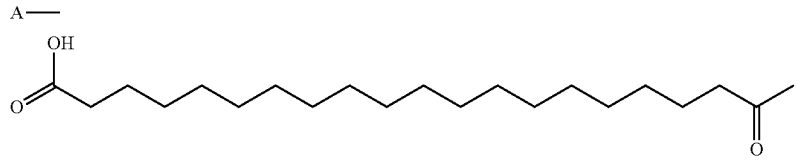

99. The GLP-1 analogue or derivative thereof according to embodiment 99, wherein m is selected from the group consisting of 0, 1, 2, 3, and 4 and more preferred m is selected from the group consisting of 0, 1 and 2.
100. The GLP-1 analogue or derivative thereof according to any of the embodiments 1-100, wherein A-B-C-D- is selected and combined from

A——

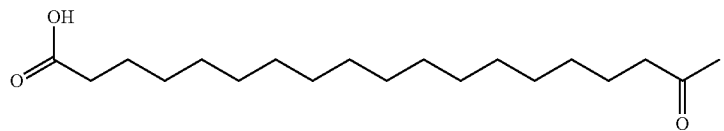

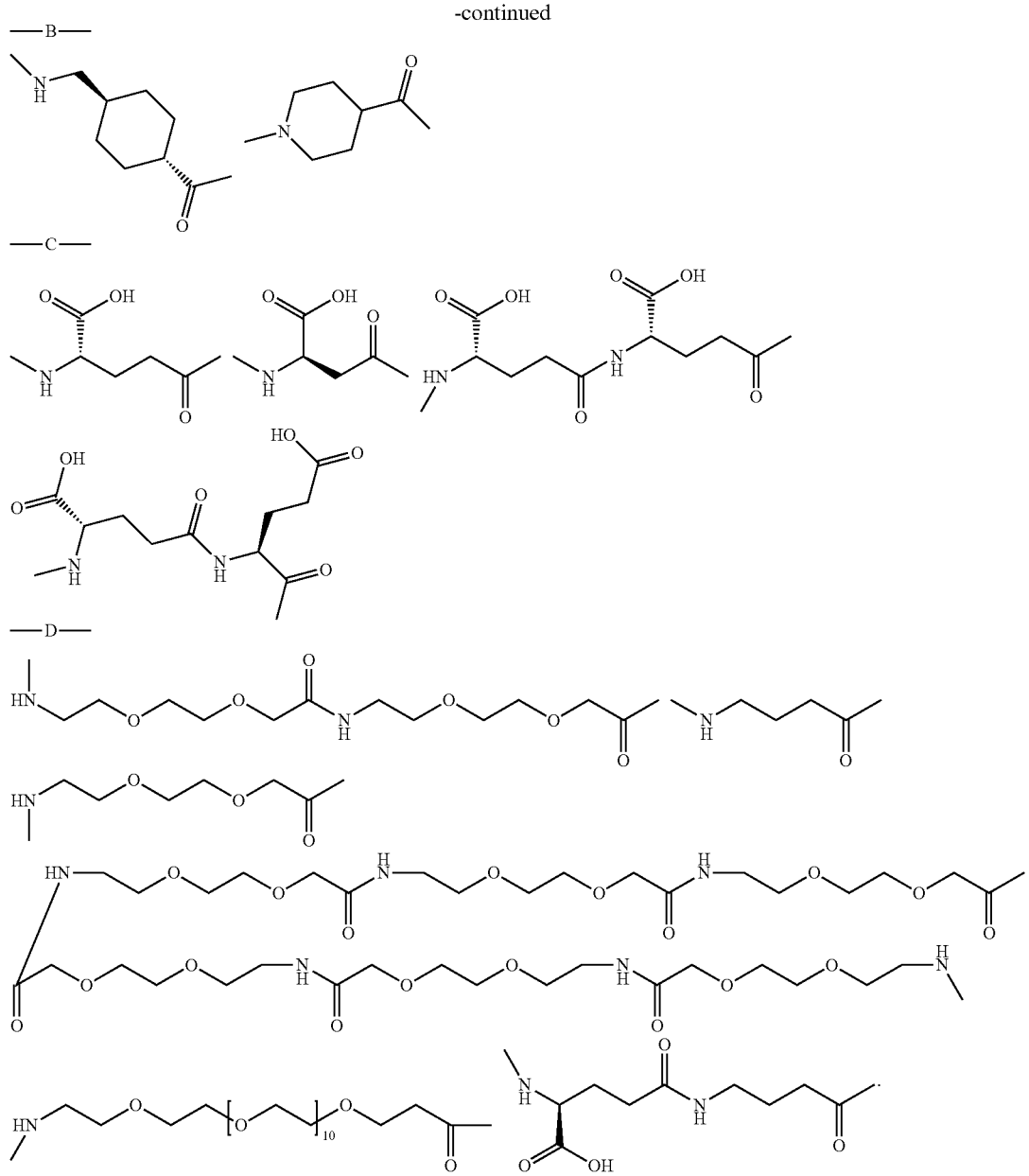
101. The GLP-1 analogue or derivative thereof according to any of the embodiments 1-100, wherein A-B-C-D- is selected and combined from
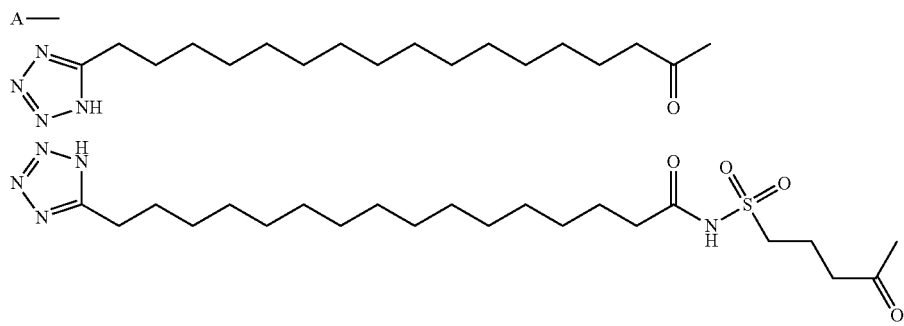

-continued
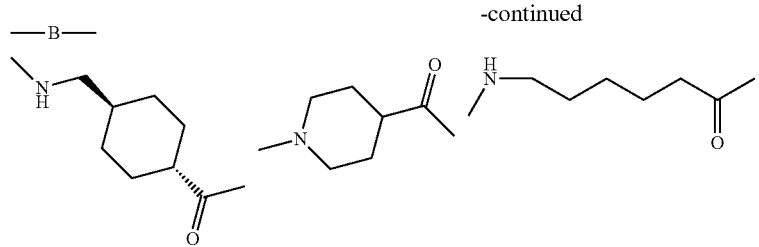
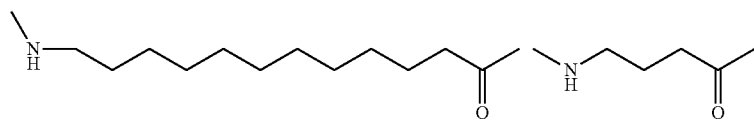
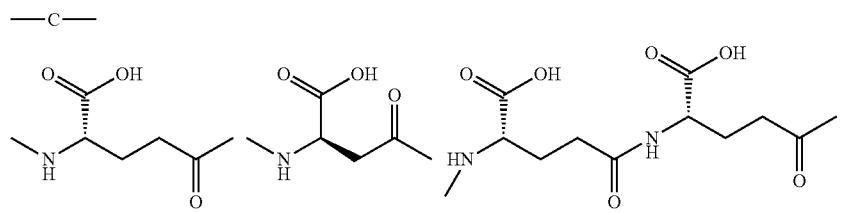
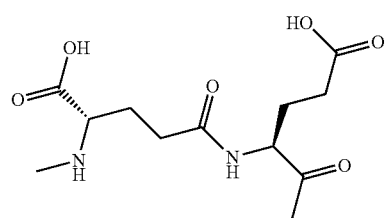
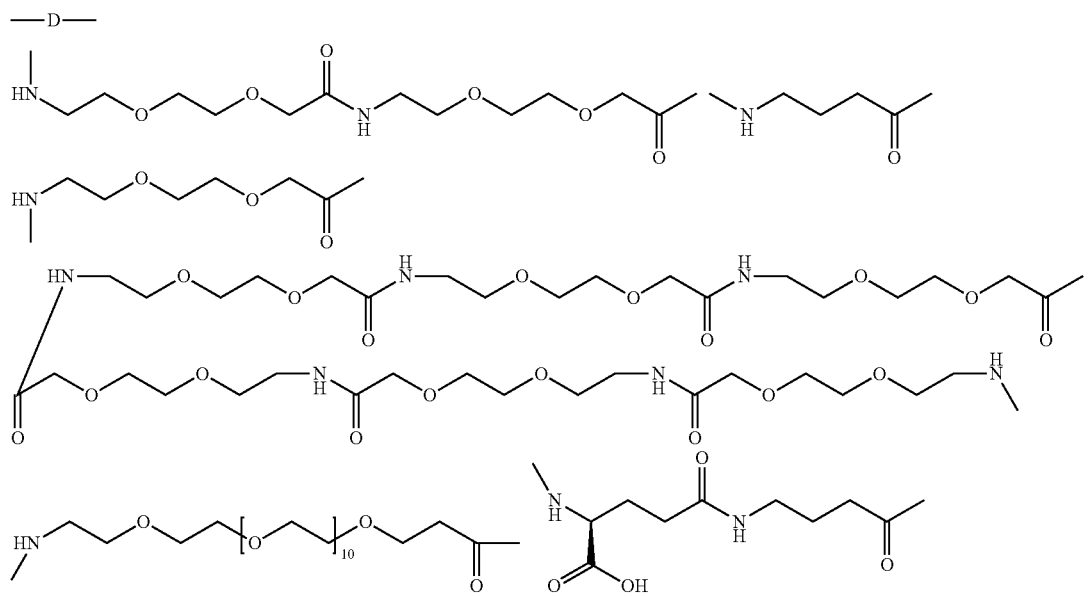
102. The GLP-1 analogue or derivative thereof according to any of the embodiments 1-100, wherein A-B-C-D- is selected from the group consisting of

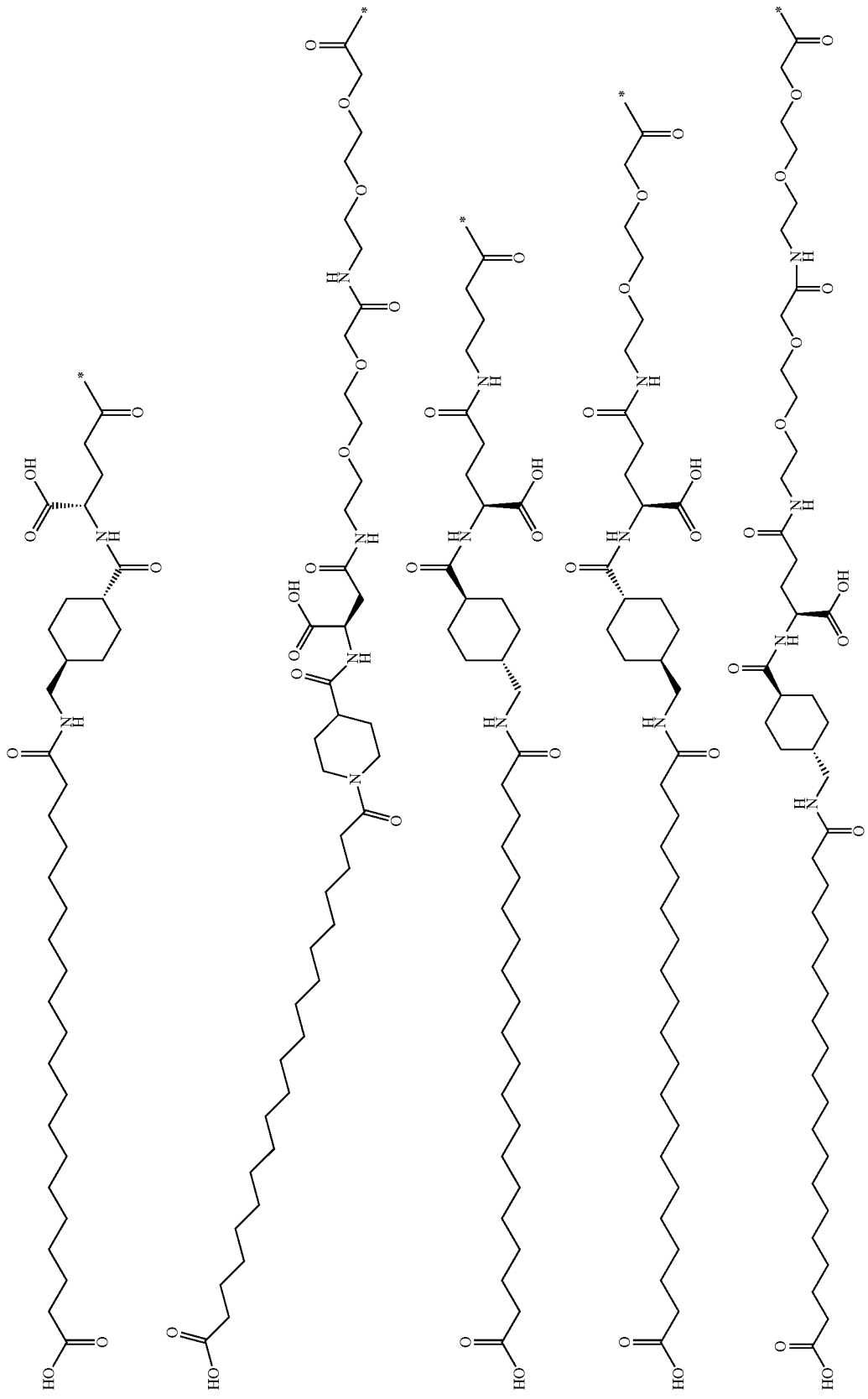

-continued
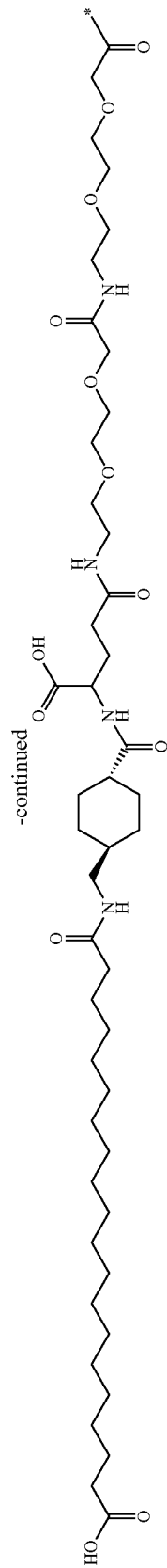
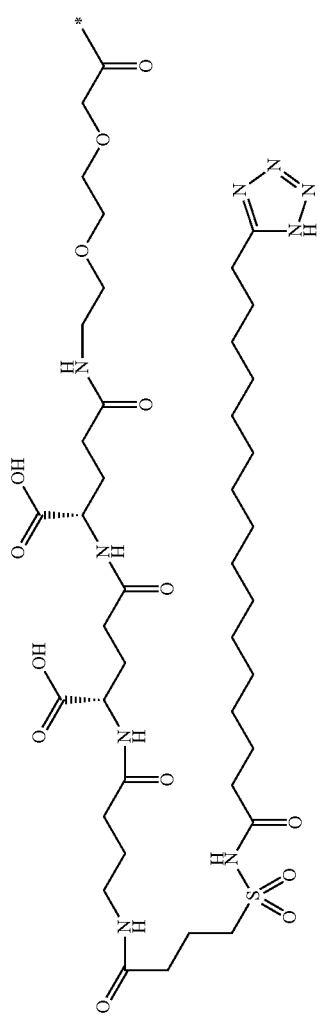
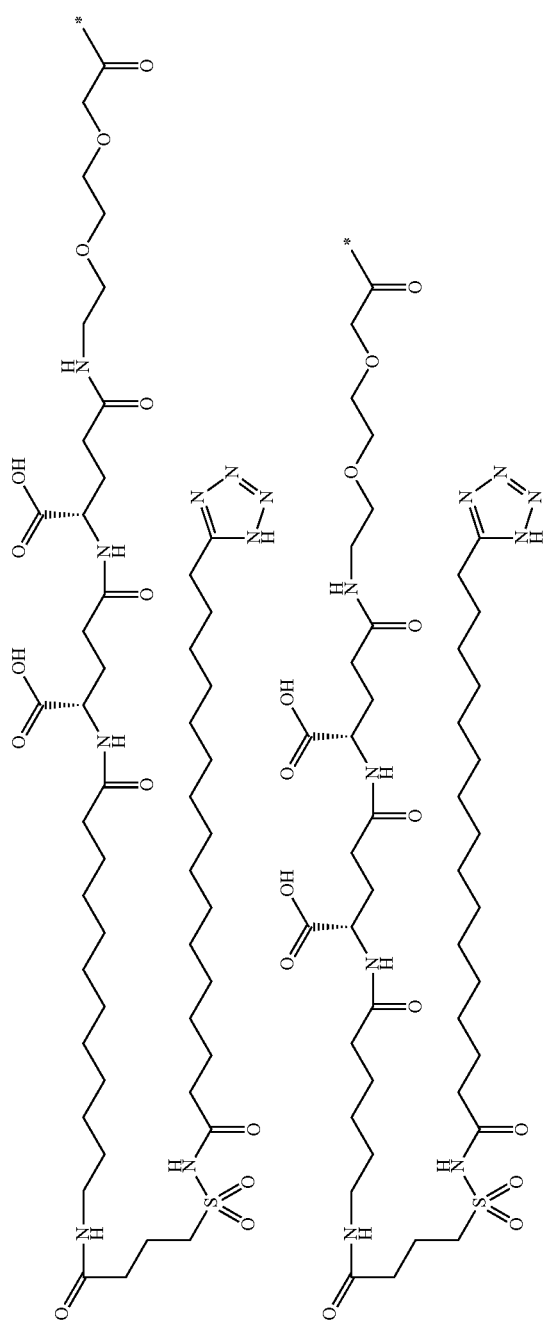

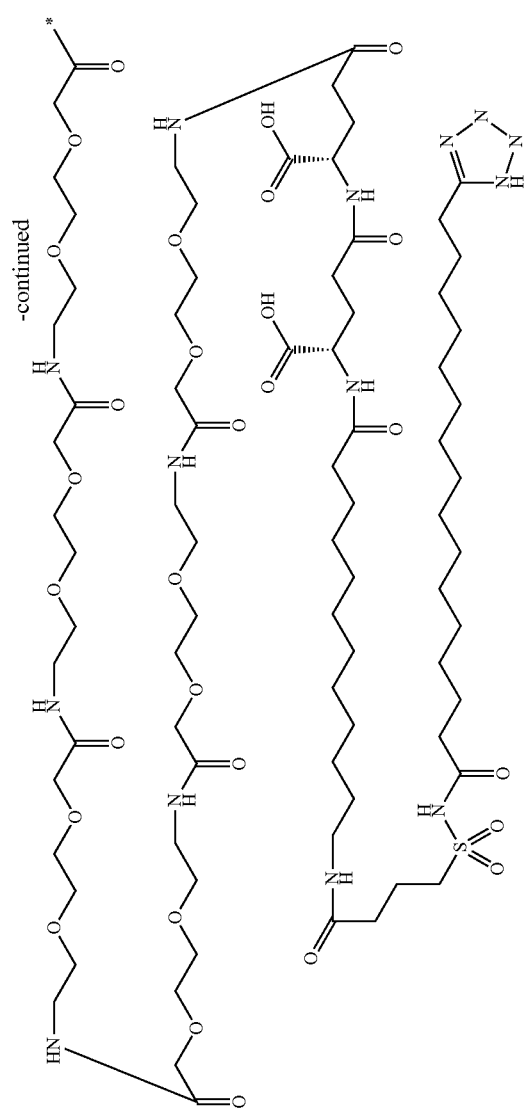
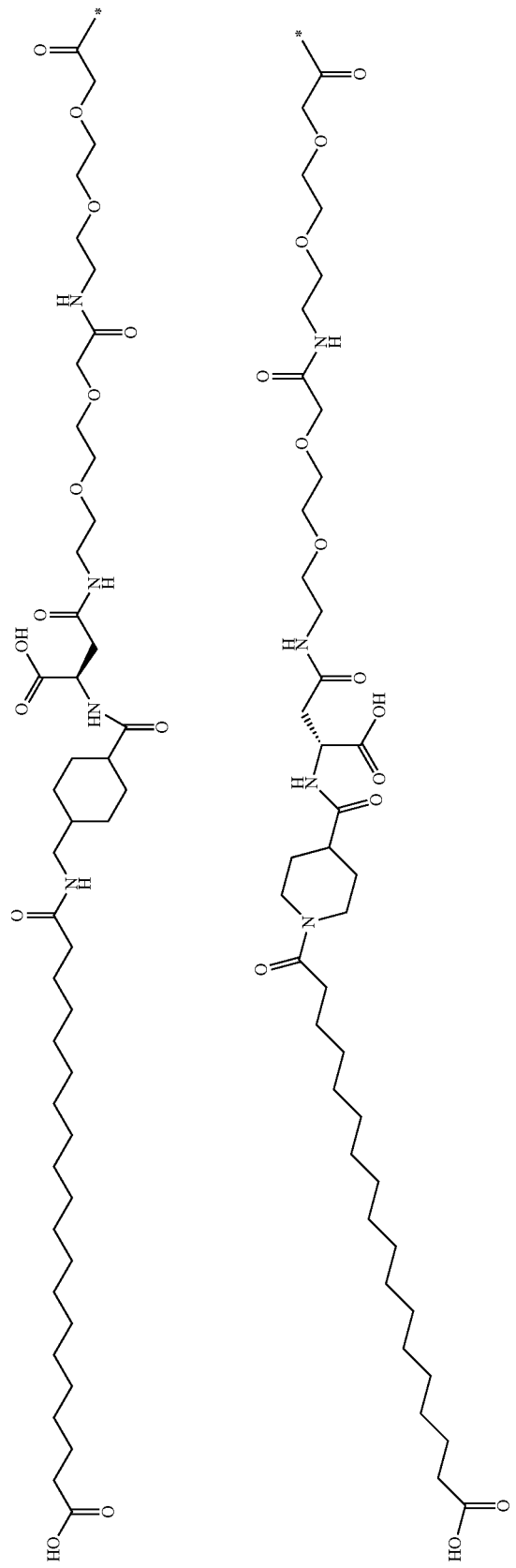

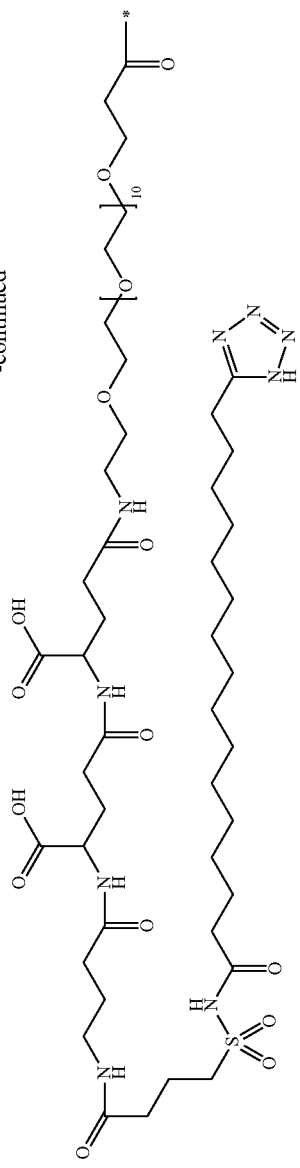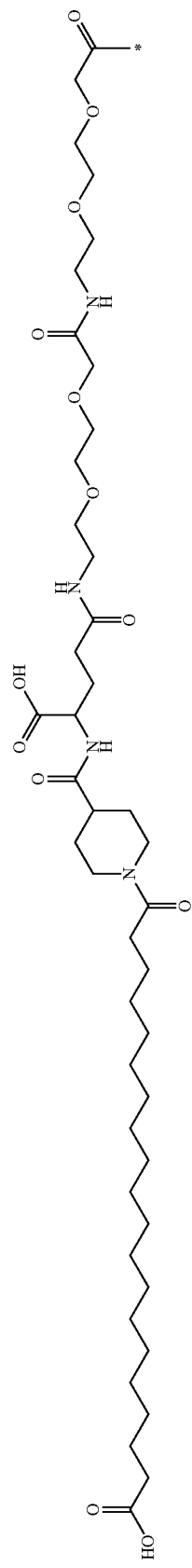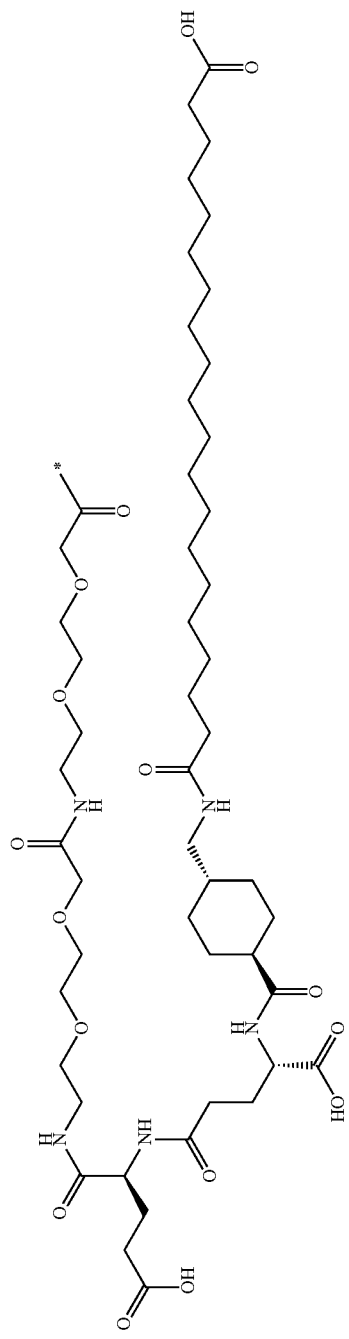

103. The GLP-1 analogue or derivative thereof according to any one of the embodiments 1-103, which comprises a hydrophilic linker between the modified GLP-1 sequence and one or more albumin binding residue(s).

104. The GLP-1 analogue or derivative thereof according to embodiment 104, wherein the hydrophilic linker is an unbranched oligo ethylene glycol moiety with appropriate functional groups at both terminals that forms a bridge between an amino group of the modified GLP-1 sequence and a functional group of the albumin binding residue.

105. The GLP-1 analogue or derivative thereof according to any of the above embodiments, which is selected from the group consisting of

[Glu22,Arg26]GLP-1 (7-33) amide,

N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Val25,Arg26,Leu27,Glu30,Lys33)GLP-1(7-33)amide, N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Arg26,Glu30) GLP-1(7-33) amide,

[Glu22,Val25,Arg26] GLP-1 (7-33)amide,

N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Arg26,Glu30) GLP-1(7-33) amide,

[Glu22, Arg26]GLP-1(7-33)peptide,

N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-[Aib8,Lys20,Glu22,Val25,Arg26,Glu30] GLP-1 (7-33) amide, and

[Glu22,Val25,Arg26] GLP-1 (7-32)amide.

106. A method for increasing the time of action in a patient of a GLP-1 analogue or derivative thereof, characterised in that a modified GLP-1 sequence 7-35 (SEQ ID No 1) is derivatised or pegylated as disclosed in any of the preceding embodiments.

107. A method for increasing the time of action in a patient of a GLP-1 analogue or derivative thereof to more than about 40 hours, characterised in that a modified GLP-1 sequence 7-37 (SEQ ID No 1) is derivatised or pegylated as disclosed in any of the preceding embodiments.

108. A pharmaceutical composition comprising a GLP-1 analogue or derivative thereof according to any one of embodiments 1-107, and a pharmaceutically acceptable excipient.

109. The pharmaceutical composition according to embodiment 109, which is suited for parenteral administration.

110. Use of a GLP-1 analogue or derivative thereof according to any one of embodiments 1-107 for the preparation of a medicament.

111. Use of a GLP-1 analogue or derivative thereof according to any one of embodiments 1-107 for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

112. Use of a GLP-1 analogue or derivative thereof according to any one of embodiments 1-107 for the preparation of a medicament for delaying or preventing disease progression in type 2 diabetes.

113. Use of a GLP-1 analogue or derivative thereof according to any one of embodiments 1-107 for the preparation of a medicament for decreasing food intake, decreasing β-cell apoptosis, increasing β-cell function and β-cell mass, and/or for restoring glucose sensitivity to β-cells.

114. A GLP-1 analogue or derivative thereof according to any one of embodiments 1-107 for use in the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a formulation described herein as comprising a particular element should be understood as also describing a formulation consisting of that element, unless otherwise stated or clearly contradicted by context).

This invention includes all modifications and equivalents of the subject matter recited in the aspects or claims presented herein to the maximum extent permitted by applicable law.

The present invention is further illustrated in the following representative methods and examples which are, however, not intended to limit the scope of the invention in any way.

The features disclosed in the foregoing description and in the following examples may, both separately and in any combination thereof, be material for realising the invention in diverse forms thereof.

EXAMPLES

Abbreviations used:
r.t: Room temperature
DIPEA: diisopropylethylamine
$H_2O$: water
$CH_3CN$: acetonitrile
DMF: NN dimethylformamide
HBTU: 2-(1H-Benzotriazol-1-yl-)-1,1,3,3 tetramethyluronium hexafluorophosphate
Fmoc: 9H-fluoren-9-ylmethoxycarbonyl
Boc: tert butyloxycarbonyl
OtBu: tert butyl ester
tBu: tert butyl
Trt: triphenylmethyl
Pmc: 2,2,5,7,8-Pentamethyl-chroman-6-sulfonyl
Dde: 1-(4,4-Dimethyl-2,6-dioxocyclohexylidene)ethyl
ivDde: 1-(4,4-Dimethyl-2,6-dioxocyclohexylidene)-3-methylbutyl
Mtt: 4-methyltrityl
Mmt: 4-methoxytrityl
DCM: dichloromethane
TIS: triisopropylsilane)
TFA: trifluoroacetic acid
$Et_2O$: diethylether
NMP: 1-Methyl-pyrrolidin-2-one
DIPEA: Diisopropylethylamine
HOAt: 1-Hydroxy-7-azabenzotriazole
HOBt: 1-Hydroxybenzotriazole
DIC: Diisopropylcarbodiimide
DBU: 1,8-diazabicycli-[5,4,0]undecene-7
MW: Molecular weight
A: Synthesis of Resin Bound Peptide
SPPS Method A.

The protected peptidyl resin was synthesized according to the Fmoc strategy on an Applied Biosystems 433 peptide synthesizer in 0.25 mmol or 1.0 mmol scale using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP (N-methylpyrrolidone), and UV monitoring of the deprotection of the Fmoc protection group. The starting resin used for the synthesis of the peptide amides was Rink-Amide resin and either Wang or chlorotrityl resin was used for peptides with a carboxy C-terminal. The protected amino acid derivatives used were standard Fmoc-amino acids (supplied from e.g. Anaspec, or Novabiochem) supplied in preweighed cartridges suitable for the ABI433A synthesizer with the exception of unnatural aminoacids such as Fmoc-Aib-OH (Fmoc-aminoisobutyric acid). The N terminal amino acid was Boc protected at the alpha amino group (e.g. Boc-His(Boc)OH was used for peptides with His at the N-terminal). The epsilon amino group of lysine at position 26 was either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2002/2003 or newer version, or W. R. Sampson (1999), J. Pep. Sci. 5, 403.

SPPS Method B:

One alternative method (method B) of peptide synthesis was by Fmoc chemistry on a microwave-based Liberty peptide synthesizer (CEM Corp., North Carolina). The resin was Tentagel S RAM with a loading of 0.24 mmol/g. The coupling chemistry was DIC/HOAt in NMP using amino acid solutions of 0.3 M in NMP and a molar excess of 8-10 fold. Coupling conditions was 5 minutes at up to 70° C. Deprotection was with 5% piperidine in NMP at up to 70° C. When a chemical modification of a lysine side chain was desired, the lysine was incorporated as Lys(Mtt). The Mtt group was removed by suspending the resin in neat hexafluoroisopropanol for 20 minutes followed by washing with DCM and NMP. The chemical modification of the lysine was performed either by manual synthesis or by one or more automated steps on the Liberty followed by a manual coupling. Another method of peptide synthesis was by Fmoc chemistry on an ABI 433 with HBTU coupling. After synthesis the resin was washed with DCM and dried, and the peptide was cleaved from the resin by a 2 hour treatment with TFA/TIS/water (92.5/5/2.5) followed by precipitation with diethylether. the peptide was redissolved in 30% acetic acid or similar solvent and purified by standard RP-HPLC on a C18 column using acetonitrile/TFA. The identity of the peptide was confirmed by MALDI-MS.

SPPS Method C

The protected peptidyl resin was synthesized according to the Fmoc strategy on an Advanced ChemTech Synthesiser (APEX 348) 0.25 mmol scale using the manufacturer supplied protocols which employ DIC (dicyclohexylcarbodiimide) and HOBt (1-Hydroxybenzotriazole) mediated couplings in NMP (N-methylpyrrolidone). The starting resin used for the synthesis of the peptide amides was Rink-Amide resin and either Wang or chlorotrityl resin was used for peptides with a carboxy C-terminal. The protected amino acid derivatives used were standard Fmoc-amino acids (supplied from e.g. Anaspec, or Novabiochem. The N terminal amino acid was Boc protected at the alpha amino group (e.g. Boc-His(Boc)OH was used for peptides with His at the N-terminal). The epsilon amino group of lysine at position 26 was either protected with Mtt, Mmt, Dde, ivDde, or Boc, depending on the route for attachment of the albumin binding moiety and spacer. The synthesis of the peptides may in some cases be improved by the use of dipeptides, e.g., pseudoprolines from Novabiochem, Fmoc-Ser(tbu)-ΨSer(Me,Me)-OH, see e.g. catalogue from Novobiochem 2002/2003 or newer version, or W. R. Sampson (1999), J. Pep. Sci. 5, 403

Procedure for Removal of ivDde or Dde-Protection.

The resin (0.25 mmol) was placed in a manual shaker/filtration apparatus and treated with 2% hydrazine in N-methylpyrrolidone (20 ml, 2×12 min) to remove the Dde or ivDde group and wash with N-methylpyrrolidone (4×20 ml).

Procedure for Removal of Mtt or Mmt-Protection.

The resin (0.25 mmol) was placed in a manual shaker/filtration apparatus and treated with 2% TFA and 2-3% TIS in DCM (20 ml, 5-10 min repeated 6-12 times) to remove the Mtt or Mmt group and wash with DCM (2×20 ml), 10% MeOH and 5% DIPEA in DCM (2×20 ml) and N-methylpyrrolidone (4×20 ml).

Alternative Procedure for Removal of Mtt-Protection:

The resin was placed in a syringe and treated with hexafluoroisopropanol for 2×10 min to remove the Mtt group. The resin was then washed with DCM and NMP as described above.

Procedure for Attachment of Sidechains to Lysine Residue.

The albumin binding residue (B—U-sidechain of formula I) can be attached to the peptide either by acylation to resin bound peptide or acylation in solution to the unprotected peptide using standard acylating reagent such as but not limited to DIC, HOBt/DIC, HOAt/DIC, or HBTU.

Attachment to Resin Bound Peptide:

Route I

Activated (active ester or symmetric anhydride) albumin binding residue (A-B)-sidechain of formula I) such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, dichloromethane, 2-propanol, methanol and diethyl ether.

Route II

The albumin binding residue (A-(B)- sidechain of formula I) was dissolved in N-methyl pyrrolidone/methylene chloride (1:1, 10 ml). The activating reagent such as hydroxybenzotriazole (HOBt) (4 molar equivalents relative to resin) and diisopropylcarbodiimide (4 molar equivalents relative to resin) was added and the solution was stirred for 15 min. The solution was added to the resin and diisopropyethylamine (4 molar equivalents relative to resin) was added. The resin was shaken 2 to 24 hours at room temperature. The resin was washed with N-methyl pyrrolidone (2×20 ml), N-methylpyrrolidone/Methylene chloride (1:1) (2×20 ml) and methylene chloride (2×20 ml).

Route III

Activated (active ester or symmetric anhydride) albumin binding residue (A-B- sidechain of formula I) such as octadecanedioic acid mono-(2,5-dioxo-pyrrolidin-1-yl)ester (Ebashi et al. EP511600, 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the albumin binding residue such as tert.-butyl, the reaction mixture was lyophilized O/N and the isolated crude peptide deprotected afterwards—in case of a tert-butyl group the peptide was dissolved in a mixture of trifluoroacetic acid, water and triisopropylsilane (90:5:5). After for 30 min the mixture was, evaporated in vacuo and the finale peptide purified by preparative HPLC.

Procedure for Removal of Fmoc-Protection:

The resin (0.25 mmol) was placed in a filter flask in a manual shaking apparatus and treated with N-methylpyrrolidone/methylene chloride (1:1) (2×20 ml) and with N-methylpyrrolidone (1×20 ml), a solution of 20% piperidine in N-methylpyrrolidone (3×20 ml, 10 min each). The resin was washed with N-methylpyrrolidone (2×20 ml), N-methylpyrrolidone/Methylene chloride (1:1) (2×20 ml) and methylene chloride (2×20 ml).

Procedure for Cleaving the Peptide Off the Resin:

The peptide was cleaved from the resin by stirring for 180 min at room temperature with a mixture of trifluoroacetic acid, water and triisopropylsilane (95:2.5:2.5 to 92:4:4). The cleavage mixture was filtered and the filtrate was concentrated to an oil by a stream of nitrogen. The crude peptide was precipitated from this oil with 45 ml diethyl ether and washed 1 to 3 times with 45 ml diethyl ether.

Purification:

The crude peptide was purified by semipreparative HPLC on a 20 mm×250 mm column packed with either 5μ or 7μ C-18 silica. Depending on the peptide one or two purification systems were used.

TFA: After drying the crude peptide was dissolved in 5 ml 50% acetic acid $H_2O$ and diluted to 20 ml with $H_2O$ and injected on the column which then was eluted with a gradient of 40-60% $CH_3CN$ in 0.1% TFA 10 ml/min during 50 min at 40° C. The peptide containing fractions were collected. The purified peptide was lyophilized after dilution of the eluate with water.

Ammonium sulphate: The column was equilibrated with 40% $CH_3CN$ in 0.05M $(NH_4)_2SO_4$, which was adjusted to pH 2.5 with concentrated $H_2SO_4$. After drying the crude peptide was dissolved in 5 ml 50% acetic acid $H_2O$ and diluted to 20 ml with $H_2O$ and injected on the column which then was eluted with a gradient of 40%-60% $CH_3CN$ in 0.05M $(NH_4)_2SO_4$, pH 2.5 at 10 ml/min during 50 min at 40° C. The peptide containing fractions were collected and diluted with 3 volumes of $H_2O$ and passed through a Sep-Pak® C18 cartridge (Waters part. #:51910) which has been equilibrated with 0.1% TFA. It was then eluted with 70% $CH_3CN$ containing 0.1% TFA and the purified peptide was isolated by lyophilisation after dilution of the eluate with water.

The final product obtained was characterised by analytical RP-HPLC (retention time) and by LCMS The RP-HPLC analysis may be performed using UV detection at 214 nm and e.g. a Vydac 218TP54 4.6 mm×250 mm 5μ C-18 silica column (The Separations Group, Hesperia, USA) and eluted at e.g. 1 ml/min at 42° C. Most often one of following specific conditions were used:

Method 03_A1_1

HPLC (Method 03_A1_1): The RP-analysis was performed using a Waters 2690 systems fitted with a Waters 996 diode array detector. UV detections were collected at 214, 254, 276, and 301 nm on a 218TP54 4.6 mm×250 mm 5μ C-18 silica column (The Seperations Group, Hesperia), which was eluted at 1 ml/min at 42° C. The column was equilibrated with 10% of a 0.5 M ammonium sulfate, which was adjusted to pH 2.5 with 4M sulfuric acid. After injection, the sample was eluted by a gradient of 0% to 60% acetonitrile in the same aqueous buffer during 50 min.

Method 03_B1_2

HPLC (Method 03_B1_2): The RP-analysis was performed using a Waters 2690 systems fitted with a Waters 996 diode array detector. UV detections were collected at 214, 254, 276, and 301 nm on a Zorbax 300SB C-18 (4.5×150 mm, 5μ), which was eluted at 0.5 ml/min at 42° C. The column was equilibrated with an aqueous solution of TFA in water (0.1%). After injection, the sample was eluted by a gradient of 0% to 60% acetonitrile (+0.1% TFA) in an aqueous solution of TFA in water (0.1%) during 50 min.

Method 02_B1_1

HPLC (Method 02_B1_1): The RP-analyses was performed using a Alliance Waters 2695 system fitted with a Waters 2487 dualband detector. UV detections at 214 nm and 254 nm were collected using a Vydac 218TP53, C18, 300 Å, 5 um, 3.2 mm×250 mm column, 42° C. Eluted with a linear gradient of 0-60% acetonitrile, 95-35% water and 5% trifluoroacetic acid (1.0%) in water over 50 minutes at a flow-rate of 0.50 ml/min.

Method 01_B4_2

HPLC (Method 01_B4_2): RP-analyses was performed using a Waters 600S system fitted with a Waters 996 diode array detector. UV detections at 214 nm and 254 nm were collected using a Symmetry300 C18, 5 um, 3.9 mm×150 mm column, 42° C. Eluted with a linear gradient of 5-95% acetonitrile, 90-0% water, and 5% trifluoroacetic acid (1.0%) in water over 15 minutes at a flow-rate of 1.0 min/min.

Method 02_B4_4

HPLC (Method 02_B4_4): The RP-analyses was performed using a Alliance Waters 2695 system fitted with a Waters 2487 dualband detector. UV detections at 214 nm and 254 nm were collected using a Symmetry300 C18, 5 um, 3.9 mm×150 mm column, 42° C. Eluted with a linear gradient of 5-95% acetonitrile, 90-0% water, and 5% trifluoroacetic acid (1.0%) in water over 15 minutes at a flow-rate of 1.0 min/min.

Method 02_B6_1

HPLC (Method 02_B6_1): The RP-analyses was performed using a Alliance Waters 2695 system fitted with a Waters 2487 dualband detector. UV detections at 214 nm and 254 nm were collected using a Vydac 218TP53, C18, 300 Å, 5 um, 3.2 mm×250 mm column, 42° C. Eluted with a linear gradient of 0-90% acetonitrile, 95-5% water, and 5% trifluoroacetic acid (1.0%) in water over 50 minutes at a flow-rate of 0.50 ml/min.

Method 03_B6_1

HPLC (Method 03_B1_1): The RP-analysis was performed using a Waters 2690 systems fitted with a Waters 996 diode array detector. UV detections were collected at 214, 254, 276, and 301 nm on a 218TP54 4.6 mm×250 mm 5μ C-18 silica column (The Seperations Group, Hesperia), which was eluted at 1 ml/min at 42° C. The column was equilibrated with 5% acetonitrile (+0.1% TFA) in an aqueous solution of TFA in water (0.1%). After injection, the sample was eluted by a gradient of 0% to 90% acetonitrile (+0.1% TFA) in an aqueous solution of TFA in water (0.1%) during 50 min.

HPLC (Method I_BDSB2):

Buffer A: 10 mM tris, 15 mM (NH4)2SO4, pH adjusted to 7.3 with 4NH2SO4, 20% v/v acetonitrile Buffer B: 80% v/v acetonitrile Flow: 1.0 ml/min Gradient: 0-20 min 10-50% B Column: Phenomenex, Jupiter 4.6 mm×150 mm, C4, 5μ, 300 Å

Column temperature: 40° C.

Alternatively a preparative gradient elution can be performed as indicated above and the percentage of acetonitrile where the compound elutes is noted. Identity is confirmed by MALDI.

The following instrumentation was used:

LCMS was performed on a setup consisting of Sciex API 100 Single quadropole mass spectrometer, Perkin Elmer Series 200 Quard pump, Perkin Elmer Series 200 autosampler, Applied Biosystems 785A UV detector, Sedex 75 evaporative light scattering detector The instrument control and data acquisition were done by the Sciex Sample control software running on a Windows 2000 computer.

The HPLC pump is connected to two eluent reservoirs containing:

A: 0.05% Trifluoro acetic acid in water

B: 0.05% Trifluoro acetic acid in acetonitrile

The analysis is performed at room temperature by injecting an appropriate volume of the sample (preferably 20 μl) onto the column which is eluted with a gradient of acetonitrile.

The HPLC conditions, detector settings and mass spectrometer settings used are giving in the following table.

Column: Waters Xterra MS C-18×3 mm id 5 μm

Gradient: 5%-90% acetonitrile linear during 7.5 min at 1.5 ml/min

Detection: 210 nm (analogue output from DAD)

ELS (analogue output from ELS), 40° C.

MS ionisation mode API-ES

Alternatively LCMS was performed on a setup consisting of Hewlett Packard series 1100 G1312A Bin Pump, Hewlett Packard series 1100 Column compartment, Hewlett Packard series 1100 G1315A DAD diode array detector, Hewlett Packard series 1100 MSD and Sedere 75 Evaporative Light Scattering detector controlled by HP Chemstation software. The HPLC pump is connected to two eluent reservoirs containing:

A: 10 mM $NH_4OH$ in water

B: 10 mM $NH_4OH$ in 90% acetonitrile

The analysis was performed at 23° C. by injecting an appropriate volume of the sample (preferably 20 μl) onto the column which is eluted with a gradient of A and B.

The HPLC conditions, detector settings and mass spectrometer settings used are giving in the following table.

Column Waters Xterra MS C-18×3 mm id 5 μm

Gradient 5%-100% acetonitrile linear during 6.5 min at 1.5 ml/min

Detection 210 nm (analogue output from DAD)

ELS (analogue output from ELS)

MS ionisation mode API-ES. Scan 100-1000 amu step 0.1 amu

MALDI-MS:

Molecular weights of the peptides were determined using matrix-assisted laser desorption time of flight mass spectroscopy (MALDI-MS), recorded on a Microflex (Bruker). A matrix of α-cyano-4-hydroxy cinnamic acid was used.

Analytical HPLC Conditions (Method I):

Equilibration of the column (Xterra TM MS C18, 5 um, 4.6×150 mm Column, P7N 186 000490) with 0.1% TFA/$H_2O$ and elution by a gradient of 0% $CH_3CN$/0.1% TFA/$H_2O$ to 60% $CH_3CN$/0.1% TFA/$H_2O$ during 25 min followed by a gradient from 60% to 100% over 5 min.

In the examples of this invention the nomenclature and structurally graphics is meant as:

One letter symbols for the natural amino acids is used, e.g. H is L-histidine, A is L-alanine etc. Three letter abbreviations for amino acids may also be uses, e.g. His is L-histidine, Ala is L-alanine etc. For non natural amino acids three letter abbreviations are used, such as Aib for aminoisobutyric acid. The position of the amino acids may either be indicated with a number in superscript after the amino acid symbols such as $Lys^{33}$, or as Lys33. The N-terminal amino group may be symbolised either as $NH_2$ or as H. The C-terminal carboxylic group may be symbolised either as —OH or as —COOH. The C-terminal amide group is symbolised as —$NH_2$ The sub-structures

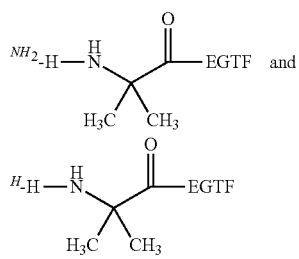

both means His-Aib-Glu-Gly-Thr-Phe.

The epsilon amino group of Lysine may be described either as the greek symbol ε or spelled "epsilon".

The structures in the examples below are in several cases a combination of one letter symbols for the naturally amino acids combined with the three letter abbreviation Aib for aminoisobutyric acid. In several cases some of the amino acids are shown in expanded full structure. Thus lysine that has been derivatised may be shown as the expanded full structures as in example 2 where the lysine at position 20 is expanded. The nitrogen (with indicated H) between tyrosine at position 19 and the expanded lysine at position 20 is thus the nitrogen of the peptide bond connecting the two amino acids in example 2 According to the procedure above, the following derivatives were prepared as non-limiting examples of the invention:

Example 1

[Glu22,Arg26]GLP-1 (7-33) Amide $^H$—H A E G T F T S D V S S Y L E E Q A A R E F I A W L V—$NH_2$ Preparation Method: B The peptide was eluted at 64% acetonitrile.
Structure confirmed by MALDI-MS
Calculated MW=3056.4

Example 2

N Epsilon20 {2-(2-{2-[2-(2-{2-[4-Carboxy-4-(17-carboxy-heptadecanoylamino)butyrylamino] ethoxy}ethoxy)acetylamino]ethoxy}ethoxy)acetyl}-(Aib8,Lys20,Glu22,Val25,Arg26,Leu27, lu30, Lys33)GLP-1(7-33)amide Preparation method: Method C except that the peptide was prepared on an Apex396 from Advanced Chemtech using a molar excess of 8-10 fold amino acid, DIC and HOAt/HOBt (1:1) and the Mtt group was deprotected with hexafluoroisopropanol. The final product was characterized by analytical HPLC and MALDI-MS.

HPLC (METHOD 02_B6_1):

RT=32 min

MALDI-MS=3901

Calculated MW=3900.5

Example 3

N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Arg26,Glu30) GLP-1(7-33) amide

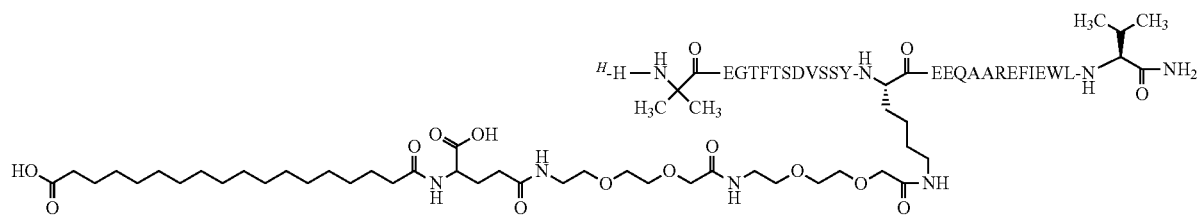

Preparation method: Method C except that the peptide was prepared on an Apex396 from Advanced Chemtech using a molar excess of 8-10 fold amino acid, DIC and HOAt/HOBt (1:1) and the Mtt group was deprotected with hexafluoroisopropanol. The final product was characterized by analytical HPLC and MALDI-MS.

HPLC (METHOD 02_B6_1):
RT=32.9 min
MALDI-MS=3858.7
Calculated MW=3859.3

Example 4

[Glu22, Val25, Arg26] GLP-1 (7-33)amide $^{NH_2}$—H A E G T F T S D V S S Y L E E Q A V R E F I A W L V—NH$_2$ Preparation Method: A
HPLC (METHOD 03_A1_1)
RT=44.6 min
LCMS: m/z=1029.2 (M+3H)$^{3+}$
Calculated MW=3084.4

Example 5

[Aib8,Lys20,Glu22,Val25,Arg26,Glu30] GLP-1 (7-33) Amide $^H$-H—N(Aib)—EGTFTSDVSSYKEEQAVREFIEWLV-NH$_2$ Preparation Method: B
The peptide was eluted at 60% acetonitrile.
Structure confirmed by MALDI-MS
Calculated MW=3171.5

Example 6

N Epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-[Aib8,Lys20,Glu22,Val25,Arg26,Glu30] GLP-1 (7-33) amide

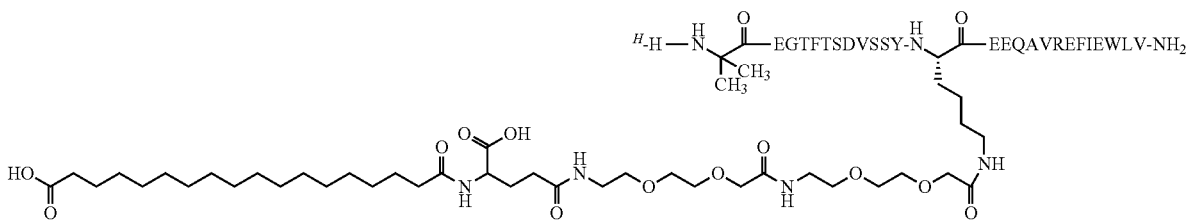

Preparation Method: B
The peptide was eluted at 70% acetonitrile.
Structure confirmed by MALDI-MS
Calculated MW=3887.4

Example 7

[Glu22, Arg26]GLP-1(7-33)peptide $^{H}$—H A E G T F T S D V S S Y L E E Q A A R E F I A W L V-$^{OH}$ Preparation Method: A
HPLC (method B6):
RT=28.09 min LCMS: m/z=1020 (M+3H)$^{3+}$
Calculated MW=3057.3

Example 8

[Glu22,Val25,Arg26] GLP-1 (7-32)amide $^{NH_2}$—H A E G T F T S D V S S Y L E E Q A V R E F I A W L-NH$_2$ Preparation Method: A
HPLC (METHOD 03_A1_1)
RT=41.9 min
LCMS: m/z=996.0 (M+3H)$^{3+}$
Calculated MW=2985.3

Example 9

N-epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Arg26) GLP-1(7-33) amide

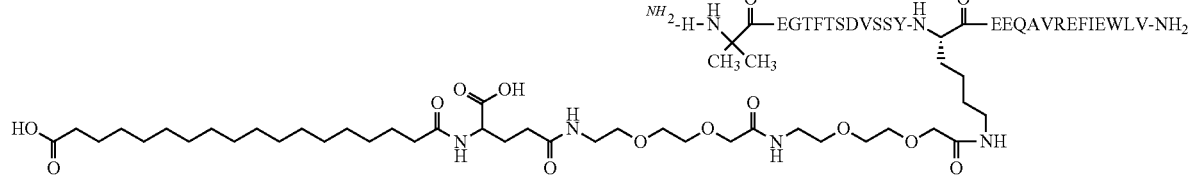

Preparation method: Method C except that the peptide was prepared on an Apex396 from Advanced Chemtech using a molar excess of 8-10 fold amino acid, DIC and HOAt/HOBt (1:1) and the Mtt group was deprotected with hexafluoroisopropanol. The final product was characterized by analytical HPLC and LC-MS.
HPLC (METHOD 02_B6_1):
RT=34.31 MIN
LCMS: m/z=1277 (M+3H)$^{3+}$
Calculated MW=3831

Example 10

N-epsilon31 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Glu22,Val25,Arg26,Lys31) GLP-1(7-33) amide

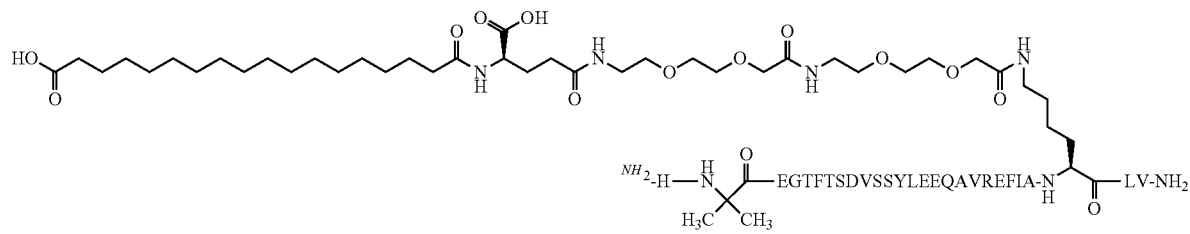

Preparation method: Method C except that the peptide was prepared on an Apex396 from Advanced Chemtech using a molar excess of 8-10 fold amino acid, DIC and HOAt/HOBt (1:1) and the Mtt group was deprotected with hexafluoroisopropanol. The final product was characterized by analytical HPLC and LC-MS.
HPLC (METHOD 02_B6_1):

RT=34.02 MIN

LCMS: m/z=1253 (M+3H)$^{3+}$

Calculated MW=3759

Example 11

N-epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(DesaminoHis7,Lys20,Glu22,Arg26) GLP-1(7-33) amide

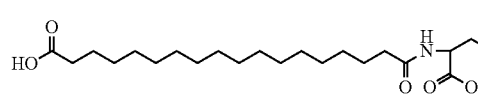
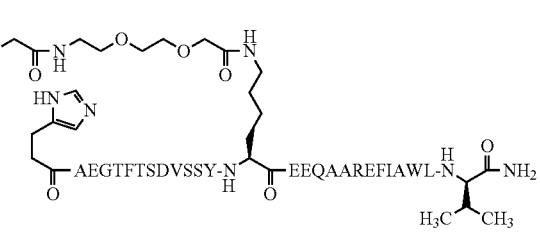

Preparation method: Method C except that the peptide was prepared on an Apex396 from Advanced Chemtech using a molar excess of 8-10 fold amino acid, DIC and HOAt/HOBt (1:1) and the Mtt group was deprotected with hexafluoroisopropanol. The final product was characterized by analytical HPLC and LC-MS.

HPLC (METHOD 02_B6_1):
RT=33.3 MIN
LCMS: m/z=1257.7 (M+3H)$^{3+}$
Calculated MW=3773

Example 12

N-epsilon31 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(DesaminoHis7,Glu22,Arg26,Lys31)GLP-1(7-33) amide

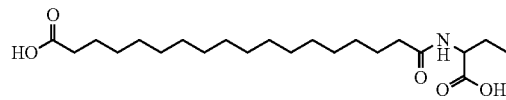

Preparation method: Method C except that the peptide was prepared on an Apex396 from Advanced Chemtech using a molar excess of 8-10 fold amino acid, DIC and HOAt/HOBt (1:1) and the Mtt group was deprotected with hexafluoroisopropanol. The final product was characterized by analytical HPLC and LC-MS.

HPLC (METHOD 02_B6_1):
RT=33.2 MIN
LCMS: m/z=1233.9 (M+3H)$^{3+}$
Calculated MW=3699

Example 13

N-epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Val25,Arg26,Leu27,Glu30,Lys31)GLP-1(7-32) amide

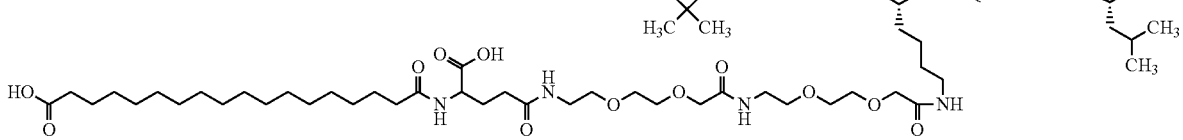

Preparation method: Method C except that the peptide was prepared on an Apex396 from Advanced Chemtech using a molar excess of 8-10 fold amino acid, DIC and HOAt/HOBt (1:1) and the Mtt group was deprotected with hexafluoroisopropanol. The final product was characterized by analytical HPLC and MALDI-MS.

HPLC (METHOD 02_B6_1):
RT=32.6 MIN
MALDI-MS: 3715.5
Calculated MW=3714.3

Example 14

N-epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8, Lys20,Glu22,Val25,Arg26,Leu27,Nle30, Lys31)GLP-1(7-32) amide

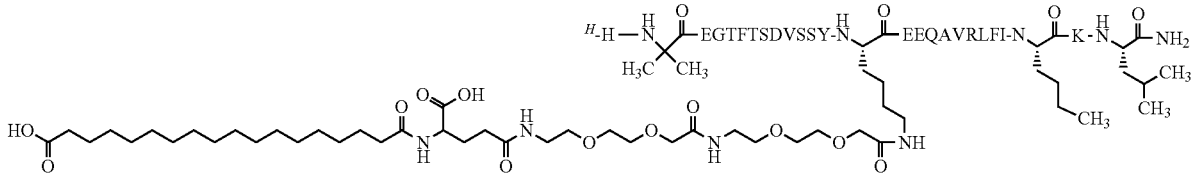

Preparation method: Method C except that the peptide was prepared on an Apex396 from Advanced Chemtech using a molar excess of 8-10 fold amino acid, DIC and HOAt/HOBt (1:1) and the Mtt group was deprotected with hexafluoroisopropanol. The final product was characterized by analytical HPLC and MALDI-MS.

HPLC (METHOD 02_B6_1):
RT=33 MIN
MALDI-MS: 3696.9
Calculated MW=3698

Example 15

N-epsilon31-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl]-[Aib8,Glu22,Val25,Arg26,Lys31]GLP-1-(7-33) amide

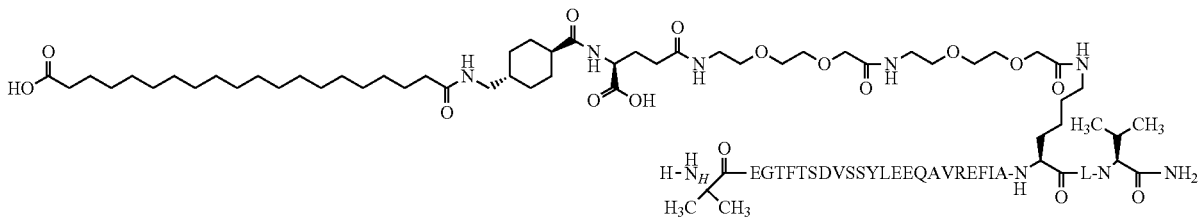

Preparation method: Method C except that the peptide was prepared on an Apex396 from Advanced Chemtech using a molar excess of 8-10 fold amino acid, DIC and HOAt/HOBt (1:1) and the Mtt group was deprotected with hexafluoroisopropanol. The final product was characterized by analytical HPLC and MALDI-MS.

HPLC (METHOD 02_B6_1):
RT=39.3 MIN
MALDI-MS: 3696.9
Calculated MW=3698

Example 16

[Desamino His7,Glu22,Arg26]-GLP-1 (7-34)

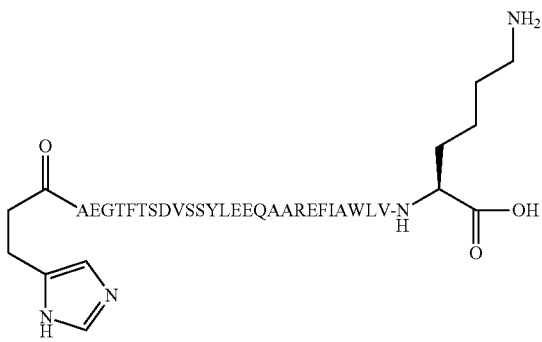

HPLC (METHOD I_BDSB2)
RT=5.65 min
LCMS: m/z=1057.5 (M+3H)$^{3+}$
Calculated MW=3170.5

Example 17

[Aib8,Lys20,Glu22,Val25,Arg26,Leu27,Lys31]GLP-1 (7-32) amide

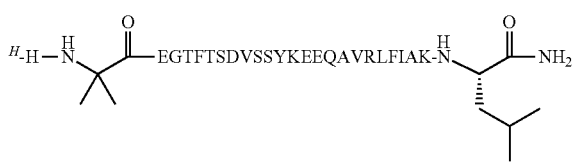

Preparation analogous to SPPS Method B.
HPLC method 02_B6_1:
RT=27.09 min
LCMS: m/z=735 (M+4H)$^{4+}$
Calculated (M)=2940.3

Example 18

N-epsilon31-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][DesaminoHis7,Asp11,Glu18,Glu22,Val25,Arg26,Asp27,Glu30,Lys31]GLP-1 (7-33)-peptide amide Preparation method B on ChemMatrix Rink Amide resin (0.24 mmol/g, 0.4 g).

HPLC (02_B4_4): Rt=10.649 min; 99.6% purity

HPLC (03_A3_1): Rt=8.491 min; 94.3% purity

MALDI-MS: alpha-cyano-4-hydroxycinnamic acid; m/z: 3824.543 (NEGATIVE MODE)

Example 19

[Aib8,Glu22,Val25,Lys31]GLP-1(7-33)-amide

Preparation method: The peptide was prepared by SPPS Method C and the final product was characterized by analytical HPLC and MALDI-MS.

HPLC (02-B6-1): RT=31.5 min

HPLC (04-A3-1): RT=8.6 min

MALDI-MS: 3043.6

Calculated MW=3040.4

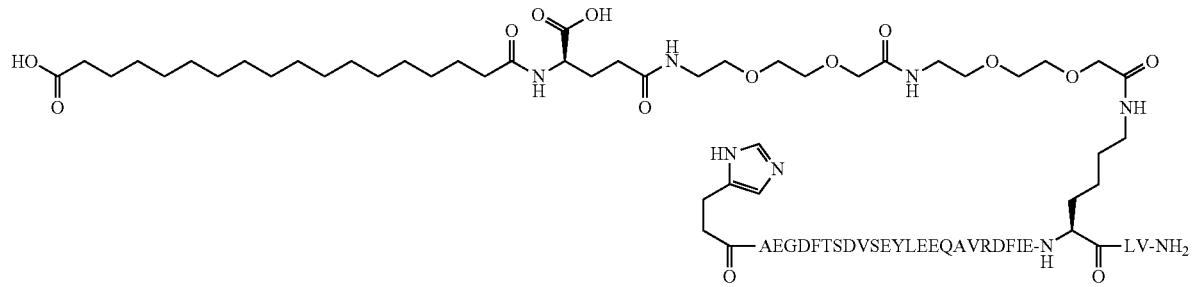

Example 20

N-epsilon31-{2-(2-{2-[2-(2-{2-[4-Carboxy-4-(17-carboxy-heptadecanoylamino)butyrylamino]ethoxy}ethoxy)acetylamino]ethoxy}ethoxy)acetyl}-N-beta34-(2-(bis-carboxymethylamino)acetyl)[Aib8,Glu22,Val25,Arg26,Lys31,Dap34] GLP-1(7-34) amide Preparation method: The peptide was prepared by SPPS Method C and the final product was characterized by analytical HPLC and MALDI-MS.
HPLC (02-B6-1): RT=36.7 min
HPLC (A4-A3-1): RT=8.9 min
MALDI-MS: 4015.9
Calculated MW=4015.5

Biological Findings
Protraction of GLP-1 Derivatives after i.v. or s.c. Administration The protraction of a number GLP-1 compounds of the invention is determined by monitoring the concentration thereof in plasma after sc administration to healthy pigs, using the methods described below. For comparison also the concentration in plasma of GLP-1(7-37) after sc. administration is followed. The protraction of other GLP-1 compounds of the invention can be determined in the same way.

Pharmacokinetic Testing of GLP-1 Analogues in Minipigs

The test substances are dissolved in a vehicle suitable for subcutaneous or intravenous administration. The concentration is adjusted so the dosing volume is approximately 1 ml.

The study is performed in 12 male Göttingen minipigs from Ellegaard Göttingen Minipigs ApS. An acclimatisation period of approximately 10 days is allowed before the animals enter the study. At start of the acclimatisation period the minipigs are about 5 months old and in the weight range of 8-10 kg.

The study is conducted in a suitable animal room with a room temperature set at 21-23° C. and the relative humidity to ≥50%. The room is illuminated to give a cycle of 12 hours light and 12 hours darkness. Light is from 06.00 to 18.00 h.

The animals are housed in pens with straw as bedding, six together in each pen.

The animals have free access to domestic quality drinking water during the study, but are fasted from approximately 4 pm the day before dosing until approximately 12 hours after dosing.

The animals are weighed on arrival and on the days of dosing.

The animals receive a single intravenous or subcutaneous injection. The subcutaneous injection is given on the right side of the neck, approximately 5-7 cm from the ear and 7-9 cm from the middle of the neck. The injections are given with a stopper on the needle, allowing 0.5 cm of the needle to be introduced.

Each test substance is given to three animals. Each animal receives a dose of 2 nmol/kg body weight.

Six animals are dosed per week while the remaining six are rested.

A full plasma concentration-time profile is obtained from each animal. Blood samples are collected according to the following schedule:

After Intravenous Administration:
Predose (0), 0.17 (10 minutes), 0.5, 1, 2, 4, 6, 8, 12, 24, 48, 72, 96, and 120 hours after injection.

After Subcutaneous Administration:
Predose (0), 0.5, 1, 2, 4, 6, 8, 12, 24, 48, 72, 96, and 120 hours after injection.

At each sampling time, 2 ml of blood is drawn from each animal. The blood samples are taken from a jugular vein.

The blood samples are collected into test tubes containing a buffer for stabilisation in order to prevent enzymatic degradation of the GLP-1 compounds.

Plasma is immediately transferred to Micronic-tubes. Approximately 200 µl plasma is transferred to each Micronic-tube. The plasma is stored at −20° C. until assayed. The plasma samples are assayed for the content of GLP-1 compounds using an immunoassay.

The plasma concentration-time profiles are analysed by a non-compartmental pharmacokinetic analysis. The following pharmacokinetic parameters are calculated at each occasion: AUC, AUC/Dose, $AUC_{\%\ Extrap}$, $C_{max}$, $t_{max}$, $\lambda_z$, $t_{1/2}$, CL, CL/f, $V_z$, $V_z/f$ and MRT.

Selected compounds of the invention are tested in Danish Landrace pigs.

Pharmacokinetic Testing of GLP-1 Compounds in Pigs

Pigs (50% Duroc, 25% Yorkshire, 25% Danish Landrace, app 40 kg) are fasted from the beginning of the experiment. To each pig 0.5 nmol of test compound per kg body weight is administered in a 50 µM isotonic solution (5 mM phosphate, pH 7.4, 0.02% Tween®-20 (Merck), 45 mg/ml mannitol (pyrogen free, Novo Nordisk). Blood samples are drawn from a catheter in vena jugularis. 5 ml of the blood samples are poured into chilled glasses containing 175 µl of the following solution: 0.18 M EDTA, 15000 KIE/ml aprotinin (Novo Nordisk) and 0.30 mM Valine-Pyrrolidide (Novo Nordisk), pH 7.4. Within 30 min, the samples are centrifuged for 10 min at 5-6000*g. Temperature is kept at 4° C. The supernatant is pipetted into different glasses and kept at minus 20° C. until use.

The plasma concentrations of the peptides are determined in a sandwich ELISA or by RIA using different mono- or polyclonal antibodies. Choice of antibodies depends of the GLP-1 compounds. The time at which the peak concentration in plasma is achieved varies within wide limits, depending on the particular GLP-1 compound selected.

General Assay Protocol for Sandwich ELISA in 96-Wells Microtiterplate

Coating buffer (PBS): Phosphate buffered saline, pH7.2

Wash-buffer (PBS-wash): Phosphate buffered saline, 0.05% v/v Tween 20, pH 7.2

Assay-buffer (BSA-buffer): Phosphate buffered saline, 10 g/l Bovin Serum Albumin
(Fluka 05477), 0.05% v/v Tween 20, pH 7.2

Streptavidin-buffer Phosphate buffered saline, 0.5 M NaCl, 0.05% v/v Tween 20, pH 7.2

Standard: Individual compounds in a plasma-matrix

A-TNP: Nonsens antibody

AMDEX: Streptavin-horseradish-peroxodase (Amersham RPN4401V)

TMB-substrate: 3,3',5,5'tetramethylbenzidine (<0.02%), hydrogen peroxide

The assay is carried out as follows (volume/well):

1.) coat with 100 µl catching antibody 5 µg/ml in PBS-buffer
incubate o/n, 4° C.
5×PBS-wash
blocked with last wash in minimum 30 minute
then empty the plate 2.) 20 µl sample+100 µl biotinylated detecting antibody 1 µg/ml in BSA-buffer with 10 µg/ml A-TNP
incubate 2 h, room temperature, on a shaker 5×PBS-wash, then empty the plate 3.) 100 µl AMDEX 1:8000 in Streptavidin-buffer
incubate 45-60 minute, room temperature, on a shaker
5×PBS-wash, then empty the plate 4.) 100 µl TMB-substrate
incubate x minute at room temperature on a shaker
stop the reaction with 100 µl 4 M $H_3PO_4$
Read the absorbance at 450 nm with 620 nm as reference The concentration in the samples is calculated from standard curves.

General Assay Protocol for RIA

DB-buffer: 80 mM phosphate buffer, 0.1% Human serum albumin, 10 mM EDTA,
0.6 mM thiomersal, pH 7.5

FAM-buffer: 40 mM phosphate buffer, 0.1% Human Serum Albumin,
0.6 mM thiomersal, pH 7.5

Charcoal: 40 mM phosphate buffer, 0.6 mM thiomersal, 16.7% bovine plasma, 15 g/l activated carbon, pH 7.5 (mix the suspension minimum 1 h before use at 4° C.)

Standard: Individual compounds in a plasma-matrix

The assay is carried out in minisorp tubes 12×75 mm (volumen/tube) as follows:

Mix—incubate 30 min at 4° C.—centrifuge at 3000 rpm, 30 min—immediately after transfer supernatants to new tubes, close with stopper and count on gamma-counter for 1 minute.

The concentration in the samples is calculated from individual standard curves.

GLP-1 Radio Receptor Assay (RRA):

The method is a radiometric-ligand binding assay using LEADseeker imaging particles. The assay is composed of membrane fragments containing the GLP-1 receptor, unlabeled GLP-1 analogues, human GLP-1 labelled with $^{125}I$ and PS LEADseeker particles coated with wheat germ agglutinin (WGA). Cold and $^{125}I$-labelled GLP-1 will compete for the binding to the receptor. When the LEADseeker particles are added they will bind to carbohydrates residues on the membrane fragments via the WGA-residues. The proximity between the $^{125}I$-molecules and the LEADseeker particles causes light emission from the particles. The LEADseeker will image the emitted light and it will be reversibly correlated to the amount of GLP-1 analogue present in the sample.

Reagents & Materials:

Pre Treatment of Animal Plasma:

Animal plasma is heat treated for 4 hrs at 56° C. and centrifuged at 10.000 rpm for 10 minutes. Afterwards, Val-Pyr (10 µM) and aprotenin (500 KIE/mL) is added and stored at <−18° C. until use.

GLP-1 Analogues Calibrators:

GLP-1 analogues are spiked into heat-treated plasma to produce dilution lines ranging from approximately 1 µM to 1 pM.

GLP-1 RRA Assay Buffer:

25 mM Na-HEPES (pH=7.5), 2.5 mM $CaCl_2$, 1 mM $MgCl_2$, 50 mM NaCl, 0.1% ovalbumin, 0.003% tween 20, 0.005% bacitracin, 0.05% $NaN_3$.

GLP-1 Receptor Suspension:

GLP-1 receptor membrane fragments are purified from baby hamster kidney (BHK) cells stably expressing the human pancreatic GLP-1 receptor. Stored <−80° C. until use.

WGA-Coupled Polystyrene LEADseeker Imaging Beads (RPNQ0260, Amersham):

The beads are reconstituted with GLP-1 RRA assay buffer to a concentration of 13.3 mg/mL. The GLP-1 receptor membrane suspension is then added and incubated cold

|  | Db-buffer | SAMPLE | Antibody | FAM-buf. | Tracer | Charcoal | $H_2O$ |
|---|---|---|---|---|---|---|---|
| Day 1 | | | | | | | |
| Total | | | | 100 µL | | | |
| NSB | 330 µL | | 100 µL | | | | |
| Sample | 300 µL | 30 µL | 100 µL | | 100 µL | | |
| Mix, incubate o/n at 4° C. | | | | | | | |
| Day 2 | | | | | | | |
| Total | | | | | | | 1.5 mL |
| NSB | | | | | | 1.5 mL | |
| Sample | | | | | | 1.5 mL | |

(2-8° C.) at end-over-end for at least 1 hr prior to use.
[$^{125}$I]-GLP-1(7-36)amide (Novo Nordisk A/S).
   Stored <−18° C. until use.
Ethanol 99.9% Vol (De Dansk Spritfabrikker A/S):
   Stored <−18° C. until use.
MultiScreen® Solvinert 0.45 μm Hydrophobic PTFE Plates (MSRPN0450, Millipore Corp.)
Poly Propylene Plates (Cat. No. 650201, Greiner Bio-One)
White Polystyrene 384-Well Plates (Cat. No. 781075, Greiner Bio-One)
Apparatus:
Horizontal Plate Mixer
   Centrifuge with a standard swinging-bucket microtitre plate rotor assembly
UltraVap—Drydown Sample Concentrator (Porvair)
LEADseeker™ Multimodality Imaging System (Amersham)
Assay Procedure:
Sample Preparation:
   Mount the MultiScreen® Solvinert filter plate on a chemical-comparable receiver plate (i.e. poly propylene plates) to collect the filtrate.
   Add 150 μL ice-cold ethanol 99.9% into the empty wells of the MultiScreen® Solvinert filter plate followed by 50 μL calibrator or plasma sample. Place the storage lid on the filter plate.
   Incubate 15 minutes at 18-22° C. on a horizontal plate mixer.
   Place the assembled filter and receiver plate, with the lid, into a standard swinging-bucket microtitre plate rotor assembly. The filtrate is then collected in the empty wells of the receiver plate at 1500 rpm for 2 minutes.
   Dry down the filtrate by using the UltraVap with heated (40° C.) $N_2$ for duration of 15 minutes. Reconstitute the dry material by adding 100 μL GLP-1 RRA assay buffer into each well. Incubate for 5 minutes on a horizontal mixer.
GLP-1 Radio Receptor Assay:
   Use the following pipetting scheme and white polystyrene 384-well plates:
   35 μL GLP-1 RRA assay buffer
   5 μL reconstituted filtrate.
   10 μL [$^{125}$I]-GLP-1(7-36)amide. The stock solution is diluted in GLP-1 RRA assay buffer to 20.000 cpm/well prior to use.
   15 μL GLP-1 receptor membrane fragments (≈0.5 μg/well) pre-coated to WGA-polystyrene LEADseeker imaging beads (0.2 mg/well)
   Seal the plates and incubate over night at 18-22° C.
   The light emission from each wells is detected by using the LEADseeker™ Multimodality Imaging System for duration of 10 minutes.

Example 21

Stimulation of cAMP Formation in a Cell Line Expressing the Cloned Human GLP-1 Receptor The potencies of a number of GLP-1 analogues and derivatives of the invention (the compounds of Examples 1-7, 9-17, and 19-20) were determined as described below, i.e. as the stimulation of the formation of cyclic AMP (cAMP) in a medium containing the human GLP-1 receptor. For comparison, the potency of truncated natural, human GLP-1(7-33) was also determined.

Purified plasma membranes from a stable transfected cell line, BHK467-12A (tk-ts13), expressing the human GLP-1 receptor was stimulated with GLP-1 compound in question, and the potency of cAMP production was measured using the AlphaScreen™ cAMP Assay Kit from Perkin Elmer Life Sciences.

A stable transfected cell line has been prepared at NN A/S, Denmark, and a high expressing clone is selected for screening. The cells are grown at 5% $CO_2$ in DMEM, 5% FCS, 1% Pen/Strep (Penicillin/Streptomycin) and 0.5 mg/ml of the selection marker G418.

Cells at approximate 80% confluence are washed 2× with PBS (Phosphate Buffered Saline) and harvested with Versene (aqueous solution of the tetrasodium salt of ethylenediaminetetraacetic acid), centrifuged 5 min at 1000 rpm and the supernatant removed. The additional steps are all made on ice. The cell pellet is homogenized by the Ultrathurax for 20-30 sec. in 10 ml of Buffer 1 (20 mM Na-HEPES, 10 mM EDTA, pH=7.4), centrifuged 15 min at 20.000 rpm and the pellet resuspended in 10 ml of Buffer 2 (20 mM Na-HEPES, 0.1 mM EDTA, pH=7.4). The suspension is homogenized for 20-30 sec and centrifuged 15 min at 20.000 rpm. Suspension in Buffer 2, homogenization and centrifugation is repeated once and the membranes are resuspended in Buffer 2 and ready for further analysis or stored at −80° C.

The functional receptor assay was carried out by measuring the peptide induced cAMP production by The AlphaScreen Technology. The basic principle of The AlphaScreen Technology is a competition between endogenous cAMP and exogenously added biotin-cAMP. The capture of cAMP is achieved by using a specific antibody conjugated to acceptor beads. Formed cAMP is counted and measured at a Alpha Fusion Microplate Analyzer. The $EC_{50}$ values are calculated using the Graph-Pad Prisme software (version 5).

The truncated natural GLP-1(7-3)) peptide has a very low potency (a high $EC_{50}$ value of 11.3 nM). All tested GLP-1 compounds of the invention had a very high potency (six compounds an $EC_{50}$ below 0.10 nM, six compounds and $EC_{50}$ in the range of 0.10-0.50 nM).

Interestingly, the compounds of Examples 1, 4, 5, and 7, none of which are derivatized, also had an EC50 below 0.30 nM, which is strongly surprising.

Example 22

Binding to the Extracellular Domain of the GLP-1 Receptor

For a number of GLP-1 compounds of the invention (the compounds of Examples 1-17), the affinity of the binding to the isolated N-terminal extracellular domain of the GLP-1R receptor (nGLP-1R) was measured as described below. For comparison, the potency of truncated natural, human GLP-1(7-33) was also determined.

The affinity is a measure of the ability of the GLP-1 derivative in question to displace $^{125}$I-Exendin-4(9-39) from binding to nGLP-1R, and the binding to nGLP-1R was measured in the following assay: The protein nGLP-1R was prepared as described by Runge et al 2007 (Biochemistry, vol. 46, pp. 5830-5840), biotinylated and immobilized on streptavidin-coated SPA beads. The nGLP1R in 0.1M $NaHCO_3$ was biotinylated using 75 μg BNHS (Sigma H1759) to 1 mg protein. The biotinylated nGLP1R was subsequently dialyzed against PBS. All reagents and derivatives were diluted in PBS with 0.05% v/v Tween 20. The binding assay was carried out in 96 well OptiPlates (PerkinElmer 6005290) in a final volume of 200 μl. Each well contained 2 mg streptavidin coated SPA beads (PerkinElmer RPNQ007), 0.1 pmol biotinylated nGLP1R, 50 pCi $^{125}$I-Exendin (9-39) and test peptide in final concentrations ranging from 1000 nM to 0.064 nM. The plates were incubated on a shaker at RT for 3 hours. The SPA particles were spun down by centrifugation for 10 min at 1500 rpm and the plates were counted in a TopCount-NXT (PerkinElmer).

The $IC_{50}$ value is read from the respective curve as the concentration of the GLP-1 compound in question which displaces 50% of $^{125}$I-Exendin-4(9-39) from binding to nGLP-1R.

The affinity of the truncated (natural, human) GLP-1(7-33) to nGLP-1R ($IC_{50}$) was determined to 886 nM. Eleven of the tested GLP-1 compounds of the invention had affinities ($IC_{50}$) below 600 nM (ranging from 20-556 (nM), with six compound below 100 nM. Several GLP-1 compounds of the invention accordingly exhibit a very good binding affinity to the N-terminal GLP-1 receptor (the lower the $IC_{50}$ value, the better the binding). Compounds 1, 4, 5, and 7 which were also discussed in Example 21 had acceptable binding affinities in the range of 200-1500 nM, three of them in the range of 200-600 nM.

Example 23

Affinity to the GLP-1 Receptor

The binding affinity of a number of GLP-1 compounds of the invention (compounds of Examples 1-7, and 9-18) to the human GLP-1 receptor was measured by way of their ability to displace $^{125}$I-GLP-1 from the receptor.
Conditions
Species (in vitro): Hamster
Biological End Point: Receptor Binding
Assay Method: SPA
Receptor: GLP-1 receptor
Cell Line: BHK tk-ts13
Membrane Purification:

The cells (approx. 80% confluence) were washed twice in PBS and harvested (PBS+EDTA or Versene), following which they were separated by centrifugation at 1000 rpm for 5 min. The cells/cell pellet must be kept on ice to the extent possible in the subsequent steps. The cell pellet was homogenised with Ultrathurrax for 20-30 seconds in a suitable amount of Buffer 1 (depending on the amount of cells, but e.g. 10 ml). The homogenate as centrifuged at 20000 rpm for 15 minutes. The pellet was resuspended (homogenised) in 10 ml Buffer 2 and re-centrifuged. This step was repeated once more. The resulting pellet was resuspended in Buffer 2, and the protein concentration was determined. The membranes were stored at −80° C.
Buffer 1: 20 mM Na-HEPES+10 mM EDTA, pH 7.4
Buffer 2: 20 mM Na-HEPES+0.1 mM EDTA, pH 7.4
Binding Assay:
SPA:

Test compounds/peptides, membranes, SPA-particles and [$^{125}$I] are diluted in assay buffer. 25 ul (micro liter) of test compounds/peptides are added to Optiplate. Buffer is added (50 ul). Add 5-10 ug protein/sample (50 ul) corresponding to 0.1-0.2 mg protein/ml (to be preferably optimised for each membrane preparation). Add SPA-particles (Wheatgerm agglutinin SPA beads) RPNQ 0001) 0.5 mg/well (50 ul). Start the incubation with [$I^{125}$]-GLP-1 (final concentration 0.05 nM corresponding to 49.880 DPM, 25 ul). The plates are sealed with PlateSealer. Incubate for 120 minutes at 30° C. while shaking. The plates are centrifuged (1500 rpm, 10 min) and counted in Topcounter.
Assay buffer: 50 mM HEPES
5 mM EGTA
5 mM $MgCl_2$
0.005% Tween 20
pH 7.4

The $IC_{50}$ value is read from the curve as the concentration which displaces 50% of $^{125}$I-GLP-1 from the receptor.

The $IC_{50}$ value of GLP-1(7-33) (truncated natural GLP-1) was 241 nM. Except one compound, all tested compounds of the invention had a better binding to the GLP-1 receptor (i.e. a lower $IC_{50}$ value). Six compounds had a value below 1.00 nM, five compounds in the range from 1-10 nM, and five compounds in the range of 20-200 nM. Compounds 1, 4, 5, and 7 discussed in the previous examples had $IC_{50}$ values in the range of 0.24 nM to 44 nM, and three of them below 2.0 nM.

The invention claimed is:

1. A GLP-1 analogue having a sequence according to formula (I)

Formula (I)
(SEQ ID No: 2)
$Xaa_7-Xaa_8-Xaa_9-Gly-Thr-Phe-Thr-Ser-Asp-Xaa_{16}-$ $Ser-Xaa_{18}-Tyr-Xaa_{20}-Glu-Glu-Xaa_{23}-Xaa_{24}-Xaa_{25}-Arg-$ $Xaa_{27}-Phe-Ile-Xaa_{30}-Xaa_{31}-Leu-Xaa_{33}-Xaa_{34}-Xaa_{35}-R$ wherein
- $Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
- $Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
- $Xaa_9$ is Glu or a Glu derivative such as alpha, alpha dimethyl-Glu;
- $Xaa_{16}$ is Val or Leu;
- $Xaa_{18}$ is Ser, Lys, Cys or Arg;
- $Xaa_{20}$ is Leu, Lys or Cys;
- $Xaa_{23}$ is Gln, Glu, Lys, Cys or Arg;
- $Xaa_{24}$ is Ala or Asn;
- $Xaa_{25}$ is Ala or Val;
- $Xaa_{27}$ is Glu, Ala or Leu;
- $Xaa_{30}$ is Ala, Glu, Lys, Arg or absent;
- $Xaa_{31}$ is Trp, Lys, Cys or absent;
- $Xaa_{33}$ is Val, Lys, Cys or absent;
- $Xaa_{34}$ is Lys, Glu, Asn, Arg, Cys or absent;
- $Xaa_{35}$ is Gly, Aib or absent;
- R is amide or is absent;
- provided that if $Xaa_{30}$, $Xaa_{31}$, Leu at position 32, $Xaa_{33}$, or $Xaa_{34}$ is absent then each amino acid residue downstream is also absent; or
- a derivative of the foregoing analogue where the analogue is derivatised at a Lys or Cys residue with an albumin binding residue or is pegylated.

2. The GLP-1 analogue according to claim 1, wherein the amino acid at position 35 is absent, and wherein the total length of the GLP-1 analogue is 28 amino acids.

3. The GLP-1 analogue according to claim 1, wherein the amino acids at position 33, 34, and 35 are absent, and wherein the total length of the GLP-1 analogue is 26 amino acids.

4. The GLP-1 analogue according to claim 1, wherein the amino acids at position 32, 33, 34, and 35 are absent, and wherein the total length of the GLP-1 analogue is 25 amino acids.

5. The GLP-1 analogue according to claim 1, wherein the amino acids at position 31, 32, 33, 34, and 35 are absent, and wherein the total length of the GLP-1 analogue is 24 amino acids.

6. The GLP-1 analogue according to claim 1, wherein the amino acids at position 30, 31, 32, 33, 34, and 35 are absent, and wherein the total length of the GLP-1 analogue is 23 amino acids.

7. The GLP-1 analogue according to claim 1 having a sequence according to formula (II)

Formula (II)
(SEQ ID No: 3)
$Xaa_7-Xaa_8-Glu-Gly-Thr-Phe-Thr-Ser-Asp-Val-Ser-$ $Xaa_{18}-Tyr-Leu-Glu-Glu-Gln-Ala-Ala-Arg-Glu-Phe-$ $Ile-Xaa_{30}-Trp-Leu-Xaa_{33}-Xaa_{34}-Xaa_{35}-R$ wherein
- $Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
- $Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
- $Xaa_{18}$ is Ser, Lys or Arg;
- $Xaa_{30}$ is Ala, Glu, Lys, Arg or is absent;
- $Xaa_{33}$ is Val, Lys or absent;
- $Xaa_{34}$ is Lys, Glu, Arg or is absent;
- $Xaa_{35}$ is Gly, Aib or is absent;
- R is amide or is absent, or
- a derivative of the foregoing analogue where the analogue is derivatised at a Lys or Cys residue with an albumin binding residue or is pegylated.

8. The GLP-1 analogue according to claim 1, wherein the Lys and Cys amino acid residue is derivatized with A-B-C-D- wherein A- is selected from the group consisting of

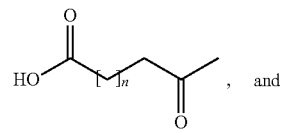, and

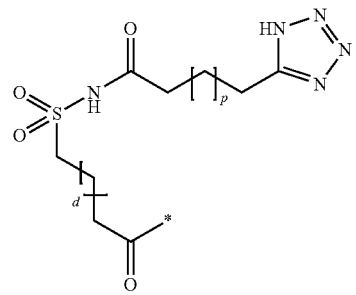

wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, -B- is selected from the group consisting of

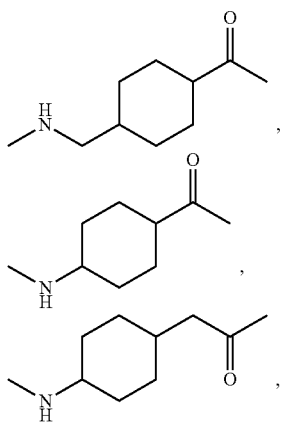

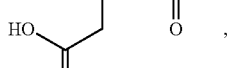

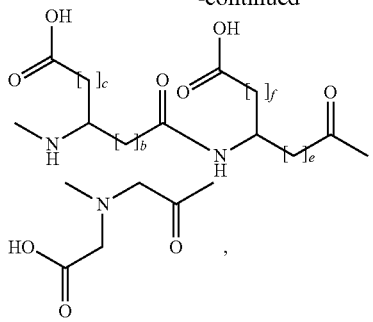 and wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and -D- is attached to said amino acid residue and is a linker.

9. The GLP-1 derivative according to claim 8, wherein D is selected from the group consisting of

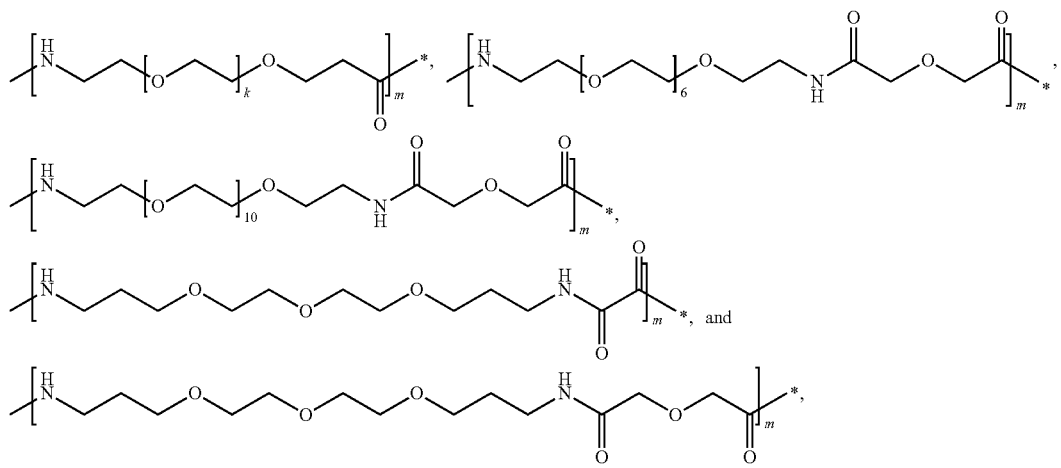

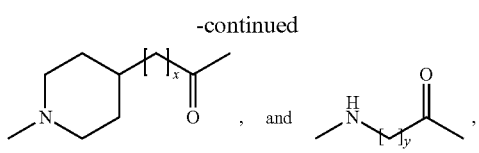

wherein x is selected from the group consisting of 0, 1, 2, 3 and 4, and y is selected from the group consisting of 1, 2, 3, 4, 5, 6, 7, 8, 9, 10, 11 and 12, -C- is selected from the group consisting of

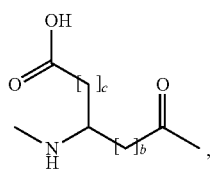

and wherein k is selected from the group consisting of 0, 1, 2, 3, 4, 5, 11 and 27, and m is selected from the group consisting of 0, 1, 2, 3, 4, 5 and 6.

10. The GLP-1 analogue or derivative thereof according to claim 1, which is selected from the following:

[Glu22,Arg26]GLP-1 (7-33) amide

N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Val25,Arg26,Leu27,Glu30, Lys33) GLP-1(7-33)amide;

N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Arg26,Glu30) GLP-1(7-33) amide;

[Glu22,Val25,Arg26] GLP-1 (7-33)amide;

[Aib8,Lys20,Glu22,Val25,Arg26,Glu30] GLP-1 (7-33) amide;

N epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-[Aib8,Lys20,Glu22,Val25,Arg26,Glu30] GLP-1 (7-33) amide;

[Glu22, Arg26]GLP-1(7-33)peptide;
[Glu22,Val25,Arg26] GLP-1 (7-32)amide;
N-epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Arg26) GLP-1(7-33) amide;
N-epsilon31 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Glu22,Val25,Arg26,Lys31) GLP-1(7-33) amide;
N-epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(DesaminoHis7,Lys20,Glu22,Arg26) GLP-1(7-33) amide;
N-epsilon31 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(DesaminoHis7,Glu22,Arg26,Lys31)GLP-1(7-33) amide;
N-epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8,Lys20,Glu22,Val25,Arg26,Leu27, Glu30,Lys31) GLP-1(7-32) amide;
N-epsilon20 {2-(2-{2-[2-(2-{2-[4-Carboxy-4-(17-carboxy-heptadecanoylamino)butyrylamino]ethoxy}ethoxy)acetylamino]ethoxy}ethoxy)acetyl}-(Aib8, Lys20,Glu22,Val25,Arg26,Leu27,Nle30,Lys31) GLP-1(7-32) amide;
N-epsilon31-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl]-[Aib8,Glu22,Val25,Arg26,Lys31]GLP-1-(7-33) amide;
[Desamino His7,Glu22,Arg26]-GLP-1 (7-34);
[Aib8,Lys20,Glu22,Val25,Arg26,Leu27,Lys31]GLP-1 (7-32) amide;
N-epsilon31-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Des aminoHis7,Asp11,Glu18,Glu22,Val25,Arg26, Asp27,Glu30,Lys31]GLP-1 (7-33) amide;
[Aib8,Glu22,Val25, Lys31]GLP-1(7-33)-amide; and
N-epsilon31-{2-(2-{2-[2-(2-{2-[4-Carboxy-4-(17-carboxy-heptadecanoylamino)butyrylamino]ethoxy}ethoxy)acetylamino]ethoxy}ethoxy)acetyl}-N-beta34-(2-(bis-carboxymethylamino)acetyl)[Aib8,Glu22, Val25,Arg26,Lys31,Dap34] GLP-1(7-34) amide.

11. A pharmaceutical composition comprising a GLP-1 analogue or derivative thereof according to claim 1 or a pharmaceutically acceptable salt, amide, alkyl, or ester thereof, and a pharmaceutically acceptable excipient.

12. The GLP-1 analogue according to claim 1, wherein the GLP-1 analogue comprises i) a C-terminal carboxylic acid group; or iii) a C-terminal amide group.

13. The GLP-1 analogue according to claim 1, wherein the amino acids at position 34 and 35 are absent, and wherein the total length of the GLP-1 analogue is 27 amino acids.

14. A method of treating hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers in a subject in need of such treatment, the method comprising administering to the subject a therapeutically effective amount of a pharmaceutical composition according to claim 11.

* * * * *

SEQUENCE LISTING

```
<160> NUMBER OF SEQ ID NOS: 19

<210> SEQ ID NO 1
<211> LENGTH: 29
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is L-his, D-his, desamino-his, 2-amino-his,
      beta-hydroxy-his, homohis, Nalpha-acetyl-his,
```

```
        alpha-fluoromethyl-his, alpha-methyl-hist, 3-pyridylalanine,
        2-pyridylalanine or 4-pyridylalanine
<220> FEATURE:
<221> NAME/KEY: MISC_FEATURE
<222> LOCATION: (2)..(2)
<223> OTHER INFORMATION: Xaa is Ala, Gly, Val, Leu, Ile, Lys, Aib,
        (1-aminocyclopropyl, -butyl-, -pentyl-, -hexyl-, -heptyl-, or
        -octyl)carboxylic acid
<220> FEATURE:
<221> NAME/KEY: MISC_FEATURE
<222> LOCATION: (3)..(3)
<223> OTHER INFORMATION: Xaa is Glu or a Glu derivative such as alpha,
        alpha dimethyl-Glu
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (12)..(12)
<223> OTHER INFORMATION: Xaa is Ser, Lys, Cys or Arg
<220> FEATURE:
<221> NAME/KEY: MISC_FEATURE
<222> LOCATION: (14)..(14)
<223> OTHER INFORMATION: Xaa is Leu, Lys or Cys
<220> FEATURE:
<221> NAME/KEY: MISC_FEATURE
<222> LOCATION: (17)..(17)
<223> OTHER INFORMATION: Xaa is Gln, Glu, Lys, Cys or Arg
<220> FEATURE:
<221> NAME/KEY: MISC_FEATURE
<222> LOCATION: (18)..(18)
<223> OTHER INFORMATION: Xaa is Ala or Asn
<220> FEATURE:
<221> NAME/KEY: MISC_FEATURE
<222> LOCATION: (19)..(19)
<223> OTHER INFORMATION: Xaa is Ala or Val
<220> FEATURE:
<221> NAME/KEY: MISC_FEATURE
<222> LOCATION: (21)..(21)
<223> OTHER INFORMATION: Xaa is Glu, Ala or Leu
<220> FEATURE:
<221> NAME/KEY: MISC_FEATURE
<222> LOCATION: (24)..(24)
<223> OTHER INFORMATION: Xaa is Ala, Glu, Lys, Arg or absent
<220> FEATURE:
<221> NAME/KEY: MISC_FEATURE
<222> LOCATION: (25)..(25)
<223> OTHER INFORMATION: Xaa is Trp, Lys, Cys or absent
<220> FEATURE:
<221> NAME/KEY: MISC_FEATURE
<222> LOCATION: (27)..(27)
<223> OTHER INFORMATION: Xaa is Val, Lys, Cys or absent
<220> FEATURE:
<221> NAME/KEY: MISC_FEATURE
<222> LOCATION: (28)..(28)
<223> OTHER INFORMATION: Xaa is Lys, Glu, Asn, Arg, Cys or absent
<220> FEATURE:
<221> NAME/KEY: MISC_FEATURE
<222> LOCATION: (29)..(29)
<223> OTHER INFORMATION: Xaa is Gly, Aib or absent;

<400> SEQUENCE: 2

Xaa Xaa Xaa Gly Thr Phe Thr Ser Asp Xaa Ser Xaa Tyr Xaa Glu Glu
1               5                   10                  15

Xaa Xaa Xaa Arg Xaa Phe Ile Xaa Xaa Leu Xaa Xaa Xaa
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: Xaa is L-his, D-his, desamino-his, 2-amino-his,
      beta-hydroxy-his, homohis, Nalpha-acetyl-his,
      alpha-fluoromethyl-his, alpha-methyl-his, 3-pyridylalanine,
      2-pyridylalanine or 4-pyridylalanine
<220> FEATURE:
<221> NAME/KEY: MISC_FEATURE
<222> LOCATION: (2)..(2)
<223> OTHER INFORMATION: Xaa is Ala, Gly, Val, Leu, Ile, Lys, Aib,
      (1-aminocyclopropyl, -butyl-, -pentyl-, -hexyl-, -heptyl-, or
      -octyl)carboxylic acid
<220> FEATURE:
<221> NAME/KEY: MISC_FEATURE
<222> LOCATION: (12)..(12)
<223> OTHER INFORMATION: Xaa is Ser, Lys or Arg
<220> FEATURE:
<221> NAME/KEY: MISC_FEATURE
<222> LOCATION: (24)..(24)
<223> OTHER INFORMATION: Xaa is Ala, Glu, Lys, Arg or is absent
<220> FEATURE:
<221> NAME/KEY: MISC_FEATURE
<222> LOCATION: (27)..(27)
<223> OTHER INFORMATION: Xaa is Val, Lys or absent
<220> FEATURE:
<221> NAME/KEY: MISC_FEATURE
<222> LOCATION: (28)..(28)
<223> OTHER INFORMATION: Xaa is Lys, Glu, Arg or is absent
<220> FEATURE:
<221> NAME/KEY: MISC_FEATURE
<222> LOCATION: (29)..(29)
<223> OTHER INFORMATION: Xaa is Gly, Aib or is absent

<400> SEQUENCE: 3

Xaa Xaa Glu Gly Thr Phe Thr Ser Asp Val Ser Xaa Tyr Leu Glu Glu
1               5                   10                  15

Gln Ala Ala Arg Glu Phe Ile Xaa Trp Leu Xaa Xaa Xaa
            20                  25

<210> SEQ ID NO 4
<211> LENGTH: 27
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Lys
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (21)..(21)
<223> OTHER INFORMATION: Xaa = Leu
<220> FEATURE:
<221> NAME/KEY: MISC_FEATURE
<222> LOCATION: (24)..(24)
<223> OTHER INFORMATION: Xaa = Glu
<220> FEATURE:
```

<221> NAME/KEY: MISC_FEATURE
<222> LOCATION: (27)..(27)
<223> OTHER INFORMATION: Xaa = Lys

<400> SEQUENCE: 4

His Xaa Glu Gly Thr Phe Thr Ser Asp Val Ser Ser Tyr Xaa Glu Xaa
1               5                   10                  15

Gln Ala Xaa Xaa Xaa Phe Ile Xaa Trp Leu Xaa
            20                  25

<210> SEQ ID NO 5
<211> LENGTH: 27
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Lys
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (24)..(24)
<223> OTHER INFORMATION: Xaa = Glu

<400> SEQUENCE: 5

His Xaa Glu Gly Thr Phe Thr Ser Asp Val Ser Ser Tyr Xaa Glu Xaa
1               5                   10                  15

Gln Ala Ala Xaa Glu Phe Ile Xaa Trp Leu Val
            20                  25

<210> SEQ ID NO 6
<211> LENGTH: 27
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Lys
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE

```
<222> LOCATION: (20)..(20)
<223> OTHER INFORMATION: Xaa = Arg
<220> FEATURE:
<221> NAME/KEY: MISC_FEATURE
<222> LOCATION: (24)..(24)
<223> OTHER INFORMATION: Xaa = Glu

<400> SEQUENCE: 6

His Xaa Glu Gly Thr Phe Thr Ser Asp Val Ser Ser Tyr Xaa Glu Xaa
 1               5                  10                  15

Gln Ala Xaa Xaa Glu Phe Ile Xaa Trp Leu Val
            20                  25

<210> SEQ ID NO 7
<211> LENGTH: 27
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Lys
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (20)..(20)
<223> OTHER INFORMATION: Xaa = Arg

<400> SEQUENCE: 7

His Xaa Glu Gly Thr Phe Thr Ser Asp Val Ser Ser Tyr Xaa Glu Xaa
 1               5                  10                  15

Gln Ala Ala Xaa Glu Phe Ile Ala Trp Leu Val
            20                  25

<210> SEQ ID NO 8
<211> LENGTH: 27
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (25)..(25)
```

```
<223> OTHER INFORMATION: Xaa = Lys

<400> SEQUENCE: 8

His Xaa Glu Gly Thr Phe Thr Ser Asp Val Ser Ser Tyr Leu Glu Xaa
1               5                   10                  15

Gln Ala Xaa Xaa Glu Phe Ile Ala Xaa Leu Val
            20                  25

<210> SEQ ID NO 9
<211> LENGTH: 27
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: misc_feature
<222> LOCATION: (1)..(1)
<223> OTHER INFORMATION: Xaa = Desamino-His
<220> FEATURE:
<221> NAME/KEY: misc_feature
<222> LOCATION: (14)..(14)
<223> OTHER INFORMATION: Xaa = Lys
<220> FEATURE:
<221> NAME/KEY: misc_feature
<222> LOCATION: (16)..(16)
<223> OTHER INFORMATION: Xaa = Glu
<220> FEATURE:
<221> NAME/KEY: misc_feature
<222> LOCATION: (20)..(20)
<223> OTHER INFORMATION: Xaa = Arg

<400> SEQUENCE: 9

Xaa Ala Glu Gly Thr Phe Thr Ser Asp Val Ser Ser Tyr Xaa Glu Xaa
1               5                   10                  15

Gln Ala Ala Xaa Glu Phe Ile Ala Trp Leu Val
            20                  25

<210> SEQ ID NO 10
<211> LENGTH: 27
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: MISC_FEATURE
<222> LOCATION: (1)..(1)
<223> OTHER INFORMATION: Xaa = Desamino-His
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (25)..(25)
<223> OTHER INFORMATION: Xaa = Lys

<400> SEQUENCE: 10

Xaa Ala Glu Gly Thr Phe Thr Ser Asp Val Ser Ser Tyr Leu Glu Xaa
1               5                   10                  15

Gln Ala Ala Xaa Glu Phe Ile Ala Xaa Leu Val
            20                  25
```

<210> SEQ ID NO 11
<211> LENGTH: 26
<212> TYPE: PRT
<213> ORGANISM: Artificial Sequence
<220> FEATURE:
<223> OTHER INFORMATION: N epsilon20
    {2-(2-{2-[2-(2-{2-[4-Carboxy-4-(17-carboxy-
    heptadecanoylamino)butyrylamino]ethoxy}-
    ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Lys
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (21)..(21)
<223> OTHER INFORMATION: Xaa = Leu
<220> FEATURE:
<221> NAME/KEY: MISC_FEATURE
<222> LOCATION: (24)..(24)
<223> OTHER INFORMATION: Xaa = Glu
<220> FEATURE:
<221> NAME/KEY: MISC_FEATURE
<222> LOCATION: (25)..(25)
<223> OTHER INFORMATION: Xaa = Lys

<400> SEQUENCE: 11

His Xaa Glu Gly Thr Phe Thr Ser Asp Val Ser Ser Tyr Xaa Glu Xaa
1               5                   10                  15

Gln Ala Xaa Xaa Xaa Phe Ile Xaa Xaa Leu
            20                  25

<210> SEQ ID NO 12
<211> LENGTH: 26
<212> TYPE: PRT
<213> ORGANISM: Artificial Sequence
<220> FEATURE:
<223> OTHER INFORMATION: N epsilon20
    {2-(2-{2-[2-(2-{2-[4-Carboxy-4-(17-carboxy-
    heptadecanoylamino)butyrylamino]ethoxy}-
    ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Lys
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:

```
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (21)..(21)
<223> OTHER INFORMATION: Xaa = Leu
<220> FEATURE:
<221> NAME/KEY: MISC_FEATURE
<222> LOCATION: (24)..(24)
<223> OTHER INFORMATION: Xaa = Nle
<220> FEATURE:
<221> NAME/KEY: MISC_FEATURE
<222> LOCATION: (25)..(25)
<223> OTHER INFORMATION: Xaa = Lys

<400> SEQUENCE: 12

His Xaa Glu Gly Thr Phe Thr Ser Asp Val Ser Ser Tyr Xaa Glu Xaa
 1               5                  10                  15

Gln Ala Xaa Xaa Xaa Phe Ile Xaa Xaa Leu
            20                  25

<210> SEQ ID NO 13
<211> LENGTH: 26
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Lys
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (21)..(21)
<223> OTHER INFORMATION: Xaa = Leu
<220> FEATURE:
<221> NAME/KEY: MISC_FEATURE
<222> LOCATION: (25)..(25)
<223> OTHER INFORMATION: Xaa = Lys

<400> SEQUENCE: 13

His Xaa Glu Gly Thr Phe Thr Ser Asp Val Ser Ser Tyr Xaa Glu Xaa
 1               5                  10                  15

Gln Ala Xaa Xaa Xaa Phe Ile Ala Xaa Leu
            20                  25

<210> SEQ ID NO 14
<211> LENGTH: 27
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
```

```
            heptadecanoylamino)butyrylamino]ethoxy}-
            ethoxy)acetylamino]ethoxy}-ethoxy)acetyl}
<220> FEATURE:
<221> NAME/KEY: MISC_FEATURE
<222> LOCATION: (1)..(1)
<223> OTHER INFORMATION: Xaa = Desamino-His
<220> FEATURE:
<221> NAME/KEY: MISC_FEATURE
<222> LOCATION: (5)..(5)
<223> OTHER INFORMATION: Xaa = Asp
<220> FEATURE:
<221> NAME/KEY: MISC_FEATURE
<222> LOCATION: (12)..(12)
<223> OTHER INFORMATION: Xaa = Glu
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (21)..(21)
<223> OTHER INFORMATION: Xaa = Asp
<220> FEATURE:
<221> NAME/KEY: MISC_FEATURE
<222> LOCATION: (24)..(24)
<223> OTHER INFORMATION: Xaa = Glu
<220> FEATURE:
<221> NAME/KEY: MISC_FEATURE
<222> LOCATION: (25)..(25)
<223> OTHER INFORMATION: Xaa = Lys

<400> SEQUENCE: 14

Xaa Ala Glu Gly Xaa Phe Thr Ser Asp Val Ser Xaa Tyr Leu Glu Xaa
1               5                   10                  15

Gln Ala Xaa Xaa Xaa Phe Ile Xaa Xaa Leu Val
            20                  25

<210> SEQ ID NO 15
<211> LENGTH: 27
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (25)..(25)
<223> OTHER INFORMATION: Xaa = Lys

<400> SEQUENCE: 15

His Xaa Glu Gly Thr Phe Thr Ser Asp Val Ser Ser Tyr Leu Glu Xaa
1               5                   10                  15
```

```
Gln Ala Xaa Lys Glu Phe Ile Ala Xaa Leu Val
            20                  25

<210> SEQ ID NO 16
<211> LENGTH: 28
<212> TYPE: PRT
<213> ORGANISM: Artificial Sequence
<220> FEATURE:
<223> OTHER INFORMATION: N epsilon20
      {2-(2-{2-[2-(2-{2-[4-Carboxy-4-(17-carboxy-
      heptadecanoylamino)butyrylamino]ethoxy}-
      ethoxy)acetylamino]ethoxy}-ethoxy)acetyl}
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (25)..(25)
<223> OTHER INFORMATION: Xaa = Lys
<220> FEATURE:
<221> NAME/KEY: MISC_FEATURE
<222> LOCATION: (28)..(28)
<223> OTHER INFORMATION: Xaa = Dap

<400> SEQUENCE: 16

His Xaa Glu Gly Thr Phe Thr Ser Asp Val Ser Ser Tyr Leu Glu Xaa
1               5                   10                  15

Gln Ala Xaa Xaa Glu Phe Ile Ala Xaa Leu Val Xaa
            20                  25

<210> SEQ ID NO 17
<211> LENGTH: 27
<212> TYPE: PRT
<213> ORGANISM: Artificial Sequence
<220> FEATURE:
<223> OTHER INFORMATION: N-epsilon31-[2-(2-{2-[2-(2-{2-[(S)-4-Carboxy-4-
      ({trans-4-[(19-carboxynonadecanoylamino)methyl]cyclohexane-
      carbonyl}amino)butyrylamino]ethoxy}ethoxy)acetyl-
      amino]ethoxy}ethoxy)acetyl]
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (25)..(25)
<223> OTHER INFORMATION: Xaa = Lys

<400> SEQUENCE: 17
```

```
His Xaa Glu Gly Thr Phe Thr Ser Asp Val Ser Ser Tyr Leu Glu Xaa
1               5                   10                  15

Gln Ala Xaa Xaa Glu Phe Ile Ala Xaa Leu Val
            20                  25
```

<210> SEQ ID NO 18
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (14)..(14)
<223> OTHER INFORMATION: Xaa = Lys
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (24)..(24)
<223> OTHER INFORMATION: Xaa = Glu

<400> SEQUENCE: 18

```
His Xaa Glu Gly Thr Phe Thr Ser Asp Val Ser Ser Tyr Xaa Glu Xaa
1               5                   10                  15

Gln Ala Xaa Xaa Glu Phe Ile Xaa Trp Leu Val
            20                  25
```

<210> SEQ ID NO 19
<211> LENGTH: 27
<212> TYPE: PRT
<213> ORGANISM: Artificial Sequence
<220> FEATURE:
<223> OTHER INFORMATION: N-epsilon31-[2-(2-{2-[2-(2-{2-[(S)-4-Carboxy-4-
    ({trans-4-[(19-carboxynonadecanoylamino)methyl]cyclohexane-
    carbonyl}amino)butyrylamino]ethoxy}ethoxy)acetyl-
    amino]ethoxy}ethoxy)acetyl]
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (16)..(16)
<223> OTHER INFORMATION: Xaa = Glu
<220> FEATURE:
<221> NAME/KEY: MISC_FEATURE
<222> LOCATION: (19)..(19)
<223> OTHER INFORMATION: Xaa = Val
<220> FEATURE:
<221> NAME/KEY: MISC_FEATURE
<222> LOCATION: (20)..(20)
<223> OTHER INFORMATION: Xaa = Arg
<220> FEATURE:
<221> NAME/KEY: MISC_FEATURE
<222> LOCATION: (25)..(25)
<223> OTHER INFORMATION: Xaa = Lys

<400> SEQUENCE: 19

```
His Xaa Glu Gly Thr Phe Thr Ser Asp Val Ser Ser Tyr Leu Glu Xaa
1               5                   10                  15

Gln Ala Xaa Xaa Glu Phe Ile Ala Xaa Leu Val
            20              25
```